United States Patent
Baumann et al.

(10) Patent No.: US 12,054,732 B2
(45) Date of Patent: Aug. 6, 2024

(54) COMPOSITIONS AND METHODS OF MODIFYING A PLANT GENOME TO PRODUCE A MS1 OR MS5 MALE-STERILE PLANT

(71) Applicant: PIONEER HI-BRED INTERNATIONAL, INC., Johnston, IA (US)

(72) Inventors: Ute Baumann, Glen Osmond (AU); Andrew Mark Cigan, Madison, WI (US); Margaret Anne Pallotta, Norwood (AU); Manjit Singh, Johnston, IA (US); Radoslaw Suchecki, Pasadena (AU); Nathan Spencer Watson-Haigh, Novar Gardens (AU); Ryan Whitford, Eastwood (AU)

(73) Assignee: PIONEER HI-BRED INTERNATIONAL, INC., IA (US)

( * ) Notice: Subject to any disclaimer, the term of this patent is extended or adjusted under 35 U.S.C. 154(b) by 0 days.

(21) Appl. No.: 16/769,019

(22) PCT Filed: Dec. 10, 2018

(86) PCT No.: PCT/US2018/064735
§ 371 (c)(1),
(2) Date: Jun. 2, 2020

(87) PCT Pub. No.: WO2019/118342
PCT Pub. Date: Jun. 20, 2019

(65) Prior Publication Data
US 2021/0222192 A1   Jul. 22, 2021

Related U.S. Application Data

(60) Provisional application No. 62/597,002, filed on Dec. 11, 2017.

(51) Int. Cl.
*C12N 15/82* (2006.01)
*C07K 14/415* (2006.01)

(52) U.S. Cl.
CPC ........ *C12N 15/8289* (2013.01); *C07K 14/415* (2013.01); *C12N 15/8213* (2013.01)

(58) Field of Classification Search
None
See application file for complete search history.

(56) References Cited

U.S. PATENT DOCUMENTS

| | | | |
|---|---|---|---|
| 2012/0005781 A1 | 1/2012 | Alexandrov et al. | |
| 2014/0020131 A1* | 1/2014 | Bidney | C12N 15/8213 800/278 |
| 2015/0067913 A1 | 3/2015 | Fox et al. | |
| 2017/0058295 A1 | 3/2017 | Bidney et al. | |
| 2017/0298383 A1 | 10/2017 | Albertsen et al. | |

FOREIGN PATENT DOCUMENTS

| | | | |
|---|---|---|---|
| WO | 1997/30581 A1 | 8/1997 | |
| WO | WO-9730581 A1 * | 8/1997 | ......... C12N 15/8289 |
| WO | 2017/079724 A1 | 5/2017 | |

OTHER PUBLICATIONS

International Barley Genome Sequencing Consortium, A physical, genetic and functional sequence assembly of the barley genome, Nature, Nov. 29, 2012 (Year: 2012).*
F2D569_HORVV, UniProtKB/TrEMBL, May 31, 2011 (Year: 2011).*
NCBI Blast_Protein Sequence, https://blast.ncbi.nlm.nih.gov/Blast. cgi#sort_mark, 2021 (Year: 2021).*
Chr3D_316.4M-316.4M—Genome Data Viewer, https://www.ncbi. nlm.nih.gov/genome/gdv/browser/protein/?id=KAF7036808.1, 2021 (Year: 2021).*
UniPROTKB—Q9SUC3 (MS5_ARATH), UniProt, Oct. 29, 2014 (Year: 2014).*
Zhou, A new male sterile mutant in LZ in wheat (*Triticum aestivum* L.), Euphytica, 2008, Issue 159, pp. 403-410 (Year: 2008).*
International Search Report and Written Opinion for International Application No. PCT/US2018/064735, dated Mar. 22, 2019.
International Preliminary Report on Patentability for International Application No. PCT/US2018/064735, mailed Jun. 25, 2020, 9 Pages.

\* cited by examiner

*Primary Examiner* — Weihua Fan
*Assistant Examiner* — Brian James Sullivan

(57) ABSTRACT

Compositions and methods are provided for genome modification of a nucleotide sequence located in or near a male fertility gene of Ms1 or Ms5 in the genome of a plant cell or plant to produce a male-sterile plant. In some examples, the methods and compositions employ a guide RNA/Cas endonuclease system for modifying or altering target sites located in or near a male fertility gene of Ms1 or Ms5 in the genome of a plant cell, plant or seed to produce a male-sterile plant. Also provided are compositions and methods employing a guide polynucleotide/Cas endonuclease system for genome modification a nucleotide sequence located in or near a male fertility gene of Ms1 or Ms5 in the genome of a plant cell to produce a male-sterile plant. Compositions and methods are also provided for restoring fertility to a Ms1 or Ms5 nucleotide sequence to a male-sterile Ms1 or Ms5 plant produced using the methods and compositions described herein.

5 Claims, 2 Drawing Sheets
Specification includes a Sequence Listing.

```
wheat_MS5-A    1  MAPTALLIVVLAVAALHAPAASAALSQEPPATPCAAAIVSFSPCLAHVAVVAPPALPSPAPTSACCAAFLRAVSSGDGEG   80
barley_MS5        MAPPALLLLVLAVTALHAHAASAALSQEPPATPCAAAIVSFSPCLAHVAVVAPPALPSSAPTSACCAAFLRAVSSGDGEG wheat_MS5-A   81  -GGGEGCFCHLLIRNPLLLGFPVDAARLGTLLPTCASAKTSAATAAEAEALFADKCRELKSLPEMHFTPPSPPPAPKLSPA   160
barley_MS5        AGGGEGCFCHLLIRDPLLLGFPVDAARLGALLPTCASAKTSAATAVEAEALFADKCRELKSLPEMHFTPPSPPPAPKLSPA wheat_MS5-A  161  AVTEPASPTPKMEEHSTSTTPVSDDRSGSDALCACRVFLVALVLGAAVLITLQF   214   (SEQ ID NO:19)
barley_MS5        AVPEPAFPAPKMEEHSSS-TPAPGDRSGSDAVCACRVFLVALVLGAAVLITLNF         (SEQ ID NO:39)
```

FIG. 1

```
                                                                              80
wheat_MS5-3A     MAPTALLIVLVLAVAALHAPAA----------SAALSQEPPATPCAAAIVSFSPCLAHVAVVAPPALPSPAPTSACCAAFLR
barley_MS5       MAPPALLLLVLAVTALHAHAA-----------SAALSQEPPATPCAAAIVSFSPCLAHVAVVAPPALPSSAPTSACCAAFLR
Brachypodium_MS5 MGPTALHVVIAVAALLIAAAA-----------SAASSQEPPATPCAAAIVAFSPCLAHVAVVAPPAVAAPTGACCAAFLR
Rice_MS5         MGPTALHLIAVAVAAVVAAAAAPASASASAAGAFSEVPPETPCAAAIVSVAPCLAHVAVVAPPARPAPAPTEACCAAFLR 160
wheat_MS5-3A     AVSSGDGEG-GGGEGCFCHLLRNPLLLGFPVDAARLGTLLPTCA---SAKTSAATAEEAEALFADKCR-ELKSLPEMHFTP
barley_MS5       AVSSGDGEGAGGGEGCFCHLLRDPLLLGFPVDAARLGALLPTCA---SAKTSAATAVEAEALFADKCR-ELKSLPEMHFTP
Brachypodium_MS5 AVSAGDGEG-GGGEGCFCHLVRDPLLFGFPVDVGRLGALLPTCA---SANASAATTVEAEALFADKCR-ELKSLPEMHLSP
Rice_MS5         GVSPSG-----GGGEGCFCHLLRDPLLLGFPVNTARLGALLPTCAAANANANASAAAAVEAATLFADTCRADLKSLPEMRFLP 229
wheat_MS5-3A     PSPPPPAPKLSPAAVTEPASPTPKMEEHSTSTTPVSDDRSGSDALCACRVFLVALV--LGAAVLITLQF- (SEQ ID NO:19)
barley_MS5       PSPPPAPKLSPAAVPEPAFPAPKMEEHSSSTPA-PGDRSGSDAVCACRVFLVALV--LGAAVLITLNF- (SEQ ID NO:39)
Brachypodium_MS5 PSPPPAPKLSPAAVPGPAS-SPKVEA-AQSTTSTPRDRSGSDGLCAFRVSLMALV-FTAAVLIMLQLW (SEQ ID NO:44)
Rice_MS5         -DPPPTPTISPAAV--PGSMPPTTEERSTPVPVPPQDRSGSETSTPSRNFLVVLLALTAAAADLIQL- (SEQ ID NO:49)
```

FIG. 2

COMPOSITIONS AND METHODS OF MODIFYING A PLANT GENOME TO PRODUCE A MS1 OR MS5 MALE-STERILE PLANT

FIELD

The disclosure relates to the field of plant molecular biology, in particular, to compositions and methods of modifying a plant's genome to alter the male-fertility of a plant.

CROSS REFERENCE

This application is a 371 (National Stage) of PCT/US2018/064735, filed on Dec. 10, 2018, which claims the benefit of and priority to U.S. Provisional Application No. 62/597,002, filed Dec. 11, 2017, each of which is incorporated herein by reference in its entirety.

REFERENCE TO SEQUENCE LISTING SUBMITTED ELECTRONICALLY

The official copy of the sequence listing is submitted electronically via EFS-Web as an ASCII formatted sequence listing with a file named RTS20250GWOPCT_SeqLstg_ST25.txt, produced on Dec. 10, 2018, and having a size 152 kilobytes and is filed concurrently with the specification. The sequence listing contained in this ASCII formatted document is part of the specification and is herein incorporated by reference in its entirety.

BACKGROUND

Development of hybrid plant breeding has made possible considerable advances in quality and quantity of crops produced. Increased yield and combination of desirable characteristics, such as resistance to disease and insects, heat and drought tolerance, along with variations in plant composition are all possible because of hybridization procedures. These procedures frequently rely heavily on providing for a male parent contributing pollen to a female parent to produce the resulting hybrid.

Field crops are bred through techniques that take advantage of the plant's method of pollination. A plant is self-pollinating if pollen from one flower is transferred to the same or another flower of the same plant or a genetically identical plant. A plant is cross-pollinated if the pollen comes from a flower on a different plant.

In certain species, such as *Brassica campestris*, the plant is normally self-sterile and can only be cross-pollinated. In self-pollinating species, such as soybeans, cotton and wheat, the male and female plants are anatomically juxtaposed. During natural pollination, the male reproductive organs of a given flower pollinate the female reproductive organs of the same flower. Maize has male flowers, located on the tassel, and female flowers, located on the ear, on the same plant and can be bred by both self-pollination and cross-pollination techniques, The development of hybrids requires the crossing of homozygous inbred parents. A hybrid variety is the cross of two such inbred lines, each of which may have one or more desirable characteristics lacked by the other or which complement the other. The new inbreds are crossed with other inbred lines and the hybrids from these crosses are evaluated to determine which have commercial potential.

The hybrid progeny of the first generation is designated $F_1$. In the development of hybrids only the $F_1$ hybrid plants are sought. The $F_1$ hybrid is more vigorous than its inbred parents. This hybrid vigor, or heterosis, can be manifested in many ways, including increased vegetative growth and increased yield.

During hybrid seed production, it is desirable to prevent self-pollination of the female inbred to avoid production and harvesting of female inbred seeds, since they exhibit less vigor than the hybrid seeds. To increase commercial quantities of the resulting hybrid seed, hybrid seed is often obtained using male-sterile female parents. Manual emasculation of the female can be labor intensive and/or impractical, depending on the crop. For example, in wheat, both male flowers and female flowers are located within the same floret on a spike making it challenging to prevent self-pollination. As a result, male-sterile female plants created from either chemical or genetic manipulations are often used in hybrid seed production.

SUMMARY

Provided herein are methods for producing male-sterile plants. In one embodiment, the method includes introducing a genetic modification into at least one or more endogenous MS1 or MS5 polynucleotide sequences in a plant cell, wherein the genetic modification confers male sterility to a plant obtained from the plant cell. In one aspect, the genetic modification is introduced using biotechnology approaches. Accordingly, also provided herein are male-sterile plants that contain a genetic modification in at least one or more endogenous MS1 or MS5 polynucleotide sequences. The genetic modification may confer male sterility to a plant obtained from the plant cell.

In yet another aspect, the method includes providing to a plant cell a guide RNA and a Cas endonuclease. The RNA and Cas endonuclease are capable of forming a complex that enables the Cas endonuclease to introduce a double strand break at a target site located in or near a male fertility gene of MS1 or MS5. The method may additionally include identifying at least one plant cell that has the modification. The modification may be at least one deletion, insertion, or substitution of one or more nucleotides in a MS1 or MS5 gene that confers male-sterility to a plant. A male-sterile plant may be obtained from the plant cell.

A male-sterile plant may have at least one altered target site that confers male-sterility to the plant. The target site may originate from a corresponding target site that was recognized and cleaved by a guideRNA/Cas endonuclease system. The target site may be located in or near a male fertility gene of MS1 or MS5 and affect the expression level of the MS1 or MS5 gene so that the plant is male-sterile.

Also provided herein is a method for producing a male sterile plant that includes obtaining or providing a first plant comprising at least one Cas endonuclease capable of introducing a double strand break at a genomic target site located in a male fertility gene locus of MS1 or MS5 in the plant genome and a second plant comprising a guide RNA that is capable of forming a complex with the Cas endonuclease. In some aspects, the first and second plants may be crossed and the progeny evaluated for those that have an altered target site. Male-sterile progeny plants may be selected. Accordingly, also included herein are male-sterile progeny plants produced by any of the methods disclosed herein. The progeny plant may include at least one altered target site that originated from a corresponding target site that was recognized and cleaved by a guideRNA/Cas endonuclease system. The altered target site may be located in or near a male fertility gene of MS1 or MS5 and affect the expression level of the MS1 or MS5 gene so that the plant is male-sterile.

A method of modifying the male-fertility of a plant that includes introducing at least one guide RNA, at least one polynucleotide modification template and at least one Cas endonuclease into a plant cell is provided herein. The Cas endonuclease may introduce a double-strand break at a target site located in or near a MS1 or MS5 gene in the genome of the plant cell. The polynucleotide modification template includes at least one nucleotide modification of a nucleotide sequence at the target site, and the modification modifies the expression level of the MS1 or MS5 gene. A male-sterile plant may be obtained from the plant cell.

Also provided herein are methods for restoring male fertility in a male-sterile plant. A male sterile plant produced by any of the methods disclosed herein and having one or more endogenous MS1 or MS5 genes with a genetic modification that confers male-sterility to the plant may have fertility restored by introducing one or more polynucleotide sequences that encode a MS1 or MS5 polypeptide.

Also provided herein are isolated nucleic acids that impact male fertility of a plant. In some aspects, an isolated nucleic acid that impacts male fertility of a plant is a polynucleotide sequence of: (a) a polynucleotide comprising the sequence set forth in SEQ ID NO: 16, 18, 21, 23-24, 28-29, 31-32, 199, 36, 38, 41, 43, 46, 48, 51 or 53; (b) a polynucleotide having at least 85%, 90% or 95% sequence identity to SEQ ID NO: 16, 18, 21, 23-24, 28-29, 31-32, 199, 36, 38, 41, 43, 46, 48, 51 or 53; (c) a polynucleotide that encodes a polypeptide having at least 85%, 90% or 95% sequence identity to SEQ ID NO: 19, 25-26, 33-34, 39, 44, 49, or 54; (d) a polynucleotide that encodes a polypeptide of SEQ ID NO: 19, 25-26, 33-34, 39, 44, 49, or 54; (e) a polynucleotide sequence which hybridizes to the full length of SEQ ID NO: 16, 18, 21, 23-24, 28-29, 31-32, 199, 36, 38, 41, 43, 46, 48, 51 or 53 under highly stringent conditions of a wash of 0.1 SSC, 0.1% (w/v) SDS at 65 degrees Celsius. In some aspects, the nucleic acid is in an expression vector.

Also provided herein is an isolated polypeptide that impacts the male fertility of a plant. In some aspects, the isolated polypeptide that impacts male fertility of a plant is an amino acid sequence of: (a) an amino acid sequence that has at least 85%, 90% or 95% sequence identity to the amino acid sequence set forth in SEQ ID NO: 19, 25-26, 33-34, 39, 44, 49, or 54, wherein said polypeptide impacts the male fertility of the plant; (b) an amino acid sequence comprising the amino acid sequence set forth in SEQ ID NO: 19, 25-26, 33-34, 39, 44, 49, or 54; (c) an amino acid sequence comprising at least 100 contiguous amino acids of the amino acid sequence set forth in SEQ ID NO: 19, 25-26, 33-34, 39, 44, 49, or 54; (d) an amino acid sequence encoded by a polynucleotide that has at least 85%, 90% or 95% sequence identity to SEQ ID NO: 16, 18, 21, 23-24, 28-29, 31-32, 199, 36, 38, 41, 43, 46, 48, 51 or 53; and (e) an amino acid sequence encoded by a polynucleotide of SEQ ID NO: 16, 18, 21, 23-24, 28-29, 31-32, 199, 36, 38, 41, 43, 46, 48, 51 or 53; and (f) a polynucleotide sequence which hybridizes to the full length of SEQ ID NO: 16, 18, 21, 23-24, 28-29, 31-32, 199, 36, 38, 41, 43, 46, 48, 51 or 53, or 55 under highly stringent conditions of a wash of 0.1 SSC, 0.1% (w/v) SDS at 65 degrees Celsius. Also provided herein are plant cells or plants having the nucleic acid and/or expressing the polypeptide.

In another aspect, disclosed herein is an isolated regulatory region driving male-tissue-preferred or specific expression that includes the sequence of SEQ ID NO: 17, 22, 30, 37, 42, 47, 52, or 200 and functional fragments thereof. Also disclosed herein are plant cells comprising the regulatory region. The regulatory region may be operably linked to a heterologous coding sequence. In some aspects, the regulatory region is included in a DNA construct to drive expression of a sequence of interest, for example, a heterologous polynucleotide. The regulatory region may be used to express a polynucleotide of interest in male tissue of a plant. In one aspect, the method includes introducing into the plant a polynucleotide having a polynucleotide sequence of SEQ ID NO: 17, 22, 30, 37, 42, 47, 52, or 200, and functional fragments thereof. The polynucleotide sequence may confer male-tissue-specific or preferred expression of an operably linked sequence.

BRIEF DESCRIPTION OF THE FIGURES

FIG. 1 shows an alignment of barley (SEQ ID NO:39) and wheat (SEQ ID NO:19) Ms5 amino acid sequences.

FIG. 2 is an alignment of MS5 homologues of *Hordeum vulgare* (SEQ ID NO:39), *Triticum aestivum* (SEQ ID NO:19), *Brachypodium distachyon* (SEQ ID NO:44) and *Oryza sativa* (SEQ ID NO:49).

DETAILED DESCRIPTION

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

Mutations that cause male sterility in plants have the potential to be useful in methods for hybrid seed production. For example, use of a male-sterile female inbred plant as a parent to produce hybrid seed can lower production costs by eliminating the need for the labor-intensive removal of male flowers and self-pollination of the female inbred. Emasculation of wheat can be especially challenging since the male flowers and female flowers are located within the same floret. This makes it difficult to prevent self-pollination of the female and fertilize it with pollen from another wheat plant. Self-pollination results in seed of the female inbred being harvested along with the hybrid seed which is normally produced. Female inbred seed does not exhibit heterosis and therefore is not as commercially desirable as $F_1$ seed. Thus, use of a male-sterile female inbred prevents self-fertilization while maintaining the purity of hybrid seeds.

Mutations that cause male sterility in crop plants such as maize, wheat and rice have been produced by a variety of methods such as X-rays or UV-irradiations, chemical treatments, or transposable element insertions (ms23, ms25, ms26, ms32) (Chaubal et al. 2000) Am J Bot 87:1193-1201). However, such methods are random mutagenesis methods that induce mutations randomly throughout the genome and not just in the gene of interest. Typically, with such random mutagenesis methods, it requires considerable effort to identify a plant that contains a mutation in the gene of interest and it is by no means certain that such a plant will be identified. Furthermore, with random mutagenesis methods, each plant tested is likely to carry multiple mutations. Therefore, a plant that is identified with the mutation in the gene of interest must be backcrossed for several or more generations to eliminate the undesired mutations.

In contrast to such random mutagenesis methods, the described herein are methods for producing male sterile plants by introducing a genetic modification into at least one or more endogenous fertility genes, such as MS1 or MS5 polynucleotide sequences, in a plant cell. The introduced genetic modification confers male sterility to a plant arising from the plant cell. Preferably the plant is a crop plant.

PCT Patent publication WO2016048891A1, published Mar. 31, 2016, describes a male fertility gene referred to as "MS1" that is located on wheat chromosome 4BS and encodes a glycosylphosphatidylinositol (GPI)-anchored nsLTP (LTPG) polypeptide (referred to as TaLTPGI) important to male fertility. Examples of DNA and polypeptide sequences of barley, wheat, rice, and Brachypodium Ms1 are disclosed in WO2016048891A1, published Mar. 31, 2016.

A mutated gene in FS20 referred to as ms5 was mapped to the long arm on wheat chromosome 3A. See Klindworth et al. "Chromosomal Location of Genetic Male Sterility Genes in Four Mutants of Hexaploid Wheat" Crop Science (2002) 42:1447-1450.

Additionally, the present disclosure includes the following MS1 and MS5 polynucleotides and polypeptides:

TABLE 1

Summary of SEQ ID NOS:

| SEQ ID NO: | Description |
|---|---|
| 1 | Wheat Ms1 A genomic (exon-intron) |
| 2 | Wheat Ms1 A promoter |
| 3 | Wheat Ms1 A coding |
| 4 | Wheat Ms1 A amino acid |
| 5 | Wheat Ms1 A terminator |
| 6 | Wheat Ms1 B genomic (exon-intron) |
| 7 | Wheat Ms1 B promoter |
| 8 | Wheat Ms1 B coding |
| 9 | Wheat Ms1 B amino acid |
| 10 | Wheat Ms1 B terminator |
| 11 | Wheat Ms1 D genomic (exon-intron) |
| 12 | Wheat Ms1 D promoter |
| 13 | Wheat Ms1 D coding |
| 14 | Wheat Ms1 D amino acid |
| 15 | Wheat Ms1 D terminator |
| 16 | Wheat Ms5 3A genomic (exon-intron) |
| 17 | Wheat Ms5 3A promoter |
| 18 | Wheat Ms5 3A coding |
| 19 | Wheat Ms5 3A amino acid |
| 20 | Wheat Ms5 3A terminator |
| 21 | Wheat Ms5 3B genomic (exon-intron) |
| 22 | Wheat Ms5 3B promoter |
| 23 | Wheat Ms5 3B coding |
| 24 | Wheat Ms5 3B coding |
| 25 | Wheat Ms5 3B amino acid |
| 26 | Wheat Ms5 3B amino acid |
| 27 | Wheat Ms5 3B terminator |
| 28 | Wheat Ms5 3D genomic (exon-intron) |
| 29 | Wheat Ms5 3D genomic (exon-intron) |
| 30 | Wheat Ms5 3D promoter |
| 31 | Wheat Ms5 3D coding |
| 32 | Wheat Ms5 3D coding |
| 33 | Wheat Ms5 3D amino acid |
| 34 | Wheat Ms5 3D amino acid |
| 35 | Wheat Ms5 3D terminator |
| 36 | Barley MS5 genomic (exon-intron) |
| 37 | Barley Ms5 promoter |
| 38 | Barley Ms5 coding |
| 39 | Barley Ms5 amino acid |
| 40 | Barley Ms5 terminator |
| 41 | Brachypodium distachyon Ms5 genomic (exon-intron) |

TABLE 1-continued

Summary of SEQ ID NOS:

| SEQ ID NO: | Description |
|---|---|
| 42 | Brachypodium distachyon Ms5 promoter |
| 43 | Brachypodium distachyon Ms5 coding |
| 44 | Brachypodium distachyon Ms5 amino acid |
| 45 | Brachypodium distachyon Ms5 terminator |
| 46 | Rice Ms5 genomic (exon-intron) |
| 47 | Rice Ms5 promoter |
| 48 | Rice Ms5 coding |
| 49 | Rice Ms5 amino acid |
| 50 | Rice Ms5 terminator |
| 51 | Maize Ms5 genomic (exon-intron) |
| 52 | Maize Ms5 promoter |
| 53 | Maize Ms5 coding |
| 54 | Maize Ms5 amino acid |
| 55 | Maize Ms5 terminator |
| 56 | Wheat Ms1 B CR1 target |
| 57 | Wheat Ms1 B CR2 target |
| 58 | Wheat Ms1 B CR3 target |
| 59 | Wheat Ms1 B CR4 target |
| 60 | Wheat Ms1 B CR5 target |
| 61 | Wheat Ms1 B CR6 target |
| 62 | Wheat Ms1 B CR7 target |
| 63 | Wheat Ms1 B CR8 target |
| 64 | Wheat Ms1 B CR9 target |
| 65 | Wheat Ms1 B CR10 target |
| 66 | Wheat Ms1 B CR11 target |
| 67 | Wheat Ms5 CR1 target |
| 68 | Wheat Ms5 CR2 target |
| 69 | Wheat Ms5 CR3 target |
| 70 | Wheat Ms5 CR4 target |
| 71 | Wheat Ms5 CR5 target |
| 72 | Wheat Ms5 CR6 target |
| 73 | Wheat Ms5 CR7 target |
| 74 | Wheat Ms5 CR8 target |
| 75 | Wheat Ms5 CR9 target |
| 76 | Wheat Ms5 CR10 target |
| 77 | Wheat Ms5 CR11 target |
| 78 | Wheat Ms5 CR12 target |
| 79 | Wheat Ms5 CR13 target |
| 80 | Wheat Ms5 CR14 target |
| 81 | Wheat Ms5 CR15 target |
| 82 | Wheat Ms1 CR1 guide |
| 83 | Wheat Ms1 CR2 guide |
| 84 | Wheat Ms1 CR3 guide |
| 85 | Wheat Ms1 CR4 guide |
| 86 | Wheat Ms1 CR5 guide |
| 87 | Wheat Ms1 CR6 guide |
| 88 | Wheat Ms1 CR7 guide |
| 89 | Wheat Ms1 CR8 guide |
| 90 | Wheat Ms1 CR9 guide |
| 91 | Wheat Ms1 CR10 guide |
| 92 | Wheat Ms1 CR11 guide |
| 93 | Wheat Ms5 CR1 guide |
| 94 | Wheat Ms5 CR2 guide |
| 95 | Wheat Ms5 CR3 guide |
| 96 | Wheat Ms5 CR4 guide |
| 97 | Wheat Ms5 CR5 guide |
| 98 | Wheat Ms5 CR6 guide |
| 99 | Wheat Ms5 CR7 guide |
| 100 | Wheat Ms5 CR8 guide |
| 101 | Wheat Ms5 CR9 guide |
| 102 | Wheat Ms5 CR10 guide |
| 103 | Wheat Ms5 CR11 guide |
| 104 | Wheat Ms5 CR12 guide |
| 105 | Wheat Ms5 CR13 guide |
| 106 | Wheat Ms5 CR14 guide |
| 107 | Wheat Ms5 CR15 guide |
| 108 | Genome edit insertion of one nucleotide(A) at position 18 of wheat MS1 B coding sequence |
| 109 | Genome edit insertion of one nucleotide(T) at position 18 of wheat MS1 B coding sequence |

TABLE 1-continued

Summary of SEQ ID NOS:

| SEQ ID NO: | Description |
|---|---|
| 110 | Genome edit insertion of one nucleotide(C) at position 18 of wheat MS1 B coding sequence |
| 111 | Genome edit deletion of three nucleotides at position 18 of wheat MS1 B coding sequence |
| 112 | Wheat 3A marker MP0061 amplicon |
| 113 | Wheat 3A marker MP0070 amplicon |
| 114 | Wheat 3A marker MP0079 amplicon |
| 115 | Wheat 3A marker MP0090 amplicon |
| 116 | Wheat 3A marker MP0091 amplicon |
| 117 | Wheat 3A marker MP0156 amplicon |
| 118 | Wheat 3A marker MP0179 amplicon |
| 119 | Wheat 3A marker MP0182 amplicon |
| 120 | Wheat 3A marker MP0190 amplicon |
| 121 | Wheat 3A marker MP0191 amplicon |
| 122 | Wheat 3A marker MP0192 amplicon |
| 123 | Wheat 3A marker MP0201 amplicon |
| 124 | Wheat 3D marker MP0126 amplicon |
| 125 | Wheat 3D marker MP0127 amplicon |
| 126 | Wheat 3D marker MP0130 amplicon |
| 127 | Wheat 3D marker MP0131 amplicon |
| 128 | Wheat 3D marker MP0211 amplicon |
| 129 | Wheat 3D marker MP0212 amplicon |
| 130 | Wheat 3D marker MP0215 amplicon |
| 131 | Wheat 3D marker MP0216 amplicon |
| 132 | Wheat Ms5 3A qRT-PCR primer Forward |
| 133 | Wheat Ms5 3A qRT-PCR primer Reverse |
| 134 | Wheat Ms5 3B qRT-PCR primer Forward |
| 135 | Wheat Ms5 3B qRT-PCR primer Reverse |
| 136 | Wheat Ms5 3D qRT-PCR primer Forward |
| 137 | Wheat Ms5 3D qRT-PCR primer Reverse |
| 138 | Wheat 3A marker MP0061 KASP primer Allele-specific forward primer X |
| 139 | Wheat 3A marker MP0061 KASP primer Allele-specific forward primer Y |
| 140 | Wheat 3A marker MP0061 KASP reverse primer |
| 141 | Wheat 3A marker MP0070 KASP primer Allele-specific forward primer X |
| 142 | Wheat 3A marker MP0070 KASP primer Allele-specific forward primer Y |
| 143 | Wheat 3A marker MP0070 KASP reverse primer |
| 144 | Wheat 3A marker MP0079 KASP primer Allele-specific forward primer X |
| 145 | Wheat 3A marker MP0079 KASP primer Allele-specific forward primer Y |
| 146 | Wheat 3A marker MP0079 KASP reverse primer |
| 147 | Wheat 3A marker MP0090 KASP primer Allele-specific forward primer X |
| 148 | Wheat 3A marker MP0090 KASP primer Allele-specific forward primer Y |
| 149 | Wheat 3A marker MP0090 KASP reverse primer |
| 150 | Wheat 3A marker MP0091 KASP primer Allele-specific forward primer X |
| 151 | Wheat 3A marker MP0091 KASP primer Allele-specific forward primer Y |
| 152 | Wheat 3A marker MP0091 KASP reverse primer |
| 153 | Wheat 3A marker MP0156 KASP primer Allele-specific forward primer X |
| 154 | Wheat 3A marker MP0156 KASP primer Allele-specific forward primer Y |
| 155 | Wheat 3A marker MP0156 KASP reverse primer |
| 156 | Wheat 3A marker MP0179 KASP primer Allele-specific forward primer X |
| 157 | Wheat 3A marker MP0179 KASP primer Allele-specific forward primer Y |
| 158 | Wheat 3A marker MP0179 KASP reverse primer |
| 159 | Wheat 3A marker MP0182 KASP primer Allele-specific forward primer X |
| 160 | Wheat 3A marker MP0182 KASP primer Allele-specific forward primer Y |
| 161 | Wheat 3A marker MP0182 KASP reverse primer |
| 162 | Wheat 3A marker MP0190 KASP primer Allele-specific forward primer X |
| 163 | Wheat 3A marker MP0190 KASP primer Allele-specific forward primer Y |
| 164 | Wheat 3A marker MP0190 KASP reverse primer |
| 165 | Wheat 3A marker MP0191 KASP primer Allele-specific forward primer X |
| 166 | Wheat 3A marker MP0191 KASP primer Allele-specific forward primer Y |
| 167 | Wheat 3A marker MP0191 KASP reverse primer |
| 168 | Wheat 3A marker MP0192 KASP primer Allele-specific forward primer X |
| 169 | Wheat 3A marker MP0192 KASP primer Allele-specific forward primer Y |
| 170 | Wheat 3A marker MP0192 KASP reverse primer |
| 171 | Wheat 3A marker MP0201 KASP primer Allele-specific forward primer X |
| 172 | Wheat 3A marker MP0201 KASP primer Allele-specific forward primer Y |
| 173 | Wheat 3A marker MP0201 KASP reverse primer |
| 174 | Wheat 3D marker MP0126 KASP primer Allele-specific forward primer X |
| 175 | Wheat 3D marker MP0126 KASP primer Allele-specific forward primer Y |
| 176 | Wheat 3D marker MP0126 KASP reverse primer |
| 177 | Wheat 3D marker MP0127 KASP primer Allele-specific forward primer X |
| 178 | Wheat 3D marker MP0127 KASP primer Allele-specific forward primer Y |
| 179 | Wheat 3D marker MP0127 KASP reverse primer |
| 180 | Wheat 3D marker MP0130 KASP primer Allele-specific forward primer X |
| 181 | Wheat 3D marker MP0130 KASP primer Allele-specific forward primer Y |
| 182 | Wheat 3D marker MP0130 KASP reverse primer |
| 183 | Wheat 3D marker MP0131 KASP primer Allele-specific forward primer X |
| 184 | Wheat 3D marker MP0131 KASP primer Allele-specific forward primer Y |
| 185 | Wheat 3D marker MP0131 KASP reverse primer |
| 186 | Wheat 3D marker MP0211 KASP primer Allele-specific forward primer X |
| 187 | Wheat 3D marker MP0211 KASP primer Allele-specific forward primer Y |
| 188 | Wheat 3D marker MP0211 KASP reverse primer |
| 189 | Wheat 3D marker MP0212 KASP primer Allele-specific forward primer X |
| 190 | Wheat 3D marker MP0212 KASP primer Allele-specific forward primer Y |
| 191 | Wheat 3D marker MP0212 KASP reverse primer |
| 192 | Wheat 3D marker MP0215 KASP primer Allele-specific forward primer X |
| 193 | Wheat 3D marker MP0215 KASP primer Allele-specific forward primer Y |
| 194 | Wheat 3D marker MP0215 KASP reverse primer |

TABLE 1-continued

Summary of SEQ ID NOS:

| SEQ ID NO: | Description |
|---|---|
| 195 | Wheat 3D marker MP0216 KASP primer Allele-specific forward primer X |
| 196 | Wheat 3D marker MP0216 KASP primer Allele-specific forward primer Y |
| 197 | Wheat 3D marker MP0216 KASP reverse primer |
| 198 | Synthesized Ms5 3A genomic (exon-intron) (Example 11) |
| 199 | Wheat Ms5 B genomic 2 (exon-intron) |
| 200 | Wheat Ms5 B promoter2 |
| 201 | Wheat Ms5 B terminator2 |
| 202 | Wheat U6 polIII promoter |
| 203 | Bar gene RbcsT terminator fusion |
| 204 | gRNA scaffold |
| 205 | Maize ubiquitin promoter |
| 206 | Rice codon-optimised Cas9 gene |
| 207 | *Sorghum bicolor* actin terminator |
| 208 | CaMV 35S enhancer |
| 209 | LTP2 promoter |
| 210 | DsRed2(Alt1) gene |
| 211 | PINII terminator |
| 212 | Maize Ubiquitin 1 promoter with modified first intron |

An isolated Ms1 polynucleotide comprising: (i) a nucleic acid sequence encoding a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the amino acid sequence of SEQ ID NO: 4, 9, or 14; or (ii) a full complement of the nucleic acid sequence of (i), wherein the full complement and the nucleic acid sequence of (i) consist of the same number of nucleotides and are 100% complementary.

An isolated Ms1 polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the amino acid sequence of SEQ ID NO: 4, 9, or 14.

An isolated Ms1 polynucleotide comprising (i) a nucleic acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the nucleic acid sequence of SEQ ID NO: 1-3, 5-8, 10-13, and 15 and combinations thereof; or (ii) a full complement of the nucleic acid sequence of (i).

An isolated Ms1 polynucleotide comprising a nucleotide sequence, wherein the nucleotide sequence is hybridizable under stringent conditions with a DNA molecule comprising the full complement of SEQ ID NO: 1-3, 5-8, 10-13, and 15. The isolated MS1 protein of the present disclosure may also be a protein which is encoded by a nucleic acid comprising a nucleotide sequence hybridizable under stringent conditions with the complementary strand of the nucleotide sequence of SEQ ID NO:1, 3, 6, or 8.

An isolated Ms1 polynucleotide comprising a nucleotide sequence, wherein the nucleotide sequence is derived from SEQ ID NO: 1-3, 5-8, 10-13, and 15 by alteration of one or more nucleotides by at least one method selected from the group consisting of: deletion, substitution, addition and insertion.

An isolated Ms1 polynucleotide comprising a nucleotide sequence, wherein the nucleotide sequence corresponds to an allele of SEQ ID NO: 1-3, 5-8, 10-13, and 15.

As used herein, "TaLTPG2" is used interchangeably with "Ms5". See, for example, Example 7 herein. An isolated Ms5 polynucleotide comprising: (i) a nucleic acid sequence encoding a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the amino acid sequence of SEQ ID NO: 19, 25-26, 33-34, 39, 44, 49, or 54; or (ii) a full complement of the nucleic acid sequence of (i), wherein the full complement and the nucleic acid sequence of (i) consist of the same number of nucleotides and are 100% complementary.

An isolated Ms5 polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the amino acid sequence of SEQ ID NO: 19, 25-26, 33-34, 39, 44, 49, or 54.

An isolated Ms5 polynucleotide comprising (i) a nucleic acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity when aligned with the nucleic acid sequence of SEQ ID NO: 16-18, 20-24, 27, 32, 35-38, 40-43, 45-48, 50-53, 55, or 199-201 and combinations thereof; or (ii) a full complement of the nucleic acid sequence of (i).

An isolated Ms5 polynucleotide comprising a nucleotide sequence, wherein the nucleotide sequence is hybridizable under stringent conditions with a DNA molecule comprising the full complement of SEQ ID NO: 16-18, 20-24, 27, 32, 35-38, 40-43, 45-48, 50-53, 55, or 199-201. The isolated MS5 protein of the present disclosure may also be a protein which is encoded by a nucleic acid comprising a nucleotide sequence hybridizable under stringent conditions with the complementary strand of the nucleotide sequence of SEQ ID NO: 16-18, 20-24, 27, 32, 35-38, 40-43, 45-48, 50-53, 55, or 199-201.

An isolated Ms5 polynucleotide comprising a nucleotide sequence, wherein the nucleotide sequence is derived from SEQ ID NO: 16-18, 20-24, 27, 32, 35-38, 40-43, 45-48, 50-53, 55, or 199-201 by alteration of one or more nucleotides by at least one method selected from the group consisting of: deletion, substitution, addition and insertion.

Any of the Ms1 or Ms5 polynucleotides and polypeptide described herein and known in the art may be utilized in any methods and compositions of the present disclosure.

Because the genetic modification is introduced at a target site located in or near a male fertility gene of Ms1 or Ms5, it is not necessary to screen a population of thousands of plants carrying random mutations, such as those resulting from chemical mutagenesis, in order to identify a plant with the introduced genetic modification. Therefore, the need to backcross a plant to remove undesired mutations that are not the introduced genetic modification is eliminated or at least reduced.

Described herein are compositions and methods for producing male-sterile plants that introduce a genetic modification into a male fertility gene locus of Ms1 or Ms5 in the plant genome in a plant cell and obtaining a plant from that plant cell. The methods may employ a guide RNA/Cas endonuclease system, wherein the Cas endonuclease is guided by the guide RNA to recognize and optionally introduce a double strand break at a specific target site into the genome of a cell. The guide RNA/Cas endonuclease system provides for an effective system for modifying target sites within the genome of a plant, plant cell or seed. The target site recognized by a Cas endonuclease may be located within or outside the Ms1 or Ms5 ponucleotide sequence, for example, within or outside the Ms1 or Ms5 gene locus.

In one embodiment, the method comprises a method for producing a male-sterile plant, the method comprising: a) obtaining a first plant comprising at least one Cas endonuclease capable of introducing a double strand break at a genomic target site located in a male fertility gene locus of Ms1 or Ms5 in the plant genome; b) obtaining a second plant comprising a guide RNA that is capable of forming a complex with the Cas endonuclease of (a),c) crossing the first plant of (a) with the second plant of (b); d) evaluating the progeny of (c) for an alteration in the target site; and e) selecting a progeny plant that is male-sterile.

Compositions and methods are also provided for editing a nucleotide sequence in the genome of a cell. In one embodiment, the disclosure describes a method for editing a nucleotide sequence located in or near a male fertility gene of Ms1 or Ms5 in the genome of a plant cell, the method comprising providing a guide RNA, a polynucleotide modification template, and at least one maize optimized Cas9 endonuclease to a plant cell, wherein the maize optimized Cas9 endonuclease is capable of introducing a double-strand break at a target site in the plant genome, wherein said polynucleotide modification template includes at least one nucleotide modification of said nucleotide sequence. The nucleotide to be edited (the nucleotide sequence of interest) can be located within or outside a target site located in or near a male fertility gene of Ms1 or Ms5 that is recognized and cleaved by a Cas endonuclease. Cells include, but are not limited to, plant cells as well as plants and seeds produced by the methods described herein.

Compositions and methods are also provided for methods of modifying the male-fertility of a plant, the method comprising introducing at least one guide RNA, at least one polynucleotide modification template and at least one Cas endonuclease into a cell. The Cas endonuclease introduces a double-strand break at a target site located in or near a Ms1 or Ms5 gene in the genome of said plant cell and the polynucleotide modification template comprises at least one nucleotide modification of a nucleotide sequence at the target site located in or near a male fertility gene of Ms1 or Ms5 that decreases the expression level of the Ms1 or Ms5 gene, to produce a male-sterile plant.

In another embodiment, the methods include selecting a male-sterile plant, the method comprising selecting at least one male-sterile plant that comprises the introduced genetic modification(s) in at least one or more of the endogenous Ms1 or Ms5 polynucleotide sequences or Ms1 or Ms5 gene locus. Also provided is a plant cell or plant or seed obtained or produced from the methods described herein.

The plant in the embodiments described herein is a monocot or a dicot. More specifically, the monocot is selected from the group consisting of maize, rice, sorghum, rye, barley, wheat, millet, oats, sugarcane, turfgrass, or switchgrass. The dicot is selected from the group consisting of soybean, canola, alfalfa, sunflower, cotton, tobacco, peanut, potato, tobacco, Arabidopsis, or safflower.

CRISPR loci (Clustered Regularly Interspaced Short Palindromic Repeats) (also known as SPIDRs—SPacer Interspersed Direct Repeats) constitute a family of recently described DNA loci. CRISPR loci consist of short and highly conserved DNA repeats (typically 24 to 40 bp, repeated from 1 to 140 times—also referred to as CRISPR-repeats) which are partially palindromic. The repeated sequences (usually specific to a species) are interspaced by variable sequences of constant length (typically 20 to 58 by depending on the CRISPR locus (WO2007/025097 published Mar. 1, 2007).

A Cas gene includes a gene that is generally coupled, associated or close to or in the vicinity of flanking CRISPR loci. The terms "Cas gene", "CRISPR-associated (Cas) gene" are used interchangeably herein. A comprehensive review of the Cas protein family is presented in Haft et al. (2005) Computational Biology, PLoS Comput Biol 1(6): e60. doi:10.1371/journal.pcbi.0010060.

Cas endonuclease relates to a Cas protein encoded by a Cas gene, wherein said Cas protein is capable of introducing a double strand break into a DNA target sequence. The Cas endonuclease is guided by the guide polynucleotide to recognize and optionally introduce a double strand break at a specific target site into the genome of a cell. As used herein, the tem "guide polynucleotide/Cas endonuclease system" includes a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide RNA, but only if the correct protospacer-adjacent motif (PAM) is approximately oriented at the 3' end of the target sequence.

In one embodiment, the Cas endonuclease gene is a Cas9 endonuclease, such as but not limited to, Cas9 genes listed in SEQ ID NOs: 462, 474, 489, 494, 499, 505, and 518 of WO2007/025097 published Mar. 1, 2007, and incorporated herein by reference. In another embodiment, the Cas endonuclease gene is plant optimized Cas9 endonuclease, for example, codon-optimized for expression in maize, wheat, or soybean. In another embodiment, the Cas endonuclease gene is operably linked to a SV40 nuclear targeting signal upstream of the Cas codon region and a bipartite VirD2 nuclear localization signal (Tinland et al. (1992) Proc. Natl. Acad. Sci. USA 89:7442-6) downstream of the Cas codon region. As used herein, "operably linked" is intended to mean a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous. When used to refer to the joining of two protein coding regions, operably linked means that the coding regions are in the same reading frame. In one embodiment, the Cas endonuclease gene is a Cas9 endonuclease gene of SEQ ID NO:1, 124, 212, 213, 214, 215, 216, 193 or nucleotides 2037-6329 of SEQ ID NO:5, or any functional fragment or variant thereof of US publication number 20160208272, published Jul. 26, 2016, and incorporated herein by reference.

The terms "functional fragment", "fragment that is functionally equivalent" and "functionally equivalent fragment" are used interchangeably herein. These terms refer to a portion or subsequence of the polypeptide sequence of the present disclosure in which the polypeptide's native function is retained.

The terms "functional variant", "Variant that is functionally equivalent" and "functionally equivalent variant" are used interchangeably herein. These terms refer to a variant of a polypeptide of the present disclosure in which the polypeptide's native function is retained. Fragments and variants can be obtained via methods such as site-directed mutagenesis and synthetic construction.

The Cas endonuclease gene may be a plant codon optimized *Streptococcus pyogenes* Cas9 gene that can recognize any genomic sequence of the form N(12-30)NGG can in principle be targeted.

The Cas endonuclease may be introduced directly into a cell by any method known in the art, for example, but not limited to transient introduction methods, transfection and/or topical application, including those described in US publication number 20160208272, published Jul. 26, 2016, and incorporated herein by reference. The type II CRISPR/Cas system from bacteria employs a crRNA and tracrRNA to guide the Cas endonuclease to its DNA target. The crRNA (CRISPR RNA) contains the region complementary to one strand of the double strand DNA target and base pairs with the tracrRNA (trans-activating CRISPR RNA) forming a RNA duplex that directs the Cas endonuclease to cleave the DNA target.

As used herein, the term "guide RNA" relates to a synthetic fusion of two RNA molecules, a crRNA (CRISPR RNA) comprising a variable targeting domain, and a tracrRNA. In one embodiment, the guide RNA comprises a variable targeting domain of 12 to 30 nucleotide sequences and a RNA fragment that can interact with a Cas endonuclease.

As used herein, the term "guide polynucleotide", relates to a polynucleotide sequence that can form a complex with a Cas endonuclease and enables the Cas endonuclease to recognize and optionally cleave a DNA target site. The guide polynucleotide can be a single molecule or a double molecule. The guide polynucleotide sequence can be a RNA sequence, a DNA sequence, or a combination thereof (a RNA-DNA combination sequence). A guide polynucleotide that solely comprises ribonucleic acids is also referred to as a "guide RNA". The guide polynucleotide can be a double molecule (also referred to as duplex guide polynucleotide) comprising a first nucleotide sequence domain (referred to as Variable Targeting domain or VT domain) that is complementary to a nucleotide sequence in a target DNA and a second nucleotide sequence domain (referred to as Cas endonuclease recognition domain or CER domain) that interacts with a Cas endonuclease polypeptide. The CER domain of the double molecule guide polynucleotide comprises two separate molecules that are hybridized along a region of complementarity. The two separate molecules can be RNA, DNA, and/or RNA-DNA-combination sequences. In some embodiments, the first molecule of the duplex guide polynucleotide comprising a VT domain linked to a CER domain is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the cRNA naturally occurring in Bacteria and Archaea. In one embodiment, the size of the fragment of the cRNA naturally occurring in Bacteria and Archaea that is present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In one example, the second molecule of the duplex guide polynucleotide comprising a CER domain is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides. In one example, the RNA that guides the RNA/Cas9 endonuclease complex, is a duplexed RNA comprising a duplex crRNA-tracrRNA.

The guide polynucleotide can also be a single molecule comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. In some examples, the single guide polynucleotide comprises a crNucleotide (comprising a VT domain linked to a CER domain) linked to a tracrNucleotide (comprising a CER domain), wherein the linkage is a nucleotide sequence comprising a RNA sequence, a DNA sequence, or a RNA-DNA combination sequence. The single guide polynucleotide being comprised of sequences from the crNucleotide and tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). The single guide RNA may comprise a cRNA or cRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a plant genomic target site, enabling the Cas endonuclease to introduce a double strand break into the genomic target site. One aspect of using a single guide polynucleotide versus a duplex guide polynucleotide is that only one expression cassette needs to be made to express the single guide polynucleotide.

The term "variable targeting domain" or "VT domain" is used interchangeably herein and includes a nucleotide sequence that is complementary to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some examples, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof. The term "Cas endonuclease recognition domain" or "CER domain" of a guide polynucleotide is used interchangeably herein and includes a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one example, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another example, the nucleotide sequence linking the crNucleotide and the tracrNucleotide of a single guide polynucleotide can comprise a tetraloop sequence, such as, but not limiting to a GAAA tetraloop sequence.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

The guide RNA and Cas endonuclease are capable of forming a complex that enables the Cas endonuclease to introduce in the plant genome a double strand break at a DNA target site, for example, in a male fertility gene locus of Ms1 or Ms5 or within Ms1 or Ms5 polynucleotides themselves. The variable target domain may be 12, 13, 14, 15, 16, 17, 18, 19, 20, 21, 22, 23, 24, 25, 26, 27, 28, 29 or 30 nucleotides in length.

In some approaches, the guide RNA comprises a cRNA (or cRNA fragment) and a tracrRNA (or tracrRNA fragment) of the type II CRISPR/Cas system that can form a complex with a type II Cas endonuclease, wherein said guide RNA/Cas endonuclease complex can direct the Cas endonuclease to a plant genomic target site, enabling the Cas endonuclease to introduce a double strand break into the genomic target site.

The guide RNA can be introduced into a plant or plant cell directly using any method known in the art such as, but not limited to, particle bombardment or topical applications, for example, as described in US publication number 20160208272, published Jul. 26, 2016, and incorporated herein by reference.

The guide RNA may be introduced indirectly by introducing a recombinant DNA molecule comprising the corresponding guide DNA sequence operably linked to a plant specific promoter that is capable of transcribing the guide RNA in said plant cell. The term "corresponding guide DNA" includes a DNA molecule that is identical to the RNA molecule but has a "T" substituted for each "U" of the RNA molecule. The guide RNA may be introduced via particle bombardment or *Agrobacterium* transformation of a recombinant DNA construct comprising the corresponding guide DNA operably linked to a plant U6 polymerase III promoter.

The RNA that guides the RNA/Cas9 endonuclease complex, may be a duplexed RNA comprising a duplex crRNA-tracrRNA. One advantage of using a guide RNA versus a duplexed crRNA-tracrRNA is that only one expression cassette needs to be made to express the fused guide RNA.

The terms "target site", "target sequence", "target DNA", "target locus", "genomic target site", "genomic target sequence", and "genomic target locus" are used interchangeably herein and refer to a polynucleotide sequence in the genome (including choroloplastic and mitochondrial DNA) of a plant cell at which a double-strand break is induced in the plant cell genome by a Cas endonuclease. The target site can be an endogenous site in the plant genome, or alternatively, the target site can be heterologous to the plant and thereby not be naturally occurring in the genome, or the target site can be found in a heterologous genomic location compared to where it occurs in nature. As used herein, terms "endogenous target sequence" and "native target sequence" are used interchangeable herein to refer to a target sequence that is endogenous or native to the genome of a plant and is at the endogenous or native position of that target sequence in the genome of the plant.

The target site may be similar to a DNA recognition site or target site that that is specifically recognized and/or bound by a double-strand break inducing agent such as a LIG3-4 endonuclease (US patent publication 2009-0133152 A1 (published May 21, 2009) or a meganuclease (U.S. patent publication 20150184194 published Jul. 2, 2015).

An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii). For example, the methods and compositions described herein may be used to produce a Ms1 or Ms5 modified target site which confers male-sterility to the plant containing the modified Ms1 or Ms5 target site or introduced genetic modification.

Methods for modifying a plant genomic target site are disclosed herein.

In another embodiment, the method includes modifying a target site located in or near a Ms1 or Ms5 gene in the genome of a plant cell, the method comprising introducing a guide RNA into a plant cell having a Cas endonuclease, wherein said guide RNA and Cas endonuclease are capable of forming a complex that enables the Cas endonuclease to introduce a double strand break at said target site.

Also provided is a method for modifying a target site in the genome of a plant cell, the method comprising introducing a guide RNA and a Cas endonuclease into said plant, wherein said guide RNA and Cas endonuclease are capable of forming a complex that enables the Cas endonuclease to introduce a double strand break at said target site. In some embodiments, the guideRNA can simultaneously modify the same target site in multiple genomes in the plant cell or plant. See, for example, Example 3, demonstrating the generation of ms1 mutations in the b genome in wheat using Cas9 technology. Table 2 provided herein shows exemplary DNA versions of wheat guideRNAs and target sequences for making Ms1 or Ms5 mutations in wheat genomes to confer male-sterility to a plant. Additionally, many of the target sequences listed for wheat are consensus sequences so that each genome (A, B, or D) can be modified simultaneously using the same guideRNA to produce the genetic modification. For example, the target sequences of SEQ ID NOs:57-59, 61-64, and 67-81 shown in Table 2 were selected as each site is a consensus region found in all three (A, B, and D) genomes in wheat. In some embodiments, only one genome in wheat is targeted, see, for example, SEQ ID NOs: 56, 60, and 65-66 specifically targeting the wheat B genome. As shown in Example 3 herein, targeting the B genome alone is sufficient to cause male-sterility of the wheat plant.

Further provided is a method for modifying a target site in or near a Ms1 or Ms5 gene in the genome of a plant cell, the method comprising: a) introducing into a plant cell a guide RNA comprising a variable targeting domain and a Cas endonuclease, wherein said guide RNA and Cas endonuclease are capable of forming a complex that enables the Cas endonuclease to introduce a double strand break at said target site; and, b) identifying at least one plant cell that has a modification at said target, wherein the modification includes at least one deletion or substitution of one or more nucleotides in said target site. A plant derived the modified plant cell is male-sterile.

Further provided, a method for modifying a target DNA sequence in or near a Ms1 or Ms5 gene in the genome of a plant cell, the method comprising: a) introducing into a plant cell a first recombinant DNA construct capable of expressing a guide RNA and a second recombinant DNA construct capable of expressing a Cas endonuclease, wherein said guide RNA and Cas endonuclease are capable of forming a complex that enables the Cas endonuclease to introduce a double strand break at said target site; and, b) identifying at least one plant cell that has a modification at said target, wherein the modification includes at least one deletion or substitution of one or more nucleotides in said target site and the modification confers male-sterility to a plant derived from the modified plant cell.

The length of the target site can vary, and includes, for example, target sites that are at least 12, 13, 14, 15, 16, 17, 18, 19, 20, 21, 22, 23, 24, 25, 26, 27, 28, 29, 30 or more nucleotides in length. It is further possible that the target site can be palindromic, that is, the sequence on one strand reads the same in the opposite direction on the complementary strand. The nick/cleavage site can be within the target sequence or the nick/cleavage site could be outside of the target sequence. In another variation, the cleavage could occur at nucleotide positions immediately opposite each other to produce a blunt end cut or, in other Cases, the incisions could be staggered to produce single-stranded overhangs, also called "sticky ends", which can be either 5' overhangs, or 3' overhangs.

In some embodiment, the genomic target site capable of being cleaved by a Cas endonuclease comprises a 12 to 30 nucleotide fragment of a male fertility gene. Exemplary male fertility genes for use in the compositions and methods described here include but are not limited to MS1 or MS5. In some embodiments, the MS1 or MS5 fertility genes or gene loci to be targeted are from wheat, barley, maize, rice, sorghum, rye, millet, oats, sugarcane, turfgrass, switchgrass, soybean, canola, alfalfa, sunflower, cotton, tobacco, peanut, potato, tobacco, *Arabidopsis*, or safflower.

TABLE 2

Exemplary Guide RNAs and Target Sequence Description

| Target Sequence Designation | Target Sequence (5'-3') and target strand | Start Position (bp) | Relative End Position (bp) | Relative DSB Position (bp) | PAM Sequence | DNA version of Guide RNA | Target Site |
|---|---|---|---|---|---|---|---|
| Wheat Ms1 CR1 | CGCCACCAGCAGCAGC CCGCGG- complementary (SEQ ID NO: 56) | Position 12 of SEQ ID NO: 6 | Position 33 of SEQ ID NO: 6 | Between Position 17 and 18 of SEQ ID NO: 6 | CGG | CGCCACCAGCAGCAGC CCG (SEQ ID NO: 82) | Exon 1 |
| Wheat Ms1 CR2 | GGGCGGGGGGCTGCTGA CGACGG- Complementary (SEQ ID NO: 57) | Position 1416 of SEQ ID NO: 6 | Position 1438 of SEQ ID NO: 6 | Between Position 1421 and 1422 of SEQ ID NO: 6 | CGG | GGGCGGGGGGCTGCTG ACGA (SEQ ID NO: 83) | Exon 2 |
| Wheat Ms1 CR3 | GTCGTCCCCGCCGCCGT CCCAGG- Sense (SEQ ID NO: 58) | Position 1646 of SEQ ID NO: 6 | Position 1668 of SEQ ID NO: 6 | Between Position 1662 and 1663 of SEQ ID NO: 6 | AGG | GTCGTCCCCGCCGCCG TCCC (SEQ ID NO: 84) | Exon 3 |
| Wheat Ms1 CR4 | GACGAAGAAGAAGGCCG CCTTGG- Complementary (SEQ ID NO: 59) | Position 1798 of SEQ ID NO: 6 | Position 1820 of SEQ ID NO: 6 | Between Position 1803 and 1804 of SEQ ID NO: 6 | TGG | GACGAAGAAGAAGGCC GCCT (SEQ ID NO: 85) | Exon 3 |
| Wheat Ms1 CR5 | GCCCACGGCGCCGTCCA AGGCGG- Sense (SEQ ID NO: 60) | Position 1784 of SEQ ID NO: 6 | Position 1806 of SEQ ID NO: 6 | Between Position 1800 and 1801 of SEQ ID NO: 6 | CGG | GCCCACGGCGCCGTCC AAGG (SEQ ID NO: 86) | Exon 3 |
| Wheat Ms1 CR6 | GGCCGTGGCGACGAAGA AGAAGG- Complementary (SEQ ID NO: 61) | Position 1807 of SEQ ID NO: 6 | Position 1829 of SEQ ID NO: 6 | Between Position 1812 and 1813 of SEQ ID NO: 6 | AGG | GGCCGTGGCGACGAAG AAGA (SEQ ID NO: 87) | Exon 3 |
| Wheat Ms1 | GTAGAGGCCGAGCATGG | Position | Position | Between | TGG | GTAGAGGCCGAGCATG | Exon 3 |

TABLE 2-continued

Exemplary Guide RNAs and Target Sequence Description

| | | | | | | |
|---|---|---|---|---|---|---|
| CR7 | CCGTGG-<br>Complementary<br>(SEQ ID NO: 62) | 1822 of<br>SEQ ID<br>NO: 6 | 1844 of SEQ<br>ID NO: 6 | Position<br>1827 and<br>1828 of SEQ<br>ID NO: 6 | | GCCG<br>(SEQ ID NO: 88) |
| Wheat Ms1<br>CR8 | GGCCTTCTTCTTCGTCG<br>CCACGG-<br>Sense<br>(SEQ ID NO: 63) | Position<br>1805 of<br>SEQ ID<br>NO: 6 | Position<br>1827 of SEQ<br>ID NO: 6 | Between<br>Position<br>1821 and<br>1822 of SEQ<br>ID NO: 6 | CGG | GGCCTTCTTCTTCGTC Exon 3<br>GCCA<br>(SEQ ID NO: 89) |
| Wheat Ms1<br>CR9 | GATGATGTAGAGGCCGA<br>GCATGG-<br>Complementary<br>(SEQ ID NO: 64) | Position<br>1828 of<br>SEQ ID<br>NO: 6 | Position<br>1850 of SEQ<br>ID NO: 6 | Between<br>Position<br>1833 and<br>1834 of SEQ<br>ID NO: 6 | TGG | GATGATGTAGAGGCCG Exon 3<br>AGCA<br>(SEQ ID NO: 90) |
| Wheat Ms1<br>CR10 | GAGATCCCGCGGGCTGC<br>TGCTGG-<br>sense<br>(SEQ ID NO: 65) | Position 6<br>of SEQ ID<br>NO: 6 | Position 28<br>of SEQ ID<br>NO: 6 | Between<br>Position 22<br>and 23 of<br>SEQ ID NO: 6 | TGG | (SEQ ID NO: 92) Exon1<br>GAGATCCCGCGGGCTG<br>CTGC<br>(SEQ ID NO: 91) |
| Wheat Ms1<br>CR11 | GCTGCTGGCGGCGCTGC<br>TGCCGG-<br>sense<br>(SEQ ID NO: 66) | Position<br>36 of<br>SEQ ID<br>NO: 6 | Position 58<br>of SEQ ID<br>NO: 6 | Between<br>Position 52<br>and 53 of<br>SEQ ID NO: 6 | CGG | GCTGCTGGCGGCGCTG Exon 1<br>CTGC<br>(SEQ ID NO: 92) |

| Target<br>Sequence<br>Designation | Target Sequence<br>(5'-3')<br>and target strand | Start<br>Position<br>(bp) | Relative End<br>Position (bp) | Start and<br>End<br>Positions of<br>Target<br>Sequence | PAM<br>Sequence | DNA version of<br>Guide RNA | Target<br>Site |
|---|---|---|---|---|---|---|---|
| Wheat Ms5<br>CR1 | GCACGGCGAGAAGGAC<br>ACGATGG-<br>Complementary<br>(SEQ ID NO: 67) | 110 | 132 | Position<br>relative to<br>ATG in SEQ<br>ID NO: 16 | TGG | GCACGGCGAGAAGGAC<br>ACGA<br>(SEQ ID NO: 93) | Exon 1 |
| Wheat Ms5<br>CR2 | GCAGCAGGCGCTGGTGG<br>GCGCGG-<br>Complementary<br>(SEQ ID NO: 68) | 176 | 198 | Position<br>relative to<br>ATG in SEQ<br>ID NO: 16 | CGG | GCAGCAGGCGCTGGTG<br>GGCG<br>(SEQ ID NO: 94) | Exon 1 |
| Wheat Ms5<br>CR3 | GCCGCGCAGCAGGCGCT<br>GGTGGG-<br>Complementary<br>(SEQ ID NO: 69) | 181 | 203 | Position<br>relative to<br>ATG in SEQ<br>ID NO: 16 | GGG | GCCGCGCAGCAGGCGC<br>TGGT<br>(SEQ ID NO: 95) | Exon 1 |
| Wheat Ms5<br>CR4 | GAACGCCGCGCAGCAGG<br>CGCTGG-<br>Complementary<br>(SEQ ID NO: 70) | 185 | 207 | Position<br>relative to<br>ATG in SEQ<br>ID NO: 16 | TGG | GAACGCCGCGCAGCAG<br>GCGC<br>(SEQ ID NO: 96) | Exon 1 |
| Wheat Ms5<br>CR5 | GCGCAGGAACGCCGCGC<br>AGCAGG-<br>Complementary<br>(SEQ ID NO: 71) | 191 | 203 | Position<br>relative to<br>ATG in SEQ<br>ID NO: 16 | AGG | GCGCAGGAACGCCGCG<br>CAGC<br>(SEQ ID NO: 97) | Exon 1 |
| Wheat Ms5<br>CR6 | GCCCACCAGCGCCTGCT<br>GCGCGG-<br>Sense<br>(SEQ ID NO: 72) | 180 | 202 | Position<br>relative to<br>ATG in SEQ<br>ID NO: 16 | CGG | GCCCACCAGCGCCTGC<br>TGCG<br>(SEQ ID NO: 98) | Exon 1 |
| Wheat Ms5<br>CR7 | GCCGCCTTCGCCGTCCC<br>CGGAGG-<br>Complementary<br>(SEQ ID NO: 73) | 221 | 243 | Position<br>relative to<br>ATG in SEQ<br>ID NO: 16 | AGG | GCCGCCTTCGCCGTCC<br>CCGG<br>(SEQ ID NO: 99) | Exon 1 |
| Wheat Ms5<br>CR8 | GGGGACGGCGAAGGCGG<br>CGGAGG-<br>Sense<br>(SEQ ID NO: 74) | 226 | 248 | Position<br>relative to<br>ATG in SEQ<br>ID NO: 16 | AGG | GGGGACGGCGAAGGCG<br>GCGG<br>(SEQ ID NO: 100) | Exon 1 |
| Wheat Ms5<br>CR9 | GGGACGGCGAAGGCGGC<br>GGAGGG-<br>Sense<br>(SEQ ID NO: 75) | 227 | 249 | Position<br>relative to<br>ATG in SEQ<br>ID NO: 16 | GGG | GGGACGGCGAAGGCGG<br>CGGA<br>(SEQ ID NO: 101) | Exon 1 |

TABLE 2-continued

Exemplary Guide RNAs and Target Sequence Description

| Wheat Ms5 CR10 | GGACGGCGAAGGCGGCG GAGGGG- Sense (SEQ ID NO: 76) | 228 | 250 | Position relative to ATG in SEQ ID NO: 16 | GGG | GGACGGCGAAGGCGGC GGAG (SEQ ID NO: 102) | Exon 1 |
|---|---|---|---|---|---|---|---|
| Wheat Ms5 CR11 | GGCGAAGGCGGCGGAGG GGAGGG- Sense (SEQ ID NO: 77) | 232 | 254 | Position relative to ATG in SEQ ID NO: 16 | GGG | GGCGAAGGCGGCGGAG GGGA (SEQ ID NO: 103) | Exon 1 |
| Wheat Ms5 CR12 | GCCGAGGCGCGCGGCGT CGACGG- Complementary (SEQ ID NO: 78) | 299 | 321 | Position relative to ATG in SEQ ID NO: 16 | CGG | GCCGAGGCGCGCGGCG TCGA (SEQ ID NO: 104) | Exon 1 |
| Wheat Ms5 CR13 | GTTTTCGCGGAGGCGCA GGTGGG- Complementary (SEQ ID NO: 79) | 331 | 353 | Position relative to ATG in SEQ ID NO: 16 | GGG | GTTTTCGCGGAGGCGC AGGT (SEQ ID NO: 105) | Exon 1 |
| Wheat Ms5 CR14 | GGTTTTCGCGGAGGCGC AGGTGG- Complementary (SEQ ID NO: 80) | 332 | 354 | Position relative to ATG in SEQ ID NO: 16 | TGG | GGTTTTCGCGGAGGCG CAGG (SEQ ID NO: 106) | Exon 1 |
| Wheat Ms5 CR15 | GGAGGTTTTCGCGGAGG CGCAGG- Complementary (SEQ ID NO: 81) | 335 | 357 | Position relative to ATG in SEQ ID NO: 16 | AGG | GGAGGTTTTCGCGGAG GCGC (SEQ ID NO: 107) | Exon 1 |

TABLE 3

Description of resulting MS1 genome edits

| Target Sequence (5'-3') and target strand | DNA version of Guide RNA | Target Site | Description of Edit |
|---|---|---|---|
| CGCCACCAGCAGCAGCCCGCGG- complementary (SEQ ID NO: 56) | CGCCACCAGCAGCAGCCCG (SEQ ID NO: 82) | Exon 1 | Exon 1 Insertion of one nucleotide (A) at position 18 of MS1 CDS (SEQ ID NO: 8) (by single guide RNA (SEQ ID NO: 82) CGCCACCAGCAGCAGCACCG (SEQ ID NO: 108) |
| CGCCACCAGCAGCAGCCCGCGG- complementary (SEQ ID NO: 56) | CGCCACCAGCAGCAGCCCG (SEQ ID NO: 82) | Exon 1 | Exon 1 Insertion of one nucleotide (T) at position 18 of MS1 CDS (SEQ ID NO: 8) (by single guide RNA; (SEQ ID NO: 82) CGCCACCAGCAGCAGCTCCG (SEQ ID NO: 109) |
| CGCCACCAGCAGCAGCCCGCGG- complementary (SEQ ID NO: 56) | CGCCACCAGCAGCAGCCCG (SEQ ID NO: 82) | Exon 1 | Exon 1 Insertion of one nucleotide (C) at position 18 of MS1 CDS (SEQ ID NO: 8) (by single guide RNA; (SEQ ID NO: 82) CGCCACCAGCAGCAGCCCCG (SEQ ID NO: 110) |
| CGCCACCAGCAGCAGCCCGCGG- complementary (SEQ ID NO: 56) | CGCCACCAGCAGCAGCCCG (SEQ ID NO: 82) | Exon 1 | Exon 1 Deletion of 3 nucleotide at position 18 of MS1 CDS (SEQ ID NO:8) (by single guide RNA; (SEQ ID NO: 82) CGCCACCAGCAGCCCG (SEQ ID NO: 111) |

Active variants of genomic target sites can also be used. Such active variants can comprise at least 65%, 70%, 75%, 80%, 85%, 90%, 91%, 92%, 93%, 94%, 95%, 96%, 97%, 98%, 99% or more sequence identity to the given target site, wherein the active variants retain biological activity and hence are capable of being recognized and cleaved by a Cas endonuclease. Assays to measure the double-strand break of a target site by an endonuclease are known in the art and generally measure the overall activity and specificity of the agent on DNA substrates containing recognition sites.

As used herein, a "genomic region" is a segment of a chromosome in the genome of a plant cell. The genomic region may be present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

The structural similarity between a given genomic region and the corresponding region of homology found on the donor DNA can be any degree of sequence identity that allows for homologous recombination to occur. For example, the amount of homology or sequence identity shared by the "region of homology" of the donor DNA and the "genomic region" of the plant genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination The region of homology on the donor DNA can have homology to any sequence flanking the target site. While in some embodiments the regions of homology share significant sequence homology to the genomic sequence immediately flanking the target site, it is recognized that the regions of homology can be designed to have sufficient homology to regions that may be further 5' or 3' to the target site. In still other embodiments, the regions of homology can also have homology with a fragment of the target site along with downstream genomic regions. In one embodiment, the first region of homology further comprises a first fragment of the target site and the second region of homology comprises a second fragment of the target site, wherein the first and second fragments are dissimilar. As used herein, "homologous recombination" includes the exchange of DNA fragments between two DNA molecules at the sites of homology. Homology-directed repair (HDR) is a mechanism in cells to repair double-stranded and single stranded DNA breaks. Homology-directed repair includes homologous recombination (HR) and single-strand annealing (SSA) (Lieber. 2010 Annu. Rev. Biochem 79:181-211). The most common form of HDR is called homologous recombination (HR), which has the longest sequence homology requirements between the donor and acceptor DNA. Other forms of HDR include single-stranded annealing (SSA) and breakage-induced replication, and these require shorter sequence homology relative to HR. Homology-directed repair at nicks (single-stranded breaks) can occur via a mechanism distinct from HDR at double-strand breaks (Davis and Maizels. PNAS (0027-8424), 111 (10), p. E924-E932.

Alteration of the genome of a plant cell, for example, through homologous recombination (HR), is a powerful tool for genetic engineering. Despite the low frequency of homologous recombination in higher plants, there are a few examples of successful homologous recombination of plant endogenous genes. The parameters for homologous recombination in plants have primarily been investigated by rescuing introduced truncated selectable marker genes. In these experiments, the homologous DNA fragments were typically between 0.3 kb to 2 kb. Observed frequencies for homologous recombination were on the order of $10^{-4}$ to $10^{-5}$. See, for example, Halfter et al., (1992) Mol Gen Genet 231:186-93; Offringa et al., (1990) EMBO J 9:3077-84; Offringa et al., (1993) Proc. Natl. Acad. Sci. USA 90:7346-50; Paszkowski et al., (1988) EMBO J 7:4021-6; Hourda and Paszkowski, (1994) Mol Gen Genet 243:106-11; and Risseeuw et al., (1995) Plant J 7:109-19. Once a double-strand break is induced in the DNA, the cell's DNA repair mechanism is activated to repair the break. Error-prone DNA repair mechanisms can produce mutations at double-strand break sites. The most common repair mechanism to bring the broken ends together is the nonhomologous end-joining (NHEJ) pathway (Bleuyard et al., (2006) DNA Repair 5:1-12). The structural integrity of chromosomes is typically preserved by the repair, but deletions, insertions, or other rearrangements are possible (Siebert and Puchta, (2002) Plant Cell 14:1121-31; Pacher et al., (2007) Genetics 175:21-9). Alternatively, the double-strand break can be repaired by homologous recombination between homologous DNA sequences.

Genome Editing Using the Guide RNA/Cas Endonuclease System

Further provided is a method for modifying a target site at or near a Ms1 or Ms5 gene in the genome of a plant cell, the method comprising introducing a guide RNA and a donor DNA into a plant cell having a Cas endonuclease, wherein said guide RNA and Cas endonuclease are capable of forming a complex that enables the Cas endonuclease to introduce a double strand break at said target site, wherein said donor DNA comprises a polynucleotide of interest that when inserted confers male-sterility to a plant obtained from the modified plant cell.

As described herein, the guide RNA/Cas endonuclease system can be used in combination with a co-delivered polynucleotide modification template to allow for editing of a genomic nucleotide sequence of interest, Ms1 or Ms5, to confer male-sterility to a plant. Also, as described herein, for each embodiment that uses a guide RNA/Cas endonuclease system, a similar guide polynucleotide/Cas endonuclease system can be deployed where the guide polynucleotide does not solely comprise ribonucleic acids but wherein the guide polynucleotide comprises a combination of RNA-DNA molecules or solely comprise DNA molecules.

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

In one embodiment provided herein, the method comprises contacting a plant cell with the donor DNA and the endonuclease. Once a double-strand break is introduced in the target site by the endonuclease, the first and second regions of homology of the donor DNA can undergo homologous recombination with their corresponding genomic regions of homology resulting in exchange of DNA between the donor and the genome. As such, the provided methods result in the integration of the polynucleotide of interest of the donor DNA into the double-strand break in the target site in the plant genome so that the endogenous male fertility gene of Ms1 or Ms5 is disrupted, thereby altering the original target site and producing an altered genomic target site that confers male sterility to the plant.

The donor DNA may be introduced by any means known in the art. For example, a plant having a target site is provided. The donor DNA may be provided by any transformation method known in the art including, for example, Agrobacterium-mediated transformation or biolistic particle bombardment. The donor DNA may be present transiently in the cell or it could be introduced via a viral replicon. In the presence of the Cas endonuclease and the target site, the donor DNA is inserted into the transformed plant's genome to disrupt an endogenous male fertility gene of Ms1 or Ms5.

In one embodiment, the disclosure describes a method for editing a nucleotide sequence in the genome of a cell, the method comprising providing a guide RNA, a polynucleotide modification template, and at least one Cas endonuclease to a cell, wherein the Cas endonuclease is capable of introducing a double-strand break at a target sequence in the genome of said cell to confer male-sterility, wherein said polynucleotide modification template includes at least one nucleotide modification of said nucleotide sequence. The nucleotide to be edited can be located within or outside a target site of one or more Ms1 or Ms5 genes recognized and cleaved by a Cas endonuclease. In one embodiment, the at least one nucleotide modification is not a modification at a target site recognized and cleaved by a Cas endonuclease. In another embodiment, there are at least 1, 2, 3, 4, 5, 6, 7, 8, 9, 10, 11, 12, 13, 14, 15, 16, 17, 18, 19, 20, 21, 22, 23, 24, 25, 26, 27, 30, 40, 50, 100, 200, 300, 400, 500, 600, 700, 900 or 1000 nucleotides between the at least one nucleotide to be edited and the genomic target site.

In another embodiment of genome editing, editing of an endogenous MS1 or MS5 gene in a plant cell or plant is disclosed herein. In some embodiments, the polynucleotide modification template (male fertility gene polynucleotide modification template) includes a partial fragment of the Ms1 or Ms5 gene (and therefore does not encode a fully functional Ms1 or Ms5 polypeptide by itself).

In one embodiment of the disclosure, a wheat Ms1 or Ms5 mutant plant is produced by the method described herein, said method comprising: a) providing a guide RNA, a polynucleotide modification template and at least one Cas endonuclease to a plant cell, wherein the Cas endonuclease introduces a double strand break at a target site within a wheat Ms1 or Ms5 (male sterility 45) genomic sequence in the plant genome, wherein said polynucleotide modification template comprises at least one nucleotide modification of the Ms1 or Ms5 genomic sequence; b) obtaining a plant from the plant cell of (a); c) evaluating the plant of (b) for the presence of said at least one nucleotide modification and d) selecting a progeny plant exhibiting male sterility from the modification of the endogenous Ms1 or Ms5 gene. The nucleotide sequence to be edited may be a sequence that is endogenous to the cell that is being edited.

Regulatory Sequence Modifications Using the Guide Polynucleotide/Cas Endonuclease System In one example, the nucleotide sequence to be modified can be a regulatory sequence such as a promoter, for example, for an endogenous MS1 or MS5 gene in a plant cell or plant. In some examples, the promoter may be modified to include or remove an element in the promoter. In one embodiment, the guide polynucleotide/Cas endonuclease system can be used to allow for the deletion of a promoter or promoter element, wherein the promoter deletion (or promoter element deletion) results in any one of the following or any one combination of the following: a permanently inactivated gene locus, a decreased promoter activity, a decreased promoter tissue specificity, a modification of the timing or developmental progress of gene expression, a mutation of DNA binding elements and/or an addition of DNA binding elements. Promoter elements to be deleted can be, but are not limited to, promoter core elements, such as, but not limited to, a CAAT box, a CCAAT box, a Pribnow box, TATA box, and/or translational regulation sequences, promoter enhancer elements. The promoter or promoter fragment to be deleted may be endogenous to the cell that is being edited, for example, the promoter of an endogenous Ms1 or Ms5 fertility gene.

Additional Regulatory Sequence Modifications Using the Guide Polynucleotide/Cas Endonuclease System The guide polynucleotide/Cas endonuclease system may be used to modify or replace a regulatory sequence in the genome of a cell. A regulatory sequence is a segment of a nucleic acid molecule which is capable of increasing or decreasing the expression of specific genes within an organism and/or is capable of altering tissue specific expression of genes within an organism. Examples of regulatory sequences include, but are not limited to, 3' UTR (untranslated region) region, 5' UTR region, transcription activators, transcriptional enhancers transcriptions repressors, translational repressors, splicing factors, miRNAs, siRNA, artificial miRNAs, promoter elements, polyadenylation signals, and polyubiquitination sites. In one example, the editing (modification) or replacement of a regulatory element results in altered protein translation, RNA cleavage, RNA splicing, transcriptional termination or post translational modification that confers male-sterility to a plant. In one embodiment, regulatory elements can be identified within a promoter and these regulatory elements can be edited or modified do to optimize these regulatory elements for down regulation of the promoter to create a male sterile plant. In one embodiment, the genomic sequence of interest to be modified is an intron or UTR site, wherein the modification consist of inserting at least one microRNA into said intron or UTR site, wherein expression of the gene comprising the intron or UTR site also results in expression of said microRNA, which in turn can silence any gene targeted by the microRNA without disrupting the gene expression of the native/transgene comprising said intron.

Modifications of Splicing Sites and/or Introducing Alternate Splicing Sites Using the Guide Polynucleotide/Cas Endonuclease System The guide polynucleotide/Cas endonuclease system can be used in combination with a co-delivered polynucleotide modification template to edit an endogenous Ms1 or Ms5 gene to introduce a canonical splice site at a described junction or any variant of a splicing site that disrupts the splicing pattern of pre-mRNA molecules so that the plant with the introduced genetic modification is male-sterile.

Modifications of Nucleotide Sequences Encoding a Protein of Interest Using the Guide Polynucleotide/Cas Endonuclease System In one embodiment, the guide polynucleotide/Cas endonuclease system can be used to modify or replace a coding sequence in the fertility gene locus of Ms1 or Ms5 in the genome of a plant cell, wherein the modification or replacement results in conferring male-sterility to the plant. In one embodiment, the protein knockout is due to the introduction of a stop codon into the coding sequence of interest. In one embodiment, the protein knockout is due to the deletion of a start codon into the coding sequence of interest.

Gene Silencing by Expressing an Inverted Repeat or Antisense Using the Guide Polynucleotide/Cas Endonuclease System In one embodiment, the guide polynucleotide/Cas endonuclease system can be used in combination with a co-delivered polynucleotide sequence to insert an inverted gene fragment into a gene of interest in the genome of an organism, wherein the insertion of the inverted gene fragment can allow for an in-vivo creation of an inverted repeat (hairpin) and results in the silencing of said endogenous gene of Ms1 or Ms5, for example, a hairpin promoter inverted repeat (pIR) directed to Ms1 or Ms5.

In one embodiment, the insertion of the inverted gene fragment can result in the formation of an in-vivo created inverted repeat (hairpin) in a native (or modified) promoter of a gene and/or in a native 5' end of the native gene. The inverted gene fragment can further comprise an intron which can result in an enhanced silencing of the targeted endogenous Ms1 or Ms5 gene.

In one embodiment, the region of interest can be flanked by two independent guide polynucleotide/CAS endonuclease target sequences. Cutting would be done concurrently. The deletion event would be the repair of the two chromosomal ends without the region of interest. Alternative results would include inversions of the region of interest, mutations at the cut sites and duplication of the region of interest. Furthermore, the introduced genetic modification may also comprise antisense sequences complementary to at least a portion of the messenger RNA (mRNA) for Ms1 or Ms5. Modifications of the antisense sequences may be made as long as the sequences hybridize to and interfere with expression of the corresponding mRNA. In this manner, antisense constructions having 70%, 80%, or 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

In addition, the introduced genetic modification may also be a polynucleotide arranged in the sense orientation to suppress the expression of endogenous Ms1 or Ms5 genes in plants. Methods for suppressing gene expression in plants using polynucleotides in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, generally greater than about 65% sequence identity, about 85% sequence identity, or greater than about 95% sequence identity. See, U.S. Pat. Nos. 5,283,184 and 5,034,323; herein incorporated by reference.

Protocols for introducing polynucleotides and polypeptides into plants may vary depending on the type of plant or plant cell targeted for transformation, such as monocot or dicot. Suitable methods of introducing polynucleotides and polypeptides into plant cells include but are not limited to Agrobacterium-mediated transformation (U.S. Pat. Nos. 5,563,055 and 5,981,840), direct gene transfer (Paszkowski et al., (1984) EMBO J 3:2717-22), and ballistic particle acceleration (U.S. Pat. Nos. 4,945,050; 5,879,918; 5,886,244; 5,932,782; Tomes et al., (1995) "Direct DNA Transfer into Intact Plant Cells via Microprojectile Bombardment" in Plant Cell, Tissue, and Organ Culture: Fundamental Methods, ed. Gamborg & Phillips (Springer-Verlag, Berlin). Wheat transformation may be carried out by any suitable technique known to one skilled in the art, including those described in published patent application no. 20140173781 published on Jun. 19, 2014.

Methods for Identifying at Least One Plant Cell Comprising in its Genome the Introduced Genetic Modification at the Target Site.

Further provided are methods for identifying at least one plant cell, comprising in its genome, the introduced genetic modification at the target site. A variety of methods are available for identifying those plant cells with the introduced genetic modification into the genome at or near to the target site without using a screenable marker phenotype. Such methods can be viewed as directly analyzing a target sequence to detect any change in the target sequence, including but not limited to PCR methods, sequencing methods, nuclease digestion, Southern blots, and any combination thereof. See, for example, U.S. patent application Ser. No. 12/147,834, herein incorporated by reference. The method also comprises recovering a male-sterile plant from the plant cell having the introduced genetic modification in its genome.

The present disclosure further provides expression constructs for expressing in a plant, plant cell, or plant part a guide RNA/Cas system that is capable of binding to and creating a double strand break in a target site of the fertility gene locus of Ms1 or Ms5. In one embodiment, the expression constructs of the disclosure comprise a promoter operably linked to a nucleotide sequence encoding a Cas gene and a promoter operably linked to a guide RNA of the present disclosure. The promoter is capable of driving expression of an operably linked nucleotide sequence in a plant cell.

A promoter is a region of DNA involved in recognition and binding of RNA polymerase and other proteins to initiate transcription. A plant promoter is a promoter capable of initiating transcription in a plant cell, for a review of plant promoters, see, Potenza et al., (2004) In Vitro Cell Dev Biol 40:1-22. Constitutive promoters include, for example, the core promoter of the Rsyn7 promoter and other constitutive promoters disclosed in WO99/43838 and U.S. Pat. No. 6,072,050; the core CaMV 35S promoter (Odell et al., (1985) Nature 313:810-2); rice actin (McElroy et al., (1990) Plant Cell 2:163-71); ubiquitin (Christensen et al., (1989) Plant Mol Biol 12:619-32; Christensen et al., (1992) Plant Mol Biol 18:675-89); pEMU (Last et al., (1991) Theor Appl Genet 81:581-8); MAS (Velten et al., (1984) EMBO J 3:2723-30); ALS promoter (U.S. Pat. No. 5,659,026), and the like. Other constitutive promoters are described in, for example, U.S. Pat. Nos. 5,608,149; 5,608,144; 5,604,121; 5,569,597; 5,466,785; 5,399,680; 5,268,463; 5,608,142 and 6,177,611. In some examples, an inducible promoter may be used. Pathogen-inducible promoters induced following infection by a pathogen include, but are not limited to those regulating expression of PR proteins, SAR proteins, beta-1, 3-glucanase, chitinase, etc.

Marker Assisted Selection and Breeding of Plants

Use of markers, and/or genetically-linked nucleic acids is an effective method for selecting plant having the desired traits in breeding programs. For example, one advantage of marker-assisted selection over field evaluations is that MAS can be done at any time of year regardless of the growing season. Moreover, environmental effects are irrelevant to marker-assisted selection.

A plant breeder can advantageously use molecular markers to identify individuals containing any of the targeted genome edits by identifying marker alleles that show a statistically significant probability of co-segregation with male sterility, manifested as linkage disequilibrium. This is referred to as marker assisted selection (MAS). Thus, methods for the selection of mutant wheat plants that are homozygous or heterozygous for a mutation in the Ms1 or Ms5 gene, are also provided.

The $Ms5_{FS20}$ mutation, is a recessive mutation of the Ms5 gene that was induced in the Chris wheat variety using ethyl methanesulfonate (Franckowiak et al. 1976. Crop Sci. and was identified in the line FS-20, also known as FS20 (Klindworth et al. 2002. Crop Sci. 42:1447-1450). The $ms5_{FS20}$ gene was reported genetically linked to chromosome 3AL and on the basis of mapping data from crosses to Chinese Spring ditelosomic 3AL was presumed to be located at a position genetically independent of the centromere (Klindworth et al., 2002 Crop Sci. 42:1447-1450). The causal variation of the Ms5 mutation is provided herein, as are markers tightly linked to the Ms5 gene on chromosome 3AL and to TaLTPG2-3D on 3DL. Markers include but are not limited to MP0061, MP0070, MP0079, MP0090, MP091, MP0156, MP0179, MP0182, MP0190, MP0191, MP0192, MP0201, MP0126, MP0127, MP0130, MP0131, MP0211, MP0212, MP0215 and MP216; see SEQ ID NOS: 112-131. These Kompetitive Allele Specific PCR (KASP) marker amplicons, which comprise both alleles, result from a sub-genome-specific PCR using two allele-specific forward primers in combination with a single reverse primer; see SEQ ID NOS: 138-197. Allele-specific fluorescent tagging of amplicons facilitates allele detection. Such markers may be used to track $ms5_{FS20}$ and a particular TaLTPG2-3D allele in subsequent selfing and crossing of wheat lines containing the $ms5_{FS20}$ mutation, ensuring that the male sterility trait is advantageously inherited in a wheat breeding program.

A plant breeder can advantageously use molecular markers to identify individuals containing an Ms5 mutation by identifying marker alleles that show a statistically significant probability of co-segregation with male sterility, manifested as linkage disequilibrium. This is referred to as marker assisted selection (MAS). Thus, methods for the selection of mutant wheat plants that are homozygous or heterozygous for a mutation in the Ms5 gene, such as but not limited to $ms5_{FS20}$ are also provided.

To perform MAS, a nucleic acid corresponding to the marker nucleic acid allele is detected in a biological sample from a plant to be selected. This detection can take the form of hybridization of a probe nucleic acid to a marker allele or amplicon thereof, e.g., using allele-specific hybridization, Southern analysis, northern analysis, in situ hybridization, hybridization of primers followed by PCR amplification of a region of the marker, DNA sequencing of a PCR amplification product, or the like. For any of the marker sequences described herein, one of ordinary skill in the art would understand how to obtain the allele at a marker locus in a particular wheat line or variety using known DNA amplification and sequencing techniques. For the purposes described herein, the lines or varieties that were used were publicly available. Hence, DNA could be obtained, and one of ordinary skill in the art could either use the provided primers or develop primers from the provided reference sequence to amplify and obtain the sequence at each marker locus from each line or variety.

After the presence (or absence) of a particular marker allele in the biological sample is verified, the plant is selected and is crossed to a second plant, optionally a wheat plant from an elite line. The progeny plants produced by the cross can be evaluated for that specific marker allele, and only those progeny plants that have the desired marker allele will be chosen.

Through marker assisted selection, a plant breeder can follow the presence of the male sterility trait through controlled crosses to obtain, when desired, a new plant containing a Ms1 or Ms5 gene mutation in either the homozygous or heterozygous state, thus maintaining the Ms1 or Ms5 gene mutations. In addition, marker assisted selection can be used to produce mutant male sterile seed parents that would be used as female, i.e. plants that need pollination by a pollen donor plant, to produce seeds of commercial interest. Alternatively, marker assisted selection could be used to produce $F_1$ hybrids containing a Ms1 or Ms5 gene mutation in the heterozygous state.

Any of the markers provided herein, as well as any marker linked to and associated with any of those markers, can be used for marker assisted selection of the male sterility trait.

Compositions and methods for restoring male fertility to a male-sterile plant are provided. In some examples, the male-sterile plants are homozygous recessive for the fertility gene of Ms1 or Ms5. In some embodiments, the male-sterile phenotype is caused by the introduction of genetic modification of a target site located in a male fertility gene locus of Ms1 or Ms5 in a plant cell's genome. In some examples, the wheat genomes (A, B, and D) contain homologous genes that have similar gene structure and function, requiring triple mutants to result in a male-sterile phenotype. Male-sterile plants may be created using the methods and compositions described herein and those known to one skilled in the art. In some embodiments, provided herein are compositions and methods to complement and restore male fertility to wheat plants containing mutations or introduced genetic modifications in Ms1 or Ms5 genes or Ms1 or Ms5 locus.

Male-sterile plants may be restored to male fertility when a functional copy of the Ms1 or Ms5 fertility gene, from the same or different species, is used to complement the Ms1 or Ms5 mutation or introduced genetic modification. See, for example, Example 11 herein.

When the male-fertility Ms1 or Ms5 polynucleotide, fragment or variant is expressed, the plant is able to successfully produce mature pollen grains because the male-fertility polynucleotide restores the plant to a fertile condition. In some examples, the Ms1 or Ms5 polynucleotide, fragment, or variant thereof is maintained in a hemizygous state in a plant, so that only certain daughter cells will inherit the Ms1 or Ms5 polynucleotide, fragment, or variant in the process of pollen grain formation. Hemizygosity is a genetic condition existing when there is only one copy of a gene (or set of genes) with no allelic counterpart.

In some embodiments, the male-fertility Ms1 or Ms5 polynucleotide, fragment, or variants thereof, is operably linked to a promoter, to express the Ms1 or Ms5 polynucleotide, fragment, or variant and modulate, e.g, restore, the male fertility of a plant. In some examples, the Ms1 or Ms5 polynucleotide, fragment, or variant are expressed from an expression cassette. In some embodiments, the male-fertility Ms1 or Ms5 polynucleotides or expression cassette disclosed herein are maintained in a hemizygous state in a plant.

In particular embodiments, the male-fertility Ms1 or Ms5 polynucleotide, or fragment or variant thereof, is operably linked to a promoter. In certain embodiments, plant promoters can preferentially initiate transcription in certain tissues, such as stamen, anther, filament, and pollen, or developmental growth stages, such as sporogenous tissue, microspores, and microgametophyte. Such plant promoters are referred to as "tissue-preferred," "cell-type-preferred," or "growth-stage preferred." Promoters which initiate transcription only in certain tissue are referred to as "tissue-specific." Likewise, promoters which initiate transcription only at certain growth stages are referred to as "growth-stage-specific." A "cell-type-specific" promoter drives expression only in certain cell types in one or more organs, for example, stamen cells, or individual cell types within the stamen such as anther, filament, or pollen cells.

A "male-fertility promoter" may initiate transcription exclusively or preferentially in a cell or tissue involved in the process of microsporogenesis or microgametogenesis. Male-fertility polynucleotides disclosed herein, and active fragments and variants thereof, can be operably linked to male-tissue-specific or male-tissue-preferred promoters including, for example, stamen-specific or stamen-preferred promoters, anther-specific or anther-preferred promoters, pollen-specific or pollen-preferred promoters, tapetum-specific promoters or tapetum-preferred promoters, and the like. Promoters can be selected based on the desired outcome. For example, the Ms1 or Ms5 polynucleotides can be operably linked to constitutive, tissue-preferred, growth stage-preferred, or other promoters for expression in plants. In one embodiment, the promoters may be those which express an operably-linked Ms1 or Ms5 polynucleotide exclusively or preferentially in the male tissues of the plant. Any suitable male-fertility tissue-preferred or tissue-specific promoter may be used in the process; and any of the many such promoters known to one skilled in the art may be employed. One such promoter is the 5126 promoter, which preferentially directs expression of the polynucleotide to which it is linked to male tissue of the plants, as described in U.S. Pat. Nos. 5,837,851 and 5,689,051. Other exemplary promoters include the native promoter of Ms1 or Ms5, including those known and disclosed herein in SEQ ID NO: 2, 7, 12, 17, 22, 30, 37, 42, 47, 52 or 200.

In some examples, a termination region is operably linked to the male-fertility Ms1 or Ms5 polynucleotide, fragment or variant. In some examples, the terminator region is the native terminator of Ms1 or Ms5, including those known and disclosed herein.

Where appropriate, the Ms1 or Ms5 polynucleotides may be optimized for increased expression in the plant. That is, the Ms1 or Ms5 polynucleotides can be synthesized or altered to use plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

A male-fertility Ms1 or Ms5 polynucleotide disclosed herein can be provided in an expression cassette for expression in a plant of interest. The cassette can include 5' and 3' regulatory sequences operably linked to a male-fertility polynucleotide as disclosed herein. In some examples, the expression cassette includes in addition to the polynucleotide encoding the Ms1 or Ms5 polypeptide a male-gamete-disruptive polynucleotide, that is, a polynucleotide which interferes with the function, formation, or dispersal of male gametes. A male-gamete-disruptive polynucleotide can operate to prevent function, formation, or dispersal of male gametes by any of a variety of methods. By way of example but not limitation, this can include use of polynucleotides which encode a gene product such as DAM-methylase or barnase (See, for example, U.S. Pat. No. 5,792,853 or 5,689,049; PCT/EP89/00495); encode a gene product which interferes with the accumulation of starch, degrades starch, or affects osmotic balance in pollen, such as alpha-amylase (See, for example, U.S. Pat. Nos. 7,875,764; 8,013,218; 7,696,405, 8,614,367); inhibit formation of a gene product important to male gamete function, formation, or dispersal (See, for example, U.S. Pat. Nos. 5,859,341; 6,297,426). In some examples, the male-gamete-disruptive polynucleotide is operably linked to a male-tissue-preferred promoter.

When the expression cassette is introduced into the plant in a hemizygous condition, only certain daughter cells will inherit the expression cassette in the process of pollen grain formation. The daughter cells that inherit the expression cassette containing the male-fertility Ms1 or Ms5 polynucleotide will not develop into mature pollen grains due to the male-tissue-preferred expression of the stacked encoded male-gamete-disruptive gene product. Those pollen grains that do not inherit the expression cassette will continue to develop into mature pollen grains and be functional, but will not contain the male-fertility polynucleotide of the expression cassette and therefore will not transmit the male-fertility polynucleotide to progeny through pollen. See, for example, U.S. Pat. Nos. 7,875,764; 8,013,218; 7,696,405, 8,614,367, herein incorporated by reference in its entirety.

In one embodiment, the homozygous recessive condition of a male-sterile plant produced using methods described herein is maintained. A method of maintaining the homozygous recessive condition of a male-sterile plant may include fertilizing the homozygous recessive male-sterile plant with pollen from a plant expressing (1) a Ms1 or Ms5 fertility gene that when the gene is expressed in the plant restores male fertility to the male-sterile plant and (2) a polynucleotide sequence that inhibits the function or formation of viable male gametes, which are driven by promoters that preferentially expresses the sequence in male plant cells, such as male gametes. See, for example, U.S. Pat. No. 8,614,367. The progeny produced will continue to be male sterile as a result of maintaining homozygosity for the fertility gene, e.g. Ms1 or Ms5. The progeny will not contain the introduced restoring fertility gene-male gamete inhibition construct. The plant having the restorer nucleotide sequence may be self-fertilized, that is pollen from the plant transferred to the flower of the same plant to achieve the propagation of the restorer plants. Note that in referring to "self fertilization", it includes the situation where the plant producing the pollen is fertilized with that same pollen, and the situation where two or more identical inbred plants are planted together and pollen from the identical inbred plant pollinate a different identical inbred plant. The pollen will not have the restoring transgene construct but it will be contained in 50% of the ovules (the female gamete). The seed resulting from the self-fertilization can be planted, and selection made for the seed having the restoring fertility gene-male gamete inhibition construct. Selection will allow for the identification of those plants produced from the seed having the restoring fertility gene-male gamete inhibition construct.

Definitions

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

"Coding region" generally refers to the portion of a messenger RNA (or the corresponding portion of another nucleic acid molecule such as a DNA molecule) which encodes a protein or polypeptide. "Non-coding region" generally refers to all portions of a messenger RNA or other nucleic acid molecule that are not a coding region, including but not limited to, for example, the promoter region, 5' untranslated region ("UTR"), 3' UTR, intron and terminator. The terms "coding region" and "coding sequence" are used interchangeably herein. The terms "non-coding region" and "non-coding sequence" are used interchangeably herein.

"Cosuppression" generally refers to the production of sense RNA transcripts capable of suppressing the expression of the target gene or gene product. "Sense" RNA generally refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see Vaucheret et al., *Plant J.* 16:651-659 (1998); and Gura, *Nature* 404:804-808 (2000)).

The term "crossed" or "cross" or "crossing" in the context of this disclosure means the fusion of gametes via pollination to produce progeny (i.e., cells, seeds, or plants). The term encompasses both sexual crosses (the pollination of one plant by another) and selfing (self-pollination, i.e., when the pollen and ovule (or microspores and megaspores) are from the same plant or genetically identical plants).

"Expression" generally refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

The terms "full complement" and "full-length complement" are used interchangeably herein, and refer to a complement of a given nucleotide sequence, wherein the complement and the nucleotide sequence consist of the same number of nucleotides and are 100% complementary.

"Gamete" refers to a reproductive cell having the 1 n set (haploid number) of chromosomes that can fuse with another gamete of the opposite sex during fertilization in organisms undergoing sexual reproduction. As used herein, a gamete in organisms undergoing asexual reproduction refers to a cell having a 2n number (an unreduced number) of chromosomes.

The term "gene" as used herein refers to a polynucleotide that is expressed by at least one of transcription and translation. An example of a gene is a nucleic acid fragment capable of being transcribed into mRNA or translated into a protein. A "gene" may or may not include a coding region or a regulatory sequence of a 5'-non coding sequence and a 3'-non coding sequence in addition to the coding region. For example, a Ms5 gene refers to a Ms5 polynucleotide that is expressed by at least one of transcription and translation.

As used herein, the term "gene locus" refers to the position of a gene on a genome. For example, Ms5 gene locus refers to the position of a Ms5 gene on genome.

The term "genome" refers to the entire complement of genetic material (genes and non-coding sequences) that is present in each cell of an organism, or virus or organelle; and/or a complete set of chromosomes inherited as a (haploid) unit from one parent.

"Heterologous" with respect to sequence means a sequence that originates from a foreign species, or, if from the same species, is substantially modified from its native form in composition and/or genomic locus by deliberate human intervention.

The term "introduced" in the context of inserting a nucleic acid into a cell," and includes reference to the incorporation of a nucleic acid or nucleic acid fragment into a eukaryotic or prokaryotic cell where the nucleic acid may be incorporated into the genome of the cell (e.g., chromosome, plasmid, plastid or mitochondrial DNA), converted into an autonomous replicon or transiently expressed (e.g., transfected mRNA).

"Isolated" generally refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. The term also embraces recombinant polynucleotides and chemically synthesized polynucleotides.

As used herein, a "male sterile plant" is a plant that does not produce male gametes that are viable or otherwise capable of fertilization.

The term "miRNA* sequence" refers to a sequence in the miRNA precursor that is highly complementary to the miRNA sequence. The miRNA and miRNA* sequences form part of the stem region of the miRNA precursor hairpin structure.

The terms "monocot" and "monocotyledonous plant" are used interchangeably herein. A monocot of the current disclosure includes the Gramineae.

"Percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways that are within the skill in the art, for instance, using publicly available computer software such as BLAST, BLAST-2. Those skilled in the art can determine appropriate parameters for aligning sequences, including any algorithms needed to achieve maximal alignment over the full length of the sequences being compared. In certain embodiments, sequence identity may be based on the Clustal V or Clustal W method of alignment. The term "about" when used herein in context with percent sequence identity means+/−1.0%.

The term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. Plant parts include differentiated and undifferentiated tissues including, but not limited to roots, stems, shoots, leaves, pollen, seeds, tumor tissue and various forms of cells and culture (e.g., single cells, protoplasts, embryos, and callus tissue). The plant tissue may be in plant or in a plant organ, tissue or cell culture. The term "plant organ" refers to plant tissue or a group of tissues that constitute a morphologically and functionally distinct part of a plant.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases.

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

"Polypeptide", "peptide", "amino acid sequence" and "protein" are used interchangeably herein to refer to a polymer of amino acid residues.

"Progeny" comprises any subsequent generation of a plant. "Promoter functional in a plant" is a promoter capable of controlling transcription in plant cells whether or not its origin is from a plant cell.

As used herein "promoter" includes reference to a region of DNA upstream from the start of transcription and involved in recognition and binding of RNA polymerase and other proteins to initiate transcription.

A "plant promoter" is a promoter capable of initiating transcription in plant cells.

"Recombinant" generally refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterologous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" generally refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature. The terms "recombinant DNA construct" and "recombinant construct" are used interchangeably herein.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity and most preferably 100% sequence identity (i.e., complementary) with each other.

The terms "stringent conditions" or "stringent hybridization conditions" means conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence. The term "under stringent conditions" means that two sequences hybridize under moderately or highly stringent conditions. More specifically, moderately stringent conditions can be readily determined by those having ordinary skill in the art, e.g., depending on the length of DNA. The basic conditions are set forth by Sambrook et al., Molecular Cloning: A Laboratory Manual, third edition, chapters 6 and 7, Cold Spring Harbor Laboratory Press, 2001 and include the use of a prewashing solution for nitrocellulose filters 5×SSC, 0.5% SDS, 1.0 mM EDTA (pH 8.0), hybridization conditions of about 50% formamide, 2×SSC to 6×SSC at about 40-50° C. (or other similar hybridization solutions, such as Stark's solution, in about 50% formamide at about 42° C.) and washing conditions of, for example, about 40-60° C., 0.5-6×SSC, 0.1% SDS. Preferably, moderately stringent conditions include hybridization (and washing) at about 50° C. and 6×SSC. Highly stringent conditions can also be readily determined by those skilled in the art, e.g., depending on the length of DNA.

Generally, such conditions include hybridization and/or washing at higher temperature and/or lower salt concentration (such as hybridization at about 65° C., 6×SSC to 0.2×SSC, preferably 6×SSC, more preferably 2×SSC, most preferably 0.2×SSC), compared to the moderately stringent conditions. For example, highly stringent conditions may include hybridization as defined above, and washing at approximately 65-68° C., 0.2×SSC, 0.1% SDS. SSPE (1×SSPE is 0.15 M NaCl, 10 mM $NaH_2PO_4$, and 1.25 mM EDTA, pH 7.4) can be substituted for SSC (1×SSC is 0.15 M NaCl and 15 mM sodium citrate) in the hybridization and washing buffers; washing is performed for 15 minutes after hybridization is completed.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90% and most preferably at least 95%.

Another indication that nucleotide sequences are substantially identical is if two molecules hybridize to each other under stringent conditions. The degeneracy of the genetic code allows for many amino acids substitutions that lead to variety in the nucleotide sequence that code for the same amino acid, hence it is possible that the DNA sequence could code for the same polypeptide but not hybridize to each other under stringent conditions. This may occur, e.g., when a copy of a nucleic acid is created using the maximum codon degeneracy permitted by the genetic code. One indication that two nucleic acid sequences are substantially identical is that the polypeptide, which the first nucleic acid encodes, is immunologically cross reactive with the polypeptide encoded by the second nucleic acid.

The terms "substantial identity" in the context of a peptide indicates that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm of Needleman and Wunsch, supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. In addition, a peptide can be substantially identical to a second peptide when they differ by a non-conservative change if the epitope that the antibody recognizes is substantially identical. Peptides, which are "substantially similar" share sequences as, noted above except that residue positions, which are not identical, may differ by conservative amino acid changes.

The terms "suppress", "suppressed", "suppression", "suppressing" and "silencing", are used interchangeably herein and include lowering, reducing, declining, decreasing, inhibiting, eliminating or preventing. "Silencing" or "gene silencing" does not specify mechanism and is inclusive, and not limited to, antisense, cosuppression, viral-suppression, hairpin suppression, stem-loop suppression, RNAi-based approaches, and small RNA-based approaches and the like.

"Transcription terminator", "termination sequences", or "terminator" refer to DNA sequences located downstream of a protein-coding sequence, including polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al., *Plant Cell* 1:671-680 (1989). A polynucleotide sequence with "terminator activity" generally refers to a polynucleotide sequence that, when operably linked to the 3' end of a second polynucleotide sequence that is to be expressed, is capable of terminating transcription from the second polynucleotide sequence and facilitating efficient 3' end processing of the messenger RNA resulting in addition of poly A tail. Transcription termination is the process by which RNA synthesis by RNA polymerase is stopped and both the processed messenger RNA and the enzyme are released from the DNA template.

The term "under stringent conditions" means that two sequences hybridize under moderately or highly stringent conditions.

As used herein, the term "wheat" refers to any species of the genus *Triticum*, including progenitors thereof, as well as progeny thereof produced by crosses with other species. Wheat includes "hexaploid wheat" which has genome organization of AABBDD, comprised of 42 chromosomes, and "tetraploid wheat" which has genome organization of AABB, comprised of 28 chromosomes. Hexaploid wheat includes *T. aestivum, T. spelta, T. mocha, T. compactum, T. sphaerococcum, T. vavilovii*, and interspecies cross thereof. Tetraploid wheat includes *T. durum* (also referred to as durum wheat or *Triticum turgidum* ssp. durum), *T. dicoccoides, T. dicoccum, T. polonicum*, and interspecies cross thereof. In addition, the term "wheat" includes possible progenitors of hexaploid or tetraploid *Triticum* sp. such as *T. uartu, T. monococcum* or *T. boeoticum* for the A genome, *Aegilops speltoides* for the B genome, and *T. tauschii* (also known as *Aegilops squarrosa* or *Aegilops tauschii*) for the D genome. A wheat cultivar for use in the present disclosure may belong to, but is not limited to, any of the above-listed species. Also encompassed are plants that are produced by conventional techniques using *Triticum* sp. as a parent in a sexual cross with a non-Triticum species, such as rye (*Secale cereale*), including but not limited to Triticale. In some embodiments, the wheat plant is suitable for commercial production of grain, such as commercial varieties of hexaploid wheat or durum wheat, having suitable agronomic characteristics which are known to those skilled in the art.

The meaning of abbreviations is as follows: "sec" means second(s), "min" means minute(s), "h" means hour(s), "d" means day(s), "A" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kb" means kilobase(s).

Also, as described herein, for each example or embodiment that cites a guide RNA, a similar guide polynucleotide can be designed wherein the guide polynucleotide does not solely comprise ribonucleic acids but wherein the guide polynucleotide comprises a combination of RNA-DNA molecules or solely comprises DNA molecules.

EXAMPLES

In the following Examples, unless otherwise stated, parts and percentages are by weight and degrees are Celsius. It should be understood that these Examples, while indicating embodiments of the disclosure, are given by way of illustration only. From the above discussion and these Examples, one skilled in the art can make various changes and modifications of the disclosure to adapt it to various usages and conditions. Such modifications are also intended to fall within the scope of the appended claims.

Example 1: Expression Cassettes for Guide RNA/Cas Endonuclease Based Genome Modification in Wheat Plants The gRNA expression cassette consisted of the wheat U6 promoter and the gRNA scaffold, both of which are described in Shan et al. 2013, *Nature Biotechnology* 31:686-688. See, SEQ ID NOs:202 and 204 respectively. The Cas9 expression cassette consisted of the *Zea mays* Ubiquitin 1 promoter (described in Christensen et al. 1992, *Plant Molecular Biology* 18:675-689), the rice codon-optimised Cas9 gene (described in Shan et al. 2013, *Nature Biotechnology* 31:686-688), and the *Sorghum bicolor* actin terminator. See, SEQ ID NOs:205-207 respectively. The selection cassette consisted of the *Zea mays* Ubiquitin 1 promoter with modified first intron, the intron-containing bar gene and the wheat rbcS terminator (described in Sasanuma 2001, *Molecular Genetics and Genomics* 265:161-171). See, SEQ ID NOs:212 and 203—respectively.

Example 2: Wheat Transformation

*Agrobacterium*-mediated transformation of wheat cv. Fielder and cv. Gladius was carried out as described (Ishida et al. 2015, Methods in Molecular Biology 1223:189-198), with minor modifications. Briefly, immatures embryos were isolated from spikes harvested at 14 days post-anthesis. Isolated embryos were transferred to WLS-liq solution, centrifuged at 16,000 g for 10 mins, incubated in WLS-inf solution containing *Agrobacterium* (AGL1) for 5 mins, and then transferred to WLS-AS media for two days of co-cultivation. After co-cultivation, embryo axes were removed, and then scutella were transferred to WLS-Res media for five days of resting culture. After the resting culture, scutella were transferred to WLS-P5 callus induction media (selection with 5 mg/L phosphinothricin) for two weeks, followed by WLS-P10 callus induction media (selection with 10 mg/L phosphinothricin) for three weeks. Calli were then transferred to LSZ-P5 regeneration media for two weeks under a cycle of 12 hours dark/12 hours light (~70 μmol/m2/s). Regenerants were transferred to LSF-P5 rooting media for two weeks, before being transferred to potted soil in the greenhouse. Timentin was substituted for cefotaxime in all tissue culture media.

Example 3: TaMs1 Mutation in B Genome with CRISPR-Cas9 Results in Male Sterile Wheat This example shows that homozygous TaMs1 knockout mutant plants derived from CRISPR-Cas9 induced mutations in the B genome (chromosome 4BS) exhibit a male sterile phenotype. The T0 line GL353-119 was a biallelic heterozygous mutant on 4BS with a +1 insertion in one allele, and a −3 deletion in the other allele. Both mutations were located precisely at the canonical Cas9 cut site for gRNA LTPG1-2 (SEQ ID NO:82). GL353-119 was partially sterile. GL353-119 was crossed with wildtype Gladius to produce+1/WT and −3/WT seeds (T1 generation). One of the +1/WT seeds that lacked DsRed expression was planted and grown to maturity to produce T2 seeds. Thirty of these T2 seeds were planted out, and the seedlings were genotyped. Of the 30 seedlings, four were +1/+1, 18 were +1/WT, and eight were WT/WT. The thirty T2 seedlings were grown to maturity. All +1/+1 mutants were fully sterile, whereas all +1/WT and WT/WT plants were fully fertile.

Example 4: Phenotypic Assessment Facilitating Mapping of Ms5$_{FS20}$

Phenotyping for genetic male sterility was performed by quantitative and/or qualitative methods. For both methods at least 3 spikes per plant were securely covered with sealed white paper bags prior to anthesis and were then used for fertility assessment. A quantitative fertility score was determined by counting the number of florets per spike and the number of seeds per spike and expressing the score as the number of seeds per floret formed. A qualitative assessment was made by visual examination of the spikes for seed set and evidence of anther dehiscence. Anthers of ms5$_{FS20}$ plants do not dehisce and florets of heads bagged prior to anthesis do not set seed and are deemed male sterile, while spikes of Ms5 plants show high levels of dehisced anthers and a high proportion of florets with seed and therefore deemed male fertile.

Example 5: Genetic Mapping of Ms5

This example demonstrates that by using recombinant mapping populations of wild-type and male-sterile wheat, the causative locus for the male-sterile phenotype of wheat ms5$_{FS20}$ can be mapped to a 0.012 cM region proximal on the long arm of chromosome 3 of the A genome. Populations ms5$_{FS20}$×H45 and ms5$_{FS20}$×Excalibur were selected for genetic mapping of Ms5 because inheritance of sterility in these populations was mono-factorial and bi-factorial respectively. Fine mapping was performed using ms5$_{FS20}$× H45 populations because mono-factorial inheritance provides a greater proportion of informative lines per number of lines genotyped than populations where inheritance is bi-factorial. y A male sterile (msms) wheat, var. Chris, carrying the FS20 mutant gene (also referred to as FS-20, ms5 and ms5$_{FS20}$) was crossed to plants of cvs. H45 and Excalibur to create F$_2$ mapping populations. Initial mapping to establish a broad interval spanning the Ms5 locus was undertaken in the ms5$_{FS20}$×Excalibur population. Sequences that were genetically positioned across a region covering the proximal region of 3AS and most of 3AL were targeted for marker development and were identified based either on synteny with wheat chromosome 3B (Choulet et al. 2014. Science 345(6194): 1249721), barley chromosome 3H (Mayer et al. 2012. *Nature* 491(7426):711-716), rice chromosome 1 (Kawahara et al., 2013 *Rice* 6: 4) or from a 90K consensus wheat single-nucleotide polymorphism (SNP) map (Wang et al., 2014 *Plant Biotechnology* 12:787-796). For example, corresponding wheat sequence contigs from reference syntenic sequences (e.g. rice gene LOC_Os01g42210, for which SEQ ID NO:48 represents a reference sequence) were identified by BLASTn to chromosome 3A-derived IWGSC (International Wheat Genome Sequencing Consortium) survey sequence assemblies (Mayer et al., 2014 *Science* 345 (6194): 1251788) or to Chinese Spring TGACv1 scaffolds (Clavijo et al., 2017 *Genome Res* 27:885-896) or to Synthetic W7984 scaffolds (Chapman et al. 2014 *Genome Biol* 16:26). Several methods were used to identify SNP-containing wheat sequences; direct comparison of Illumina HiSeq genomic sequences of 40 homozygous ms5$_{FS20}$ individuals and 20 homozygous Ms5$_{FS20}$ individuals, mapping of RNAseq reads from a homozygous fertile Ms5$_{FS20}$ plant against 454 sequences of cv. Excalibur (ref BioPlatforms Australia), retrieval and examination of ms5$_{FS20}$ and Ms5$_{FS20}$ promoter sequences of anther transcripts which had been identified by RNAseq to be differentially expressed between ms5$_{FS20}$ and Ms5$_{FS20}$ lines. Identified SNPs were selected for marker design based on location of homeologous 3B sequences, location of orthologous 3H sequences or location of orthologous rice sequences. SNPs were further prioritized based on SNP type, with C/G to T/A transitions preferred, and on rarity of the ms5$_{FS20}$ base when compared to sequences of homeologues and other wheat cultivars (ref BioPlatforms Australia). Identified SNPs were targeted for High Resolution Melting (HRM) marker development, Kompetitive Allele Specific PCR (KASP) marker development or Cleaved Amplified Polymorphic Sequence (CAPS) marker development. CAPS markers were developed using the NEBcutter v2.0 tool (Vincze et al., 2003 Nucleic Acids Res 31(13): 3688-3691). A set of the developed markers was used to genotype 2,300 $ms5_{FS20}$×Excalibur $F_2$ and $F_3$ plants, providing a subset of 325 plants which were predicted to be homozygous $ms5_{FS20}$ or recombinant in the region of $ms5_{FS20}$ and which were grown for phenotyping. Markers flanking $ms5_{FS20}$ were experimentally determined by linkage analysis of 106 plants from the subset that showed complete sterility. In contrast to the report of Klindworth et al. (2002), the analysis showed that the region containing Ms5 is highly proximal to the 3A centromere, locating between the short arm marker MP0070 (SEQ ID: 113) and the long arm marker MP0061 (SEQ ID NO: 112). Markers MP0070 and MP0061 correspond to 3A-derived IWGSC sequence contigs IcI|3AS_3345038 and IcI|3AL_4288243 respectively (Mayer et al., 2014 Science 345 (6194): 1251788). This region was determined to approximately cover a genetic distance of 0.77cM on the 90K consensus map (Wang et al., 2014 *Plant Biotechnology* 12:787-796). Inheritance of sterility in this population was determined to be controlled by homeologous loci on chromosomes 3A and 3D, with fertility levels comparable to those of wild-type plants observed in $ms5_{FS20}/ms5_{FS20}$ genotypes which were homozygous for Excalibur alleles in the 3D region corresponding to the region on 3A shown to contain $ms5_{FS20}$.

Fine mapping of $ms5_{FS20}$ was performed using 743 $ms5_{FS20}$×H45 $F_2$ individuals which were screened with markers identified to be flanking the Ms5 region on chromosome 3A and polymorphic between $ms5_{FS20}$ and cv. H45. $F_2$ individuals were assessed phenotypically for male sterility using procedures described elsewhere. 16 recombinant lines were identified, and the Ms5 locus was located to a 0.13 cM interval between the KASP markers MP0091 (SEQ ID NO: 121) and MP0192 (SEQ ID NO: 122). KASP markers MP0091 and MP0192 were designated to 3AL-derived IWGSC sequence contigs IcI|3AL_4321937 and IcI|3AL_4455020, respectively (Mayer et al., 2014 *Science* 345 (6194): 1251788).

Markers were then developed in the region between markers MP0091 and MP0192 and tested for their association with the male sterility phenotype. A total of 7721 $F_3$ and $F_4$ $ms5_{FS20}$×H45 individuals, derived from lines that were known to be heterozygous in the region of Ms5, were screened and 15 recombinants were identified, narrowing the Ms5-containing region to an area bounded by markers MP0156 (SEQ ID NO:117) and MP0192 (SEQ ID NO:122). Markers MP0156 and MP0192 correspond to 3AL-derived IWGSC sequence contigs IcI|3AL_4306089 and IcI|3AL_4455020 respectively (Mayer et al., 2014 Science 345 (6194): 1251788) and define a 0.012 cM region in the cross $ms5_{FS20}$×H45.

Example 6: Genetic Mapping of a 3D Locus Restoring Fertility to $Ms5_{FS20}$

This example demonstrates that by using recombinant mapping populations of wild-type and male-sterile wheat, a locus capable of complementing the male-sterile phenotype of wheat $ms5_{FS20}$ can be mapped to a 1.19 cM region on chromosome 3 of the D genome which is syntenous with the location of $ms5_{FS20}$ on chromosome 3A.

Fertility assessment in an unbiased set of 80 $ms5_{FS20}$×Excalibur $F_2$ lines found three levels of fertility; high fertility, partial fertility and complete sterility. High or partial fertility was present in 74 lines (92.5%) and complete sterility in 6 lines (7.5%), consistent with bi-factorial control of fertility in Excalibur (Fishers Exact Test, 2-tail p=1). Similarly, fertility assessment of an unbiased set of 209 $ms5_{FS20}$×Gladius $F_2$ lines found three levels of fertility; high fertility, partial fertility and sterility. High or partial fertility was present in 191 lines (91.4%) and sterility in 18 lines (8.6%), consistent with bi-factorial control of fertility in Gladius (Fisher's Exact Test, 2-tail p=0.4558).

The subset of 325 $ms5_{FS20}$×Excalibur $F_2$ and $F_3$ plants described above was used to investigate full and partial fertility restoration that was observed in a proportion of lines which were expected to be homozygous for $ms5_{FS20}$ based on flanking marker genotype. Limiting the linkage analysis to 84 such lines which were observed to be highly fertile identified centromeric-proximal markers closely linked to a fertility restoration locus on chromosome 3D.

Fine mapping was performed using two populations; 209 $ms5_{FS20}$×Gladius $F_2$ individuals and 93 $ms5_{FS20}$×RAC875 $F_2$ individuals. The populations were screened with markers identified to be flanking the Ms5 region on chromosome 3D and polymorphic between $ms5_{FS20}$ and cv. Gladius or between $ms5_{FS20}$ and cv. RAC875. $F_2$ individuals were assessed phenotypically for male sterility using procedures described elsewhere herein (see Example 4). In the $ms5_{FS20}$×Gladius population 5 recombinant lines were identified and the fertility-restoring locus was located to a 1.19 cM interval between the KASP markers MP0216 (SEQ ID NO:131) and MP0215 (SEQ ID NO:130). KASP markers MP0216 and MP0215 were designated to 3DL-derived IWGSC sequence contigs IcI|3DL_6894520 and IcI|3DL_6852770, respectively (Mayer et al., 2014 Science 345 (6194): 1251788). In the $ms5_{FS20}$×RAC875 population 4 recombinant lines were identified and the fertility-restoring locus was located to a 2.15 cM interval between the KASP markers MP0211 (SEQ ID NO: 128) and MP0131 (SEQ ID NO: 127). KASP markers MP0211 and MP0131 were designated to 3DL-derived IWGSC sequence contigs IcI|3DL_6867260 and IcI|3DL_6953108, respectively (Mayer et al., 2014 Science 345 (6194): 1251788). Combining information from all three populations positioned the 3D fertility-restoring locus between markers MP0211 and MP0215.

Example 7: Identification of Candidate Ms5 Gene and Candidate 3D Fertility Gene

Comparison of marker order across the Ms5 region in 3A obtained by genetic mapping in the populations described above with that predicted by the then current 3B and 3H pseudomolecules showed limited agreement. Conversely, comparison to gene order in the rice Nipponbare RGAP 7 assembly (reference goes here) indicated a high degree of colinearity and therefore a 0.75 Mb interval of the rice genome from LOC_Os01g41030, which corresponds to MP0156, to LOC_Os01g42294, which corresponds to MP0192, was examined for Ms5 candidates.

Table 4 lists the 122 annotated rice genes within the interval LOC_Os01g41030 to LOC_Os01g42294 and their putative peptide function.

TABLE 4

| locus name | functional annotation |
| --- | --- |
| LOC_Os01g41030 | CDS ribosomal protein L25, putative |
| LOC_Os01g41040 | CDS SCF apoptosis response protein, putative |
| LOC_Os01g41050 | CDS sulfate transporter, putative |
| LOC_Os01g41060 | CDS retrotransposon protein, putative, unclassified |
| LOC_Os01g41070 | CDS retrotransposon protein, putative, unclassified |
| LOC_Os01g41080 | CDS retrotransposon protein, putative, unclassified |
| LOC_Os01g41090 | CDS retrotransposon protein, putative, unclassified |
| LOC_Os01g41100 | CDS retrotransposon protein, putative, unclassified |
| LOC_Os01g41110 | CDS expressed protein |
| LOC_Os01g41120 | CDS retrotransposon protein, putative, Ty3-gypsy subclass |
| LOC_Os01g41140 | CDS THION18 - Plant thionin family protein precursor |
| LOC_Os01g41145 | CDS retrotransposon protein, putative, unclassified |
| LOC_Os01g41160 | CDS FAD dependent oxidoreductase domain containing protein |
| LOC_Os01g41170 | CDS THION27 - Plant thionin family protein precursor |
| LOC_Os01g41180 | CDS THION19 - Plant thionin family protein precursor, putative |
| LOC_Os01g41190 | CDS glycine-rich protein, putative |
| LOC_Os01g41200 | CDS heavy metal-associated domain containing protein |
| LOC_Os01g41210 | CDS transposon protein, putative, unclassified |
| LOC_Os01g41220 | CDS DUF538 domain containing protein, putative |
| LOC_Os01g41230 | CDS hypothetical protein |
| LOC_Os01g41240 | CDS hydrolase, alpha/beta fold family domain containing protein |
| LOC_Os01g41250 | CDS OsFBX17 - F-box domain containing protein |
| LOC_Os01g41260 | CDS OsFBD2 - F-box and FBD domain containing protein |
| LOC_Os01g41270 | CDS OsFBD3 - F-box and FBD domain containing protein |
| LOC_Os01g41280 | CDS OsFBD4 - F-box and FBD domain containing protein |
| LOC_Os01g41290 | CDS OsFBD5 - F-box and FBD domain containing protein |
| LOC_Os01g41300 | CDS expressed protein |
| LOC_Os01g41310 | CDS OsFBX18 - F-box domain containing protein |
| LOC_Os01g41320 | CDS expressed protein |
| LOC_Os01g41330 | CDS hypothetical protein |
| LOC_Os01g41340 | CDS OsFBL1 - F-box domain and LRR containing protein |
| LOC_Os01g41350 | CDS expressed protein |
| LOC_Os01g41360 | CDS expressed protein |
| LOC_Os01g41370 | CDS FBD domain containing protein, putative |
| LOC_Os01g41390 | CDS retrotransposon, putative, centromere-specific |
| LOC_Os01g41400 | CDS transmembrane amino acid transporter protein, putative |
| LOC_Os01g41410 | CDS expressed protein |
| LOC_Os01g41420 | CDS transmembrane amino acid transporter protein, putative |
| LOC_Os01g41430 | CDS UDP-glucoronosyl and UDP-glucosyl transferase, putative |
| LOC_Os01g41440 | CDS retrotransposon protein, putative, unclassified |
| LOC_Os01g41450 | CDS UDP-glucoronosyl and UDP-glucosyl transferase domain containing protein |
| LOC_Os01g41460 | CDS retrotransposon protein, putative, Ty3-gypsy subclass |
| LOC_Os01g41470 | CDS retrotransposon protein, putative, Ty3-gypsy subclass |
| LOC_Os01g41480 | CDS retrotransposon protein, putative, Ty3-gypsy subclass |
| LOC_Os01g41490 | CDS retrotransposon protein, putative, Ty3-gypsy subclass |
| LOC_Os01g41500 | CDS retrotransposon protein, putative, unclassified |
| LOC_Os01g41510 | CDS calcineurin B, putative |
| LOC_Os01g41516 | CDS retrotransposon protein, putative, Ty1-copia subclass |
| LOC_Os01g41522 | CDS retrotransposon protein, putative, unclassified |
| LOC_Os01g41530 | CDS OsFBL2 - F-box domain and LRR containing protein |
| LOC_Os01g41540 | CDS hypothetical protein |
| LOC_Os01g41550 | CDS aspartic proteinase, putative |
| LOC_Os01g41560 | CDS hypothetical protein |
| LOC_Os01g41565 | CDS ATP-binding domain-containing protein, putative |
| LOC_Os01g41580 | CDS expressed protein |
| LOC_Os01g41590 | CDS transposon protein, putative, unclassified |
| LOC_Os01g41600 | CDS Sad1/UNC-like C-terminal domain containing protein, putative |
| LOC_Os01g41610 | CDS mitochondrial ATP synthase g subunit family protein, putative |
| LOC_Os01g41620 | CDS transposon protein, putative, unclassified |
| LOC_Os01g41630 | CDS serine/threonine protein phosphatase 2A 55 kDa regulatory subunit B, putative |
| LOC_Os01g41640 | CDS expressed protein |
| LOC_Os01g41650 | CDS pentatricopeptide, putative |
| LOC_Os01g41660 | CDS phosphoethanolamine/phosphocholine phosphatase, putative |
| LOC_Os01g41670 | CDS G-patch domain containing protein, putative |
| LOC_Os01g41680 | CDS retrotransposon protein, putative, unclassified |
| LOC_Os01g41690 | CDS transposon protein, putative, unclassified |
| LOC_Os01g41700 | CDS transposon protein, putative, unclassified |
| LOC_Os01g41710 | CDS chlorophyll A-B binding protein, putative |
| LOC_Os01g41720 | CDS expressed protein |
| LOC_Os01g41730 | CDS serine/threonine-protein kinase, putative |
| LOC_Os01g41740 | CDS expressed protein |
| LOC_Os01g41750 | CDS expressed protein |
| LOC_Os01g41760 | CDS expressed protein |
| LOC_Os01g41770 | CDS leucine rich repeat protein, putative |
| LOC_Os01g41780 | CDS expressed protein |
| LOC_Os01g41790 | CDS expressed protein |
| LOC_Os01g41800 | CDS cytochrome P450, putative |
| LOC_Os01g41810 | CDS cytochrome P450 72A1, putative |
| LOC_Os01g41820 | CDS cytochrome P450 72A1, putative |
| LOC_Os01g41834 | CDS chalcone synthase, putative |
| LOC_Os01g41850 | CDS transposon protein, putative, unclassified |
| LOC_Os01g41860 | CDS hypothetical protein |
| LOC_Os01g41870 | CDS protein kinase, putative |
| LOC_Os01g41880 | CDS hyaluronan/mRNA binding family domain containing protein |
| LOC_Os01g41890 | CDS MLA1, putative |
| LOC_Os01g41900 | CDS Myb transcription factor, putative |
| LOC_Os01g41910 | CDS receptor-like protein kinase 5 precursor, putative |
| LOC_Os01g41920 | CDS expressed protein |
| LOC_Os01g41930 | CDS leucine rich repeat protein, putative |
| LOC_Os01g41950 | CDS expressed protein |
| LOC_Os01g41960 | CDS retrotransposon protein, putative, unclassified |
| LOC_Os01g41970 | CDS expressed protein |
| LOC_Os01g41980 | CDS retrotransposon protein, putative, unclassified |
| LOC_Os01g41990 | CDS OsCML12 - Calmodulin-related calcium sensor protein |
| LOC_Os01g42000 | CDS skin secretory protein xP2 precursor, putative |
| LOC_Os01g42010 | CDS expressed protein |
| LOC_Os01g42020 | CDS retrotransposon protein, putative, LINE subclass |
| LOC_Os01g42024 | CDS expressed protein |
| LOC_Os01g42030 | CDS mitochondrial chaperone BCS1, putative |
| LOC_Os01g42040 | CDS ubiquitin-conjugating enzyme, putative |
| LOC_Os01g42050 | CDS DNL zinc finger domain containing protein, putative |
| LOC_Os01g42060 | CDS expressed protein |
| LOC_Os01g42070 | CDS kinesin motor domain containing protein, putative |
| LOC_Os01g42080 | CDS zinc ion binding protein, putative |
| LOC_Os01g42090 | CDS nodulin MtN3 family protein, putative |
| LOC_Os01g42100 | CDS expressed protein |
| LOC_Os01g42110 | CDS nodulin MtN3 family protein, putative |
| LOC_Os01g42120 | CDS expressed protein |
| LOC_Os01g42130 | CDS expressed protein |
| LOC_Os01g42140 | CDS expressed protein |
| LOC_Os01g42150 | CDS MEGL13 - Maternally expressed gene MEG family protein precursor |
| LOC_Os01g42160 | CDS MEGL14 - Maternally expressed gene MEG family protein precursor, putative |
| LOC_Os01g42170 | CDS zinc knuckle family protein |
| LOC_Os01g42190 | CDS heat shock protein DnaJ, putative |
| LOC_Os01g42200 | CDS expressed protein |
| LOC_Os01g42210 | CDS LTPL47 - Protease inhibitor/seed storage/LTP family protein precursor, putative |
| LOC_Os01g42220 | CDS expressed protein |
| LOC_Os01g42234 | CDS amino acid permease family protein, putative |
| LOC_Os01g42260 | CDS transcriptional corepressor LEUNIG, putative |
| LOC_Os01g42270 | CDS transcriptional corepressor LEUNIG, putative |

TABLE 4-continued

| locus name | functional annotation |
|---|---|
| LOC_Os01g42280 | CDS pentatricopeptide, putative |
| LOC_Os01g42294 | CDS inactive receptor kinase At2g26730 precursor, putative |

Among retrieved wheat sequences corresponding to the 122 annotated loci in the rice interval, 10 contained SNPs between ms5$_{FS20}$ and cv. H45. One identified SNP was predicted to be in the coding sequence of the wheat orthologue of LOC_Os01g42210, a polypeptide with similarity to non-specific lipid transfer protein (nsLTP) (Edstam et al., 2014 *Physiologia Plantarum* doi:10.1111/ppl.12156). This particular sequence is predicted to encode a glycosylphosphatidylinositol (GPI)-anchored nsLTP (LTPG) polypeptide (SEQ ID NO:19 is the amino acid sequence of the encoded protein). A functionally related sequence, TaLTPG1 (syn. TaMS1), was determined to have a crucial role in anther development (Tucker et al., 2017, *Nature Communications* 8(869):1-10), with mutated forms underlying the male-sterile phenotypes of ms1d, ms1e and ms1f. Therefore the identified 3A sequence has been named TaLTPG2-3A. Examination of retrieved sequences of homeologous loci TaLTPG2-3B and TaLTPG2-3D found two allelic forms for each homeolocus. Both alleles of TaLTPG2-3B were predicted to encode non-functional LTPG-type proteins as a result of coding sequence deletions. Genetic mapping of TaLTPG2-3D in ms5$_{FS20}$×Excalibur, ms5$_{FS20}$×Gladius and ms5$_{FS20}$×RAC875 located it within the determined critical fertility-restoring interval in each population. One allele of TaLTPG2-3D was predicted to encode a functional LTPG-type protein and this allelic form was found in the cultivars Excalibur, Gladius, RAC875 and Chinese Spring. A second allele of TaLTPG2-3D was predicted to encode a non-functional LTPG-type protein as a result of an exonic single base insertion at position 76-77 (–/C) of the genomic sequence of the functional form (SEQ ID NO: 28). The non-functional allelic form was found in cultivars Chris and H45 which do not contain sequences capable of complementing the ms5$_{FS20}$ phenotype. Agreement between allelic form, observed phenotype and trait inheritance pattern suggested TaLTPG2-3A as a likely candidate for Ms5.

Example 8: Isolation and Sequence of Wheat Mutant Ms5$_{FS20}$ Allele

Full-length coding sequences of TaLTPG2-3A from chromosome 3AL were PCR amplified from genomic DNAs isolated from male sterile homozygous Ethyl methanesulfonate (EMS)-induced mutant ms5$_{FS20}$ (Klindworth et al., 2002 *Crop Sci.* 42:1447-1450) and wild-type (Ms5) male fertile genotypes (cultivar Chris). Both strands of PCR amplicons were sequenced using standard Sanger sequencing techniques for GC-rich products. The Sanger sequencing chromatograms revealed a SNP between the ms5$_{FS20}$ mutant allele and the wild-type sequence. Sequence analysis predicts that protein function is disrupted for this mutant.

ms5$_{FS20}$ exhibits a SNP at position 101 (G101A) when compared to wild-type Ms5 genomic DNA sequence (SEQ ID NO:16). This SNP is predicted to convert a conserved Cysteine to a Tyrosine (C34Y) within the encoded wild-type Ms5 polypeptide (SEQ ID NO:19). This amino acid change is predicted to disrupt the tertiary conformation of the mature protein mediated by a putative di-sulfide bridge.

Example 9: Sequences of Wheat Ms5 Homologue Alleles

Sequences for the 3B and 3D Ms5 homeologues were retrieved for cultivars Chinese Spring, Chris, Excalibur, Gladius, H45, RAC875 and Synthetic W7984. Sequences for each genome were compared by alignment to detect variant alleles.

Relative to the wildtype form of Ms5, the TaLTPG2-3B allele in cultivar Chinese Spring (SEQ ID NO:21) contains a 1 bp deletion at position 140 of the reference sequence (SEQ ID NO:16), predicted to be in exon 1 and to cause a frameshift, resulting in translation to a polypeptide with no similarity to proteins of known function (SEQ ID NO:23). Relative to the wildtype form of Ms5, the TaLTPG2-3B allele in cultivar Synthetic W7984 (SEQ ID NO:199) contains a large deletion beginning within exon 1 and extending into intron 1, resulting in a shortened predicted polypeptide comprising 43 residues (SEQ ID NO: 26), the first 31 of which show homology to Ms5.

The TaLTPG2-3D alleles in cultivars Excalibur, Gladius and RAC875 and Synthetic W7984 encode identical polypeptide sequences (SEQ ID NO:34) and have high homology to the wildtype form of Ms5. The TaLTPG2-3D alleles in cultivars Chris and H45 contain an indel at position 77 of the reference TaLTPG2-3D coding sequence (SEQ ID NO:25). This indel causes a frame shift predicted to generate a non-functional truncated polypeptide comprising 141 amino acids (SEQ ID NO: 33), the first 26 of which show homology to Ms5.

Example 10: Markers in the Ms5 Region and their Use in Identifying and Selecting Wheat Plants Containing Ms5 Mutations The Ms5 gene was found to be tightly linked to markers MP0156, MP0179, MP0182, MP0190, MP0191, MP0192, MP0201, and MP0090 that are located in the Ms5 region. See SEQ ID NOS: 115, 117-123. The fertility restoration locus on chromosome 3D was found to be tightly linked to markers MP0126, MP0212, MP0127, MP0215 and MP0130 that are located in the Ms5 homeologous region. See SEQ ID NOS: 124-126 and 129-130. Because the male sterility trait is controlled by two nuclear recessive genes, all crosses between male sterile mutants and wild type pollinators will result in 100% male fertile $F_1$ progenies (Ms5ms5), whereas $F_2$ and $BC_1$ progenies will segregate for this trait. It is desirable to determine the genotypes of the progenies, and as such, plants can be evaluated for the presence of the mutation itself, or alternatively, for one or more alleles that are linked to and associated with the mutation in the Ms5 gene (i.e. in linkage disequilibrium with the mutation). For example, one or more alleles at 3A markers MP0156, MP0179, MP0182, MP0190, MP0191, MP0192, MP0201, and MP0090 may be detected to determine if a plant has an Ms5 mutation in the homozygous or heterozygous state. Likewise, one or more alleles at 3D markers MP0126, MP0212, MP0127, MP0215 and MP0130 may be detected to determine if a plant carries a non-functional allele of TaLTPG2-3D in the homozygous or heterozygous state. In the case of ms5$_{FS20}$, the mutations arose in the Chris variety; therefore, alleles of Chris located in the vicinity of the Ms5 gene are in linkage disequilibrium with the causal mutation and hence can be evaluated for presence or absence in order to determine if ms5$_{FS20}$ is present. Similarly alleles of Chris located in the vicinity of TaLTPG2-3D are in linkage disequilibrium with the genetic background which permits observation of ms5$_{FS20}$ male sterility. Through marker assisted selection, a plant breeder will be able to follow the presence of the male sterility trait through controlled crosses to obtain, when desired, a new plant containing both a non-functional 3D allele and an Ms5 mutation in either the homozygous or heterozygous state, thereby maintaining the Ms5 mutation. A plant breeder can also utilize markers in the Ms5 and TaLTPG2-3D regions to produce mutant male sterile seed parents that would be used as female, i.e. plants that need pollination by a pollen donor plant, to produce seeds of commercial interest or to produce F$_1$ hybrids that contain an Ms5 mutation in the heterozygous state.

Example 11: Restoring Male Fertility to Wheat Ms5 Homozygous Recessive Plants by Expressing a Transformed Copy of an Ms5 Gene or Ortholog In the previous example, single-nucleotide sequence differences were detected within regions of DNA that correspond to the Ms5 candidate gene from ms5$_{FS20}$ plants. In this example, various strategies are described for restoring male fertility to homozygous recessive ms5 plants. Male-sterile wheat plants containing an ms5 mutation or deletion are restored to male fertility when transformed with a DNA vector containing a functional copy of an Ms5 gene. This demonstrates that the sequence changes within, or deletions of, the candidate Ms5 gene are the causal effect of the male-sterile phenotype.

Although wheat is an allohexaploid containing three related genomes (ABD) with similar gene content, it behaves as a diploid during meiosis. Often the related wheat genomes contain homeologous genes that have similar gene structure and function, requiring triple mutants to result in a loss-of-function phenotype. The wheat male sterility phenotype observed in the ms5$_{FS20}$ mutant segregates at a 3:1 ratio of fertile to sterile plants if homozygous for a non-functional TaLTPG2-3D allele. This indicates that in this mutant, in selected genetic backgrounds, a single recessive locus in the homozygous condition induces a male sterility phenotype and that this locus segregates according to the laws of Mendelian inheritance. The observation of some functional redundancy with the 3D, but not the 3B, Ms5 homeologue indicates that there has been partial divergence of function among the copies of this gene.

Marker development and assessment has shown that the ms5 locus, in selected genetic backgrounds, segregates at a 1:2:1 ratio of homozygous wild type to heterozygous to homozygous mutant. The correlation of phenotypic and genotypic data supports the Mendelian inheritance of the ms5 mutation.

The Mendelian nature of the ms5 mutation will facilitate a simple introgression of a male sterility trait into different genetic backgrounds.

One strategy to restore male fertility to ms5 plants is to express a gene or genes that can overcome the loss of function or activity resulting from Ms5 mutation or deletion. A gene from wheat, or from another plant species, having identical or similar function to Ms5 is used to restore gene activity in transformed wheat plants. For example, as shown in FIG. 1, a gene from barley encodes a protein with high amino acid sequence similarity to the wheat Ms5 gene product, with approximately 90% sequence identity. The barley gene present within SEQ ID NO:36 is introduced into wheat ms5 mutant plants which are additionally homozygous for a non-functional TaLTPG2-3D allele to restore male fertility. This barley gene may be expressed using its native promoter (see SEQ ID NO:37, nucleotides 1-2000) or a non-native promoter, such as a tissue-preferred, constitutive or conditional promoter, to restore male fertility. Other monocot or dicot plants, or hybrid combinations thereof, can also serve as sources of a complementing gene and promoter to restore male fertility to ms5 mutant male-sterile wheat plants.

In another strategy, the wild-type wheat Ms5 gene or a variant (see, for example, SEQ ID NO:16-18, 21, 23-24) is used to restore male fertility to homozygous recessive ms5 plants which are additionally homozygous for a non-functional TaLTPG2-3D allele. The variant Ms5 gene comprises alteration of one or more DNA restriction sites to allow compatibility with DNA vectors used for plant transformation. See, for example, SEQ ID NO:198, which comprises nucleotide changes introduced at positions 1007 and 1584 to facilitate vector construction. The Ms5 gene is introduced into ms5 plants by known plant transformation methods to produce plants containing stably integrated versions of the Ms5 gene for fertility complementation. As an alternative to using the native Ms5 promoter (SEQ ID NO:17, 22, or 30), a promoter variant (for example see SEQ ID NO:198), or other plant, such as SEQ ID NO:37, 42, 47, or 52, or non-plant constitutive, conditional or tissue-preferred promoter is used to express a wild-type or variant version of the Ms5 gene or cDNA for the purpose of restoring male fertility to homozygous recessive ms5 wheat plants. The gene and promoter may be from one source species or from a combination of source species. In some examples, the promoter is a Ms5 promoter from wheat, rice, barley or *Brachypodium*. The genomic Ms5 sequence 3' to the translational stop codon comprises a functional terminator region; see, for example, SEQ ID NO: 20, 27, 35, 40, 45, 50, or 55.

Constructs and Transformation

To restore the fertility of_ms5$_{FS20}$/ms5$_{FS20}$ homozygous mutants, the wheat Ms5 gene under control of the native wheat Ms5 promoter and terminator was linked to a Bar gene under control of the maize ubiquitin promoter (see, e.g., SEQ ID NO:205) and also carrying a Rbcs terminator sequence (TaMs5-UbiBar). This construct was transformed directly into wheat embryos harvested from Ms5/ms5$_{FS20}$ heterozygous plants that were additionally homozygous for a non-functional TaLTPG2-3D allele through *Agrobacterium*-mediated transformation methods as referenced elsewhere herein. Several independent T-DNA insertion events containing TaMs5-UbiBar were obtained for construct evaluation in ms5$_{FS20}$ plants.

T0 Plant Generation and Analysis

T0 wheat plants containing one or more copies of the TaMs5-UbiBar cassette were identified and genotyped as homozygous or heterozygous for the ms5$_{FS20}$ mutation. Selfed seed from these individual plants was counted as a qualitative measure of male fertility. As shown in Table 5, no seed set was observed in ms5$_{FS20}$/ms5$_{FS20}$ homozygous plants lacking the TaMs5-UbiBar cassette. In contrast, seed set was observed when ms5$_{FS20}$/ms5$_{FS20}$ homozygous plants contained a transformed copy of the TaMs5-UbiBar cassette. These results demonstrate that the transformed copy of TaMs5 was functional and able to restore fertility to ms5$_{FS20}$/ms5$_{FS20}$ homozygous male sterile plants.

TABLE 5

Seed set in T0 wheat plants containing a TaMs5 complementation T-DNA insertion.

| T-DNA Insertion Event | ms5$_{FS20}$ genotype | T-DNA copy number | Male Fertility Phenotpye |
|---|---|---|---|
| Event-1 | ms5$_{FS20}$/ms5$_{FS20}$ | 1 | Fertile |
| Event-2 | ms5$_{FS20}$/ms5$_{FS20}$ | 2 | Fertile |
| Event-3 | ms5$_{FS20}$/ms5$_{FS20}$ | 7 | Fertile |
| Event-4 | ms5$_{FS20}$/ms5$_{FS20}$ | 8 | Fertile |
| Event-5 | ms5$_{FS20}$/ms5$_{FS20}$ | 2 | Fertile |
| Event-6 | Ms5$_{FS20}$/ms5$_{FS20}$ | 1 | Fertile |
| Event-7 | Ms5$_{FS20}$/ms5$_{FS20}$ | 2 | Fertile |
| Event-8 | ms5$_{FS20}$/ms5$_{FS20}$ | 1 | Fertile |
| No T-DNA | ms5$_{FS20}$/ms5$_{FS20}$ | 0 | sterile |
| No T-DNA | ms5$_{FS20}$/ms5$_{FS20}$ | 0 | sterile |

T1 Analysis; Molecular and Phenotypic

Inheritance of complementation by TaMs5 T-DNA insertion was shown by analyzing the T1 plants derived from 2 separate T0 plants with independent T-DNA insertions (Event-1 and Event-8). One set of T1 progeny was derived from a T0 plant homozygous for ms5$_{FS20}$ mutation (ms5$_{FS20}$/ms5$_{FS20}$) with TaMs5-UbiBar cassette (Event-1). The second set of T1 progeny was derived from a T0 plant heterozygous for ms5$_{FS20}$ mutation (Ms5$_{FS20}$/ms5$_{FS20}$) with TaMs5-UbiBar cassette (Event-8). Plants from both sets were genotyped for ms5 and the T-DNA insertion (Event-1 or Event-8). In both sets of T1 progeny, all the plants with genotype ms5$_{FS20}$/ms5$_{FS20}$ and T-DNA insertion (Event-1 or Event-8) were fertile as determined by production of seed (Table 6). All the progeny with genotype ms5$_{FS20}$/ms5$_{FS20}$ without the T-DNA insertion were male sterile and did not produce seed. This clearly demonstrates that the TaMs5 complementation T-DNA insertion is able to restore fertility to the ms5$_{FS20}$/ms5$_{FS20}$ mutant plants and this ability is passed on to progeny.

TABLE 6

Fertility of T1 plants with or without a TsMs5 complementation T-DNA insertion.

| T0 Event | T1 Plant | ms5$_{FS20}$ genotype | T-DNA Copy number | Male Fertility Phenotype |
|---|---|---|---|---|
| Event-1 | Plant 1 | homozygous | 2 | Fertile |
| Event-1 | Plant 2 | homozygous | 0 | Sterile |
| Event-1 | Plant 3 | homozygous | 2 | Fertile |
| Event-1 | Plant 4 | homozygous | 0 | Sterile |
| Event-1 | Plant 5 | homozygous | 0 | Sterile |
| Event-1 | Plant 6 | homozygous | 1 | Fertile |
| Event-1 | Plant 7 | homozygous | 2 | Fertile |
| Event-1 | Plant 8 | homozygous | 2 | Fertile |
| Event-1 | Plant 9 | homozygous | 1 | Fertile |
| Event-1 | Plant 10 | homozygous | 0 | Sterile |
| Event-1 | Plant 11 | homozygous | 2 | Fertile |
| Event-1 | Plant 12 | homozygous | 1 | Fertile |
| Event-1 | Plant 13 | homozygous | 1 | Fertile |
| Event-1 | Plant 14 | homozygous | 1 | Fertile |
| Event-1 | Plant 15 | homozygous | 1 | Fertile |
| Event-1 | Plant 16 | homozygous | 0 | Sterile |
| Event-1 | Plant 17 | homozygous | 2 | Fertile |
| Event-1 | Plant 18 | homozygous | 1 | Fertile |
| Event-1 | Plant 19 | homozygous | 1 | Fertile |
| Event-1 | Plant 20 | homozygous | 1 | Fertile |
| Event-1 | Plant 21 | homozygous | 1 | Fertile |
| Event-1 | Plant 22 | homozygous | 0 | Sterile |
| Event-1 | Plant 23 | homozygous | 1 | Fertile |
| Event-1 | Plant 24 | homozygous | 1 | Fertile |
| Event-1 | Plant 25 | homozygous | 1 | Fertile |
| Event-8 | Plant 1 | homozygous | 1 | Fertile |
| Event-8 | Plant 2 | homozygous | 2 | Fertile |
| Event-8 | Plant 3 | homozygous | 0 | Sterile |
| Event-8 | Plant 4 | homozygous | 0 | Sterile |
| Event-8 | Plant 5 | homozygous | 1 | Fertile |
| Event-8 | Plant 6 | homozygous | 1 | Fertile |

In conclusion, analysis of the T0 and T1 plants with the T-DNA insertion containing the native wheat MS5 gene showed that this gene is able to restore fertility to the ms5$_{FS20}$/ms5$_{FS20}$ homozygous recessive mutation. This example is a further proof that the ms5$_{FS20}$ mutation is in the wheat Ms5 gene.

Example 12. Inbred Maintenance and Increase of Wheat Ms5 Male-Sterile Plants Using a Hemizygous Maintainer This example demonstrates that wheat plants homozygous recessive for ms5 and which are additionally homozygous for a non-functional TaLTPG2-3D allele can be maintained as male-sterile plants using a functional copy of Ms5 linked to a seed marker gene and pollen inhibition gene.

It would be advantageous to produce a pure line of male-sterile plants to allow for cross pollination with a different inbred wheat variety to produce hybrid seed. Generally, strategies that incorporate recessive male sterility result in plants that cannot self-pollinate. To accomplish self-pollination and the production of a pure line of male-sterile plants for cross pollination, an expression cassette (Ms5-AA-Red) is constructed which comprises a functional copy of Ms5 linked to the maize PG47 promoter expressing a functional alpha amylase gene (see, for example, SEQ ID NO:26 in U.S. Pat. No. 8,614,367) and further linked to a color-marker gene (for example, encoding a red fluorescent protein) under control of the barley LTP2 promoter (see, e.g., U.S. Pat. No. 5,525,716) and also carrying a PINII terminator sequence. Using biolistic or Agrobacterium-mediated transformation, this construct is transformed directly into embryos derived from self-pollinated Ms5/ms5 wheat plants which are homozygous for a non-functional TaLTPG2-3D allele. Transformed embryos are regenerated into plants. Wheat plants (ms5/ms5) containing single-copy Ms5-AA-Red cassette, which can be identified using markers flanking the ms5 locus as described above, are male-fertile and are allowed to self-pollinate. Due to the action of PG47:AA to inhibit pollen function and thus prevent transmission of the Ms5-AA-Red expression cassette through pollen, seed from this generation of progeny will segregate at a frequency of 1:1 red-fluorescence and non-fluorescence. Progeny grown from red-fluorescing seed are hemizygous for Ms5-AA-Red, homozygous for ms5, and male fertile; these are used to propagate (i.e., "maintain") the male-sterile inbred. Progeny of the non-fluorescing seed do not contain a transformed copy of the Ms5 complementing gene, are homozygous for ms5 and male-sterile. These male-sterile inbreds are used as the female inbred for the production of hybrid seed when planted adjacent to male inbred wheat plants that are wild-type for the Ms5 gene.

Example 13: Targeted Regulation or Mutagenesis of Gene Candidate

For male fertility applications, it may be advantageous to mutate the endogenous Ms/or Ms5 gene or change its expression, such as by methods described in this example.

Introducing an RNA into a living cell has been shown to inhibit expression of a target gene in that cell (Fire et al. 1998; Timmons and Fire 1998; Fire et al. 1999; Mette et al. 2000; Yu et al. 2002; Cigan et al. 2005; Dalakouras et al. 2009; Bae et al. 2010; Cigan et al. 2010; Tang 2013). A skilled artisan will appreciate that the RNA could be expressed within the cell or applied exogenously (Tang 2013). Interfering RNA may target transcription, translation or mRNA stability, thereby changing the expression of the targeted gene. In this example, expression of the Ms5 gene is reduced or silenced by expressing in planta either RNAs that target the promoter region, as has been shown previously in monocots (Cigan et al. 2010) including wheat (U.S. patent application Ser. No. 14/203,698), or RNAs that target the expressed mRNA, either individually or in combination. For the promoter inverted repeat approach, a portion of the Ms5 promoter region may be duplicated, juxtaposed and oriented in tandem in opposite directions and placed under the control of a constitutive, tissue-preferred or conditional promoter in a plant transformation vector, for the purpose of expressing the promoter inverted repeat RNA in plant cells to silence a gene operably linked to the target promoter.

The skilled artisan will further appreciate that changes can be introduced by mutation of the nucleic acid sequences, thereby leading to changes in either the expression of encoded mRNAs or the amino acid sequence of the encoded Ms5 polypeptide, resulting in alteration of the biological activity of the mRNA or protein, respectively, or both. See for example methods described in U.S. patent application Ser. No. 14/463,687 filed on Aug. 20, 2014, incorporated by reference in its entirety herein. Thus, variant nucleic acid molecules can be created by introducing one or more nucleotide substitutions, additions and/or deletions into the corresponding nucleic acid sequence or surrounding sequences disclosed herein. Such variant nucleic acid sequences are also encompassed by the present disclosure.

Variant nucleic acid sequences can be made by introducing sequence changes randomly along all or part of the Ms5 genic region, including, but not limited to, chemical or irradiation mutagenesis and oligonucleotide-mediated mutagenesis (OMM) (Beetham et al. 1999; Okuzaki and Toriyama 2004). Alternatively, or additionally, sequence changes can be introduced at specific selected sites using double-strand-break technologies such as ZNFs, custom designed homing endonucleases, TALENs, CRISPR/CAS (also referred to as guide RNA/Cas endonuclease systems (U.S. patent application Ser. No. 14/463,687 filed on Aug. 20, 2014)), or other protein and/or nucleic acid based mutagenesis technologies. The resultant variants can be screened for altered Ms5 activity. It will be appreciated that the techniques are often not mutually exclusive. Indeed, the various methods can be used singly or in combination, in parallel or in series, to create or access diverse sequence variants.

Example 14: Cytological and Metabolite Analysis of Ms5 and Ms5$_{FS20}$ Pollen Electron and Light Microscopy Sterile (ms5) and fertile (Ms5) mature anthers before dehiscence were fixed with either paraformaldehyde 4%, glutaraldehyde 1.25%, and sucrose 4% in phosphate-buffered saline (PBS) pH 7.4, for 16 h at 4° C. for scanning electron microscopy (SEM) or 3% glutaraldehyde in 0.1 M phosphate buffer pH 7.0 overnight for transmission electron (TEM) or light microscopy. Samples for SEM were rinsed twice with PBS pH 7.4 for 5 min whereas samples for TEM and light microscopy were washed twice with 1×PBS and embedded in 2% low melting point agarose (Sigma, St. Louis, Mo.) in 1×PBS for sample orientation and sectioning, then dehydrated using a series of graded ethanol solutions (30%, 50%, 70%, 85%, 90% and 95%) each for 60 min. Samples were then infiltrated 3 times, each for 60 min, in 100% ethanol. Samples were either embedded in LR white resin, sectioned (2 µm) and stained with 0.05% toluidine blue stain and mounted on slides in DPX solution (Sigma, St. Louis, Mo.) for light microscopy or dissected then critical point dried and sputter coated with platinum (BalTec CPD030 Critical Point Dryer) for SEM. 70-80 nm ultrathin anther sections were prepared and stained in 4% uranyl acetate followed by Reynold's lead citrate (The University of Adelaide microscopy) 43. SEM and image capture was performed at an accelerating voltage of 10 kV (Philips XL20 SEM w EDAX EDS) whereas TEM and image capture was performed on a Phillips CM-1000 TEM (The University of Adelaide microscopy). Light microscopy images were captured using a Zeiss Axio Imager M2 optical microscope (Zeiss, Germany).

Fatty Acid Profiling

Approximately 50 frozen anthers were transferred into pre-chilled cryogenic mill tubes and weighed accurately. A 300 µL aliquot of 1:3:1 chloroform:methanol:water containing 30 µM internal standard (13C1 Myristic acid) was added to each sample tube. Dried samples and a fatty acid calibration mix (Supelco®37 Component FAME Mix) was prepared by adding 25 µL of 2:1 chloroform:methanol followed by shaking at 37° C. for 30 minutes. Samples were then derivatised using 5 µL of Meth-Prep☐|| (Grace Davison Discovery). 1 µL was injected onto the GC column. The GC-MS apparatus comprised of a Gerstel 2.5.2 Autosampler, a 7890A Agilent gas chromatograph and a 5975C Agilent quadrupole mass spectrometer (Agilent, Santa Clara, USA). The mass spectrometer was calibrated according to manufacturer's recommendations using tris-(perfluorobutyl)-amine (CF43).

Gas chromatography was performed on a VF-5MS column (Agilent Technologies, Australia). The injection temperature was set at 250° C., with the MS transfer line at 280° C., the ion source adjusted to 250° C. and the quadrupole at 150° C. Helium was used as the carrier gas at a flow rate of 1.1 mL min-1. The corresponding GC-MS method was performed using the following temperature program; start at injection 50° C., hold for 1 min, followed by a 15° C. min-1 oven temperature ramp to 230° C.; hold for 3 min, followed by a 10° C. ramp to 300° C.

Mass spectra were recorded at 2 scan s-1 with an m/z 50-600 scanning range. Both chromatograms and mass spectra were evaluated using the MassHunter Workstation software version B.07.00 (Agilent, Santa Clara, USA). Retention times and mass spectra (unique qualifier ions) were identified and compared directly to standards from a commercially available fatty acid methyl ester mix (Supelco®37 Component FAME Mix, 47885-U, Sigma-Aldrich). All fatty acid methyl esters identified were quantified using prepared calibration curves from the stock Supelco®37 Component FAME Mix in the linear range from 2.5-150 ®M for each lipid class.

Analysis of ms5 anthers revealed disrupted pollen exine structure, which was first observed in early uninucleate microspores and typified by shallow and incomplete exine surface and reduced electron dense materials at the tapetal cell surface. Furthermore, metabolomic profiling by GC-MS revealed that ms5 anthers accumulate lipid monomers of sporopollenin relative to wild-type. Sterile ms5 anthers containing uninucleate microspores exhibited a five fold increase in C16:0 long chain fatty acids whereas C18ln9c, C18:2n6c and C18:3n6 long chain fatty acids increased 14, 23 and 14 fold respectively (Tables 7 and 8). Taken together this suggests Ms5 is necessary for sporopollenin biosynthesis or transport. Transcriptional profiling of wild-type Ms5 by qRT-PCR using the primers in SEQ SEQ ID NOs: 132-137 revealed the A-genome to be preferentially expressed during early microspore development.

TABLE 7

Fatty Acid profiling of Ms5 fertile anthers

| Fatty Acid | Ms5 Fertile Premeiotic anthers | | Ms5 Fertile Meiotic anthers | | Ms5 Fertile Anthers with Uninucleate Microspores | |
|---|---|---|---|---|---|---|
| | x-fold | sem | x-fold | sem | x-fold | sem |
| C10:0 | 1.000 ± 0.189 | | 0.980 ± 0.088 | | 1.479 ± 0.121 | |
| C11:0 | 1.000 ± 0.251 | | 0.610 ± 0.098 | | 0.872 ± 0.146 | |
| C12:0 | 1.000 ± 0.183 | | 0.992 ± 0.070 | | 1.509 ± 0.108 | |
| C14:0 | 1.000 ± 0.204 | | 0.956 ± 0.047 | | 1.402 ± 0.100 | |
| C15:0 | 1.000 ± 0.193 | | 1.006 ± 0.056 | | 1.533 ± 0.119 | |
| C15:1 | 1.000 ± 0.179 | | 1.009 ± 0.087 | | 1.553 ± 0.117 | |
| C16:0 | 1.000 ± 0.311 | | 1.066 ± 0.196 | | 1.454 ± 0.060 | |
| C16:1 | 1.000 ± 0.214 | | 1.065 ± 0.060 | | 1.801 ± 0.068* | |
| C17:0 | 1.000 ± 0.190 | | 1.026 ± 0.063 | | 1.551 ± 0.094 | |
| C17:1 | 1.000 ± 0.185 | | 1.066 ± 0.059 | | 1.546 ± 0.086 | |
| C18:0 | 1.000 ± 0.139 | | 0.960 ± 0.084 | | 1.315 ± 0.082 | |
| C18:1n9c | 1.000 ± 0.309 | | 2.097 ± 0.274 | | 2.629 ± 0.167* | |
| C18:1n9t | 1.000 ± 0.309 | | 1.295 ± 0.209 | | 2.129 ± 0.025 | |
| C18:2n6c | 1.000 ± 0.443 | | 1.427 ± 0.269 | | 2.599 ± 0.066 | |
| C18:3n3 | 1.000 ± 0.140 | | 0.895 ± 0.092 | | 1.354 ± 0.120 | |
| C18:3n6 | 1.000 ± 0.423 | | 1.282 ± 0.286 | | 1.610 ± 0.105 | |
| C20:0 | 1.000 ± 0.186 | | 1.905 ± 0.196 | | 1.991 ± 0.070* | |
| C20:1 | 1.000 ± 0.256 | | 1.541 ± 0.202 | | 2.128 ± 0.065* | |
| C20:2 | 1.000 ± 0.215 | | 1.106 ± 0.059 | | 1.675 ± 0.060 | |
| C20:4n6 | 1.000 ± 0.181 | | 0.979 ± 0.088 | | 1.580 ± 0.100 | |
| C20:5n3 | 1.000 ± 0.177 | | 1.015 ± 0.076 | | 1.593 ± 0.098 | |
| C21:0 | 1.000 ± 0.188 | | 1.046 ± 0.060 | | 1.599 ± 0.106 | |
| C22 | 1.000 ± 0.199 | | 1.195 ± 0.060 | | 1.722 ± 0.089 | |
| C23:0 | 1.000 ± 0.182 | | 1.055 ± 0.059 | | 1.603 ± 0.105 | |
| C24:0 | 1.000 ± 0.184 | | 1.082 ± 0.060 | | 1.651 ± 0.094 | |
| C24:1 | 1.000 ± 0.182 | | 1.042 ± 0.058 | | 1.589 ± 0.106 | |

TABLE 8

Fatty Acid profiling of ms5 sterile anthers

| ms5 Sterile Premeiotic anthers | | ms5 Sterile Meiotic anthers | | ms5 Sterile Anthers with Uninucleate Microspores | |
|---|---|---|---|---|---|
| x-fold | sem | x-fold | sem | x-fold | sem |
| 1.000 ± 0.107 | | 1.284 ± 0.141 | | 1.494 ± 0.384 | |
| 1.000 ± 0.030 | | 1.272 ± 0.131 | | 1.676 ± 0.440 | |
| 1.000 ± 0.107 | | 1.294 ± 0.139 | | 1.555 ± 0.355 | |
| 1.000 ± 0.086 | | 1.388 ± 0.116 | | 1.765 ± 0.294 | |
| 1.000 ± 0.103 | | 1.322 ± 0.126 | | 1.663 ± 0.332 | |
| 1.000 ± 0.106 | | 1.288 ± 0.141 | | 1.529 ± 0.391 | |
| 1.000 ± 0.216 | | 2.410 ± 0.126* | | 5.679 ± 0.064* | |
| 1.000 ± 0.078 | | 1.489 ± 0.133 | | 2.542 ± 0.077* | |
| 1.000 ± 0.110 | | 1.351 ± 0.124 | | 1.737 ± 0.302 | |
| 1.000 ± 0.101 | | 1.333 ± 0.125 | | 1.734 ± 0.298 | |
| 1.000 ± 0.071 | | 1.389 ± 0.132 | | 2.482 ± 0.127* | |
| 1.000 ± 0.493 | | 5.164 ± 0.174* | | 13.639 ± 0.219* | |
| 1.000 ± 0.175 | | 1.825 ± 0.137 | | 5.674 ± 0.260* | |
| 1.000 ± 0.432 | | 4.896 ± 0.247 | | 22.796 ± 0.341* | |
| 1.000 ± 0.250 | | 0.842 ± 0.124 | | 0.965 ± 0.386 | |
| 1.000 ± 0.558 | | 4.372 ± 0.214 | | 14.104 ± 0.229* | |
| 1.000 ± 0.013 | | 2.333 ± 0.089* | | 3.833 ± 0.122* | |
| 1.000 ± 0.017 | | 2.097 ± 0.080* | | 4.381 ± 0.127* | |
| 1.000 ± 0.283 | | 1.103 ± 0.114 | | 1.685 ± 0.157 | |
| 1.000 ± 0.109 | | 1.284 ± 0.143 | | 1.550 ± 0.367 | |
| 1.000 ± 0.108 | | 1.306 ± 0.144 | | 1.534 ± 0.373 | |
| 1.000 ± 0.104 | | 1.339 ± 0.131 | | 1.637 ± 0.339 | |
| 1.000 ± 0.096 | | 1.456 ± 0.102 | | 2.067 ± 0.226 | |
| 1.000 ± 0.182 | | 1.218 ± 0.130 | | 1.545 ± 0.314 | |
| 1.000 ± 0.106 | | 1.351 ± 0.128 | | 1.760 ± 0.291 | |
| 1.000 ± 0.144 | | 1.265 ± 0.136 | | 1.600 ± 0.311 | |

Tables 7 and 8: Fatty Acid profiling of Ms5 fertile versus ms5 sterile anthers. Mean fatty acid content and associated standard error (SEM) was calculated as concentration in mmol per anther based on three biological replicates and presented as a fold change relative to pre-meiotic anthers for each fertile and sterile anther sample. * indicates those samples that have a T-test value below p<0.05, but not below the Bonferroni corrected p-value.

That which is claimed:

1. A method for producing a male-sterile wheat plant, the method comprising:
   a) introducing a genetic modification into at least one or more endogenous MS5 polynucleotide sequences in a wheat plant cell, wherein the endogenous polynucleotide sequence is selected from the group consisting of:
      (1) a polynucleotide comprising the sequence set forth in SEQ ID NO: 16;
      (2) a polynucleotide having at least 95% sequence identity to SEQ ID NO: 16;
      (3) a polynucleotide that encodes a polypeptide having at least 95% sequence identity to SEQ ID NO: 19; and
      (4) a polynucleotide that encodes a polypeptide of SEQ ID NO: 19;
   wherein the genetic modification confers male sterility to a wheat plant from the wheat plant cell; and
   b) obtaining the male-sterile plant from the wheat plant cell.

2. The method of claim 1, wherein said the genetic modification is introduced by a TALEN, a meganuclease, a zinc finger nuclease, or a CRISPR-associated nuclease.

3. The method of claim 2, wherein the genetic modification is introduced by a Cas9 endonuclease guided by at least one guide RNA.

4. The method of claim 1, wherein the genetic modification introduces one or more nucleotide substitutions, additions and/or deletions into the endogenous polynucleotide sequence.

5. The method of claim 1, further comprising crossing the male-sterile plant with a male-fertile plant to produce a hybrid seed.

* * * * *

SEQUENCE LISTING

<160> NUMBER OF SEQ ID NOS: 212

<210> SEQ ID NO 1
<211> LENGTH: 1857
<212> TYPE: DNA
<213> ORGANISM: Triticum aestivum

<400> SEQUENCE: 1

```
atggagagat cccgccgcct gctgctggtg gcgggcctgc tcgccgcgct gctcccggcg      60
gcggcggccg ccttcgggca gcagccgggg gcgccgtgcg agcccacgct gctggcgacg     120
caggtggcgc tcttctgcgc gcccgacatg cccaccgcgc agtgctgcga gcccgtcgtc     180 gccgcgtcg acctcggcgg cggggtcccc tgcctctgcc gcgtcgccgc ggagccgcag     240
```

```
ctcgtcatgg cgggcctcaa cgccacccac ctcctcacgc tctacagctc ctgcggcggc      300
ctccgtcccg gcggcgccca cctcgccgcc gcctgcgaag gtacgcgcac gttcaccgcc      360
ctccgtccct ccctctctct gtctacgtgc agattttctg tgctctcttt cctgcttgcc      420
tagtacgtag tgttccatgg cctctcgggc cgctagcgct ccgatttgcg ttggtttcct      480
tgctgttctg ccggatctgt tggcacggcg cgcggcgtcg ggttctcgcc gtctcccgtg      540
gcgagcgacc tgcgcagcgc gcgcggcctg gctagcttca taccgctgta ccttgagata      600
cacggagcga tttagggtct actctgagta tttcgtcatc gtaggatgca tgtgccgctc      660
gcgattgttt catcgatttg agatctgtgc ttgttcccgc gagttaagat ggatctagcg      720
ccgtacgcag atgcagagtc tgttgctcga gttaccttat ctaccgtcgt cgactatgg       780 tatttgcctg cttccttttg gctgggttta tcgtgcagta gtagtagaca tgtggacgcg      840
ttcttcttat tttgtgccga ccatcgtcga gatactttc ctgctacagc gtttcatcgc       900
ctgcaccatc ccgttcgtga tagcactttt gtgtcaaacc gcaacgcagc tttgctttct      960
gcggtatctt ctgccttgtt tgtcgccttg cttggtcaaa actgagaact cttgctgttt      1020
gatcgaccga gggcagaggc agagcaagag cctgccgtgc ttttggctct gcagtgcgtc      1080
gtctctgcct ccttttgccaa acatttccat gttgatcctc tgggggcact gcttttttcgc     1140 atgcggtttc cgtagccttc ctctttcatg aaaaaaggtt tgggtcaaat caaatggatc      1200
gcctattggc agagcagcag cagatagctg gctgtctcac agctttggca gaatcggtct      1260
gttgcctgcc accgtgtctc ttatcttgcc tgccaccgtg tctctttttct tgttgcgcac     1320 gtcgtcacct cctcctactt ctttttccagt tttgtttact tttgatgaaa tacggacgaa      1380
cggctggtaa tcattaactt tggttgctgt tgttactgtg gattttggac gcaggacccg      1440
ctcccccggc cgccgtcgtc agcagccccc cgccccccgcc accgtcgacc gcacctcgcc      1500
gcaagcagcc agcgcgtgcg tacctctccc tctcgcccgc atctcgctcc gtattaactg      1560
attgtgtctg catactgacg tgtgctttgg ctttggatct gtttcgcaga cgacgcacca      1620
ccgccgccgc cgccgtccag cgacaagccg tcgtccccgc cgccgtccca ggaacacgac      1680
ggcgccgctc cccacgccaa ggccgccccc gcccaggcgg ctacctcccc gctcgcgccc      1740
gctgctgcca tcgccccgcc gccccaggcg ccacactccg ccgcgcccac ggcgtcatcc      1800
aaggcggcct tcttcttcgt cgccacggcc atgctcggcc tctacatcat cctctga        1857

<210> SEQ ID NO 2
<211> LENGTH: 1997
<212> TYPE: DNA
<213> ORGANISM: Triticum aestivum

<400> SEQUENCE: 2
ttctgcaaaa atctccacta gccattgcat aagctcagga aaattacctt tatgtagtga       60
aacttctctc catcatgttc acgaaaatct aacccttgac aaaaaaggaa cctcgggcat      120
taaaaggaat atgtcaggcc agctctatat aaaaccttgt ctcgtttgat ggttgaacaa      180
aatgactcta tgattgttgt gtttgctgca atgaagaaat tgtatttctc ttgtgctttg      240
ttacgtgcac actgcactat tgatttcacc gacatgtttc acaaaactat ccttgtgatt      300
ctaatttcta agtcacccat tcaccaaaaa tctccaccaa catgcaaatt atcattgaaa      360
agataacata caagcataaa gcaccatcta gttctttact atactcaagc caactataag      420
acttaaacca tttagctaca aatattgttg cacacctccg gtggggtgtt gtggaaaagc      480
```

```
atatttttc ggtcaacaag cccctttgc aatgtatcct cttctaatcc tattcggacc    540
attaacatca taagttgcga ttggcatcct cttcctagga tcagattcac tcaatcgaac    600
atcataaact gcatcttcaa tgtcacccat ttcctatatt ttttcagatt attggcttgc    660
ttcgttcgca atattaggta ctgtgattgg acttctgttg atgccactaa taatttgcag    720
ttgttgcgga atatgaactc aaggggagct catggtgcta tgaagttgat tcggtgggaa    780
attgttctac atccgcactt gctgctcaac ctaaatacat gggttggatt tcttcccaac    840
tttagtacat aaagttctca aattaatgtt ctactacatt aaaattgaaa tccgcaaaca    900
tttttttagta cccaaacatt tttctaatat acggtgaaca ttttcatct actgattttt    960
tgatatatgg tgaaaattgg tgtaatatat gctggcatgt ttttaaatac tacatattga    1020
ccatgtagat aaaaaattta tagtatatga tgaacatttt tgtaatatag atggccattt    1080
ttaaaatata cattgcacat tttataatat acgatgagca gtttataata ctagatgaac    1140
cttttttgga gttctgaaca ttttttttgaa aacagcagcc attgtacaag aaaaaaccaa    1200
aacaaaagaa atgagaaacc caaaacaaa aacaaaacaa aacaaacag agaaacctac    1260
agaaaaaaac gaaacagaaa aaggcaaagg aagaacccga actgggccag ccggctcggc    1320
gtgccccagt gggccgtcgt ggcgaatgca acggctacat gggccgctct tcgtgaaaga    1380
gaaggaggtc agttcatgga ccgctaccag tacacgggcc tcgctgtggc aacacccgcc    1440
gtgtactagt tttcgcggga atccaatgcc aaaatcgctc cccgcgggaa cccgacgtcg    1500
gtctggtgac ttctggagcc ttccagaaca ctccacaagc tcccagagcc gtctgatcag    1560
atcagcacga agcacgaaca ttggcgcgcg aagatatttt ccttcccgac gacgccacac    1620
tgcatttcat ttgaatttca aaaatcgaaa acggaaaaca cttttctctca tcccgaggag    1680
aggcggttag tgccagagga gcacgagaga ggccaccccc ccccagcca gctcacgtgc    1740
cgtgccctcg caccctgcgc ggccgcatcc gggccgtccg cgcggacagc tggccgcgcc    1800
ccacccgaac cgacgcccag gatcgcgccc gccacccgct tgccttagcg tccacggctc    1860
ctccggctat ataacccgcc cctcacccgc tcccctccg gcattccatt tccgtcccac    1920
caccgcacca ccaccactcc accaaaaccc tagcgggcga gcgagggaga gagagaccac    1980
cccgcccgac cccgccg                                                  1997
```

```
<210> SEQ ID NO 3
<211> LENGTH: 669
<212> TYPE: DNA
<213> ORGANISM: Triticum aestivum

<400> SEQUENCE: 3
```

```
atggagagat cccgccgcct gctgctggtg gcgggcctgc tcgccgcgct gctcccggcg     60
gcggcggccg ccttcgggca gcagccgggg gcgccgtgcg agcccacgct gctggcgacg    120
caggtggcgc tcttctgcgc gcccgacatg cccaccgcgc agtgctgcga gcccgtcgtc    180
gccgccgtcg acctcggcgg cggggtcccc tgcctctgcc gcgtcgccgc ggagccgcag    240
ctcgtcatgg cgggcctcaa cgccacccac ctcctcacgc tctacagctc ctgcggcggc    300
ctccgtcccg gcgcgcccca cctcgccgcc gcctgcgaag acccgctcc ccggccgcc    360
gtcgtcagca gcccccgcc cgccaccg tcgaccgcac ctcgccgcaa gcagccagcg    420
cacgacgcac caccgccgcc gccgccgtcc agcgacaagc gtcgtcccc gccgccgtcc    480
caggaacacg acggcgccgc tcccacgcc aaggccgccc cgcccaggc ggctacctcc    540
ccgctcgcgc ccgctgctgc catcgccccg ccgccccagg cgccacactc cgccgcgccc    600
```

```
acggcgtcat ccaaggcggc cttcttcttc gtcgccacgg ccatgctcgg cctctacatc    660
atcctctga                                                            669

<210> SEQ ID NO 4
<211> LENGTH: 222
<212> TYPE: PRT
<213> ORGANISM: Triticum aestivum

<400> SEQUENCE: 4

Met Glu Arg Ser Arg Arg Leu Leu Leu Val Ala Gly Leu Leu Ala Ala
1               5                   10                  15

Leu Leu Pro Ala Ala Ala Ala Phe Gly Gln Gln Pro Gly Ala Pro
            20                  25                  30

Cys Glu Pro Thr Leu Leu Ala Thr Gln Val Ala Leu Phe Cys Ala Pro
                35                  40                  45

Asp Met Pro Thr Ala Gln Cys Cys Glu Pro Val Val Ala Ala Val Asp
        50                  55                  60

Leu Gly Gly Gly Val Pro Cys Leu Cys Arg Val Ala Ala Glu Pro Gln
65                  70                  75                  80

Leu Val Met Ala Gly Leu Asn Ala Thr His Leu Leu Thr Leu Tyr Ser
                85                  90                  95

Ser Cys Gly Gly Leu Arg Pro Gly Gly Ala His Leu Ala Ala Ala Cys
            100                 105                 110

Glu Gly Pro Ala Pro Pro Ala Ala Val Val Ser Ser Pro Pro Pro
        115                 120                 125

Pro Pro Ser Thr Ala Pro Arg Arg Lys Gln Pro Ala His Asp Ala Pro
    130                 135                 140

Pro Pro Pro Pro Ser Ser Asp Lys Pro Ser Ser Pro Pro Pro Ser
145                 150                 155                 160

Gln Glu His Asp Gly Ala Ala Pro His Ala Lys Ala Ala Pro Ala Gln
                165                 170                 175

Ala Ala Thr Ser Pro Leu Ala Pro Ala Ala Ala Ile Ala Pro Pro Pro
            180                 185                 190

Gln Ala Pro His Ser Ala Ala Pro Thr Ala Ser Ser Lys Ala Ala Phe
        195                 200                 205

Phe Phe Val Ala Thr Ala Met Leu Gly Leu Tyr Ile Ile Leu
    210                 215                 220

<210> SEQ ID NO 5
<211> LENGTH: 1000
<212> TYPE: DNA
<213> ORGANISM: Triticum aestivum

<400> SEQUENCE: 5
gtcgccgacc ccgaggccat ggtccgtcca gttgcagtag aatgctcgtc gtcttgttcc     60
gtttcatgct tgtcgccgtt cgaggttcgt ttctgcagtc cgattgagaa gaagacggtg    120
ggttttgatc gcgtcccgag atttctgttg tcgatcgtag cgtcctggta gtagtagtgt    180
ctggtagcag cagtatgttc atgtgtcctc ggtcgcctag ttttggtctc aagtagtact    240
gtctgtccac cgtgtttgcg tggtcgcgga gaacatcatt gggttttgcg attcctctgg    300
tcagatgaac cactgctatg tgatcgatcg atatgatctg aatggaatgg atcaagtttt    360
gcgttctgct gatgacgtga tgcttcttca gttatattca tgctcgatct atttctgttt    420 ccccccatttg aatttgtgga gcagcagttt ggctttcttt tgttctgcta tggatgaatg    480
```

```
cttcttgcat gcatcttgtc tttgcttaat ttgaactgta gaacggatgc agttctggtt      540
tctgctaatg atgtgatgat tcttcatatg catatgcttt acatgttcat ctcttcaaat      600
ttgtgcagca acagtttgta gctttcattc ggctctgaat gaaatgcctc ttgcatgttg      660
tctttgctta atttgttttt cacggggagc ctgctgcagc tttctgttgc catgttgttt      720
tccacgccag acaaaatag atggtgcggt ttgattcgat cccggttaat tgcttgatgc       780
tagcttctga tcaatccctt catcacgatg ttccggagag ccacatggaa ctggaggggg      840
gagattcaaa ttcatgcatg caaatttgtg ttggtgttgg gtcacgtcaa gcagtcactt      900
tttgcagtat cactcttacc attttatcct tttgttgaaa cctctctcct caccccaaaa      960
gttgatgcaa tagtgctatg cccacccatg ctttttttcat                          1000

<210> SEQ ID NO 6
<211> LENGTH: 1856
<212> TYPE: DNA
<213> ORGANISM: Triticum aestivum

<400> SEQUENCE: 6
atggagagat cccgcgggct gctgctggtg gcggggctgc tggcggcgct gctgccggcg       60
gcggcggcgc agccggggggc gccgtgcgag cccgcgctgc tggcgacgca ggtggcgctc      120
ttctgcgcgc ccgacatgcc gacggcccag tgctgcgagc ccgtcgtcgc cgccgtcgac      180
ctcggcggcg gggtgccctg cctctgccgc gtcgccgccg agccgcagct cgtcatggcg      240
ggcctcaacg ccacccacct cctcacgctc tacagctcct gcggcggcct ccgccccggc      300 ggcgccacc tcgccgccgc ctgcgaaggt acgttgtccg cctcctcccc tccctccctc       360
cctccctctc tctctacgtg ctcgctttcc tgcttaccta gtagtacgta gtttcccatg      420
ccttcttgac tcgctagaag tgctccggtt tgggtctgtt aatttcctcg ctgtactacc      480
ggatctgtcg tcggcacggc gcgcggcgtc gggtcctcgc cttctcccgt ggcgaccgac      540
ctgcgcagcg cgcgcgcggc ctagctagct tcataccgct gtacctcgac atacacggag      600
cgatctatgg tctactctga gtatttcctc atcgtagaac gcatgcgccg ctcgcgattg      660
tttcgtcgat tctagatccg tgcttgttcc cgcgagttag tatgcatctg cgtgcatatg      720
ccgtacgcac gcagatgcag agtctgttgc tcgagttatc tactgtcgtt cgctcgacca      780
tatttgcctg ttaatttcct gttcatcgtg catgcagtag tagtagccat gtccacgcct      840
tcttgttttg aggcgatcat cgtcgagatc catggctttg cttctgcac tatcttctgc       900 cttgttttgt tctccgcagt acgtacgtct tgcttggtca aaactgaaaa acgctttgct      960
gtttgtttga tcggcaagag ctggccgtgc ttttggcacc gcagtgcgtc gcctctgccg     1020
cttttgcgaa acatttccat gttgatcctc tggcggaact actttttcgc gtgcggtttg     1080
cgtggccttc ctctctcgtg aaaagaggtc gggtcaaacc aaatggatcg cctcttggca     1140
gagcagcggc agcagatagc tggcgtctc gcagctttgg cagaaccggt ctgtggccat      1200
ctgtcgccgc ctgccaccgt ttccctgatg tttgtttctc tctcgcctgc cactgtttct     1260
tttcttgttg cgcacgtacg tcgtcacctc ctcctacttt tttgccagtt tgtttacttt     1320
ttgatgaaat atacgatga atcggctggt gattaacttt ggctgctgct gttaattact      1380
gtggattttg gatgcaggac ccgctccccc ggccgccgtc gtcagcagcc cccgccccc     1440 gcctccaccg tccgccgcac ctcgccgcaa gcagccagcg cgtaagaacc tctccctctc     1500
cctctctctc tccctctcgc ctgcatctcg ctatgtttat ccatgtccat atgttgatca     1560
gccttgttta gttactaaca tgtgcaccgg atcgggttct cgcagacgac gcaccaccgc     1620
```

-continued

```
cgccaccgcc gtcgagcgag aagccgtcgt ccccgccgcc gtcccaggac cacgacggcg    1680
ccgccccccg cgccaaggcc gcgcccgccc aggcggccac ctccacgctc gcgcccgccg    1740
ccgccgccac cgccccgccg ccccaggcgc cgcactccgc cgcgcccacg cgccgtcca     1800 aggcggcctt cttcttcgtc gccacggcca tgctcggcct ctacatcatc ctctga        1856
```

<210> SEQ ID NO 7
<211> LENGTH: 2000
<212> TYPE: DNA
<213> ORGANISM: Triticum aestivum

<400> SEQUENCE: 7

```
gcatgaactt attatataat aacttgaccg aaaaactacc aaagctggca tgaggccaaa      60
taacagagtc cattgtctcc gagagcaccg ggaaggaagc agcaagacag tgccaatctt     120
ccaactctac aggggacaac acctatggaa acccaaatcc caattcctat cagagagctc     180
cacgatggag atcactatat ccaaacaata agaaaacaag gttgggaaag agcccgagag     240
aggcccctct ccaacccacc aatcaaaccg aaagcgaaca gaacgaccat ctcccaccac     300
aaacttaact agagacttga actcatcatg aacacgaatc aactggcgcc agaaccggga     360
gcccccagat ccataggcaa acaatgggtt gccggtgggg aaatgtttag ctctcaggat     420
atcccaccat agagtcctag cactagttct ttactatact caagccaact ataagactta     480
aaccatttag ttacaaatat cgatgcacac cttcggtggg gcgttgtgaa aaagcatgtt     540
ttttgggtcg acaagcccct tttgcaacgt atcctcttct aatcctattc agatcattaa     600
catcataagc tgcaattgac atgctcttct gaggatcagg ttcatgcaat taaacatcat     660
aaactgcatc tttgatgtca tccttttcct atattttttc cagattattg gcttgcttcg     720
ttttcaatat caggttctat gattcgactt ctgttgttgc cagtaataat ttgtagttgc     780
tgcggaatat gaactcaagg agagctgatg gtgctatgaa gttgatttga tgggaggttg     840
ttctacacct gcacttgctg ctcgacttaa atacatgcct tggatttctt cccagctcta     900
gtacataata tttttcaaat taatgttcca cgacataaaa tttaaatcca caaacatatt     960
tttagtacat gaacaatttt ctaatatagg gcaaacattt tcatataca aaccgatcat    1020 tttaatatat ggtgaaaatc agtgtaatat atgctgaaat gttttcaaat acatattgaa    1080
catatttata ataaatggtg aacattttt ttaataattg atgaccattt ttaaaatgca    1140
tattgaacat tttataatat acactgtaca gttttataat aatcgacgaa catcttttgg    1200
agttctgaac atttttttca aaaacacaag ccatttccca ggaagaatac aaatgcaaaa    1260
gaaatgagat atccaaaaag caaaaagaa aacaaaaca aaacagagaa acctacagga    1320
aaatccaaac agaaaggca aagaagaac ccgaactggg ccaggcaatg tttccaacgg      1380
cctcgctctt cctgaacaag aaggccagtc agcccatggg ctgctcccag tactcgggcc    1440
ccgctgtggc agcacgccat gtaatagttt tcgcgggaat ccaacgccga aatcgcccgc    1500
agcgggaacc cgacgtcggt ctggtgcgtt ctggcgcctt ccagaactct ccacaggctc    1560
ccgcagccgt ccgatcagat cagcacgaag cacgaacatt ggcgcgcggc gatattttct    1620
ttcctcgccc gacgacggcc gcactgcatt tcattttgaa tttcaaaatt cggaaacgga    1680
aaagctttct cgcatcccga ggcgaggcgg ttacgggcgc cagaggggcc accccaccca    1740
ccccaccccg ccctcacgtg cccgcgcggg ccgcatccgg gccgtccgcg cggacagctg    1800
gccgcgccca gcccgaaccg acgcccagga tcgagcgagg gcggcgcgcc cggggcttgg    1860
```

```
cttagcgtcc acgccacctc cggctatata agccgcccca cacccgctcc ccctccggca    1920
ttccattccg ccaccgcacc accaccacca ccaaaccctc gcgagcgagc gagggagaga    1980
gagaccgccc cgccgcgacg                                                2000
```

<210> SEQ ID NO 8
<211> LENGTH: 663
<212> TYPE: DNA
<213> ORGANISM: Triticum aestivum

<400> SEQUENCE: 8

```
atggagagat cccgcgggct gctgctggtg gcggggctgc tggcggcgct gctgccggcg     60
gcggcggcgc agccggggc gccgtgcgag cccgcgctgc tggcgacgca ggtggcgctc    120
ttctgcgcgc ccgacatgcc gacgcccag tgctgcgagc ccgtcgtcgc cgccgtcgac    180
ctcggcggcg gggtgccctg cctctgccgc gtcgccgccg agccgcagct cgtcatggcg    240
ggcctcaacg ccacccacct cctcacgctc tacagctcct gcggcggcct ccgcccggc    300 ggcgcccacc tcgccgccgc ctgcgaagga cccgctcccc cggccgccgt cgtcagcagc    360
cccccgcccc gcctccacc gtccgccgca cctcgccgca agcagccagc gcacgacgca    420
ccaccgccgc caccgccgtc gagcgagaag ccgtcgtccc cgccgccgtc ccaggaccac    480
gacggcgccg ccccccgcgc caaggccgcg cccgcccagg cggccacctc cacgctcgcg    540
cccgccgccg ccgccaccgc cccgccgccc caggcgccgc actccgccgc gcccacggcg    600
ccgtccaagg cggccttctt cttcgtcgcc acggccatgc tcggcctcta catcatcctc    660
tga                                                                  663
```

<210> SEQ ID NO 9
<211> LENGTH: 220
<212> TYPE: PRT
<213> ORGANISM: Triticum aestivum

<400> SEQUENCE: 9

```
Met Glu Arg Ser Arg Gly Leu Leu Leu Val Ala Gly Leu Leu Ala Ala
  1               5                  10                  15

Leu Leu Pro Ala Ala Ala Ala Gln Pro Gly Ala Pro Cys Glu Pro Ala
                 20                  25                  30

Leu Leu Ala Thr Gln Val Ala Leu Phe Cys Ala Pro Asp Met Pro Thr
             35                  40                  45

Ala Gln Cys Cys Glu Pro Val Val Ala Val Asp Leu Gly Gly Gly
         50                  55                  60

Val Pro Cys Leu Cys Arg Val Ala Ala Glu Pro Gln Leu Val Met Ala
 65                  70                  75                  80

Gly Leu Asn Ala Thr His Leu Leu Thr Leu Tyr Ser Ser Cys Gly Gly
                 85                  90                  95

Leu Arg Pro Gly Gly Ala His Leu Ala Ala Ala Cys Glu Gly Pro Ala
            100                 105                 110

Pro Pro Ala Ala Val Val Ser Ser Pro Pro Pro Pro Pro Pro Pro Ser
        115                 120                 125

Ala Ala Pro Arg Arg Lys Gln Pro Ala His Asp Ala Pro Pro Pro
    130                 135                 140

Pro Pro Ser Ser Glu Lys Pro Ser Ser Pro Pro Ser Gln Asp His
145                 150                 155                 160

Asp Gly Ala Ala Pro Arg Ala Lys Ala Ala Pro Ala Gln Ala Ala Thr
                165                 170                 175
```

```
Ser Thr Leu Ala Pro Ala Ala Ala Thr Ala Pro Pro Gln Ala
        180                 185                 190

Pro His Ser Ala Ala Pro Thr Ala Pro Ser Lys Ala Ala Phe Phe Phe
        195                 200                 205

Val Ala Thr Ala Met Leu Gly Leu Tyr Ile Ile Leu
        210                 215                 220

<210> SEQ ID NO 10
<211> LENGTH: 1000
<212> TYPE: DNA
<213> ORGANISM: Triticum aestivum

<400> SEQUENCE: 10
gtcgcgcgcc gaccccgcga gagaccgtgg tccgtccagt cgcagtagag tagagcgctc      60
gtcgtctcgt tccgtttcgt gcctgtcgcc gttcgaggtt cgtttctgcg tgcagtccgg     120
tcgaagaagc cggtgggttt tgagtactag tggtagtagt agcagcagct atcgtttctg     180
tccgctcgta cgtgtttgcg tggtcgcgga gaacaattaa ttgggtgttt gcagtcctc     240
tggttaagat gaaccactga tgctatgtga tcgatcgatc ggtatgatct gaatggaaat     300
ggatcaagtt ttgcgttctg ctgatgatgt gatccatttg gatctgtgtg gggcaacagt     360
ttcgcttgct tttgctctgc gatgaacgaa tgcttcttgc atgcatcttg tctttgctta     420
atttgaactg tagaacggat gcagtactga tttctgctta tgatgtgacg attcgtcgta     480
cgcatatcat ctcttcaaat ttgtgtagca gctgtttgta gcttccattc tgctatggac     540
gaatgcctgt ttttcacgga gaaccgcgcg cggggaccga tgcggctttg tgttgccatg     600
ttgtttttcca cgccaggaca aaatagatgg tgcggttttg atccccaatc ccaccatcac     660
catgttccgg agagccacat ggaactcacg tcaagcggtc acttttttgca gaatcactct     720
taccatttta cccttttgtt gaaacctctc tcctcatccc caaaagttga tgcaacagtg     780
ctatgcgcgc ccacccatgc ttttttcatat gattgtaaaa tttggatcga ttttatcttt     840
tgaaccctaa gtccggtttta caatctgttt gcatgtttat gttccttgcg gcgaggacca     900
ttaaacaaga ctactattgg atatatttcg acaggctttg aaatccgaat tctaaaacat     960
ggtgagactc tatgagacac aagaatgctc tttagaacac                           1000

<210> SEQ ID NO 11
<211> LENGTH: 1895
<212> TYPE: DNA
<213> ORGANISM: Triticum aestivum

<400> SEQUENCE: 11
atggagagat cccgcggcct gctgctggcg gcgggcctgc tggcggcgct gctgccggcg      60
gcggcggccg cgttcgggca gcagccgggg gcgccgtgcg agcccacgct gctggcgacg     120
caggtggcgc tcttctgcgc gcccgacatg cccacggccc agtgctgcga gcccgtcgtc     180
gccgccgtcg acctcggcgg cggggtgccc tgcctctgcc gcgtcgccgc ggagccgcag     240
ctcgtcatgg cgggcctcaa cgccacccac ctcctcacgc tctacggctc ctgcggcggc     300
ctccgtcccg gcggcgccca cctgccgccc gcctgcgaag gtacgtcgcg cacgttcacc     360
gcctccctcc ctccctcgct ctctctctct ctctctctct ctctctctac gtgccgattc     420
tctgtgttcg cttccctgct tacctagcac gtagttttcc atggcttctc gactcgctgg     480
tcctccgatt tgggtcggtt aatttcctcg ctgtactacc ggatctgtcg gcacggcgcg     540
cggcgtcggg ttctcgccgt ctcccgtggc gagcgacctg cgcagcgcgc gcgcggccta     600
```

-continued

```
gctagcttca taccgctgta ccttcagata cacggagcga tttagggtct actctgagta        660
tttcgtcatc gtaggatgca tgtggcagtc gcgattgttt catcgatttt agatctgtgc        720
ttgttcccgc gagttaagat ggatctagcg ccgtacgcag acgcagatgg tcttgctgtc        780
tctgttgctc gagttatctt atctactgtc gttcgagtat atttgcctgc ttccttttga        840
tctgtgttta tcgtgcagta gcagtagcca tgtccacgcc ttcttgtttc gaggcgatca        900
tcgtcgagat agcgctttgt ttcaaaccgc aacgcagcct ttgctttctg cggtatcttc        960
tgccttgttt ttgttctgtg cagtacgtct tgcttggtca aaagtaaaaa ctcttgctgt       1020
tcgatcgacc gaggcctgat gcagagcaag agctggccgt gcttttcgct ctgcagtgca       1080
tcgcctctgc ctcttttggcc aaacatttcc atgttgatcc tctggtgtgg tactacttttt       1140 ttgcatgcgg tttgcgtagc cttcctcttt cgtgaaaaaa ggtcgggtcg cctattggca       1200
gagcagcagc agcagcaaca gatagctggc tgtctcgcag ctttgacaga accggtctgt       1260
ggccatctgt cgccgcctgc caccgttttcc ctgatgtttg tttctctcgt ctcatctcgc       1320
ctgccactgt ttcttttctt gttgcgcacg tcgtcacctc ctcctacttt ttttttccagt       1380 tttgtttact tttgagatac ggacgaacgg ctggtaatta ctaactttgg ttgctgttgt       1440
tactgtggat tttggacgca ggacccgctc ccccggccgc catcgtcagc agcccccgc        1500 ccccgccacc accgtccgcc gcacctcgcc gcaagcagcc agcgcgtacg aacctctccc       1560
tccctctctc tcgcctgcat ctcgctctgt attagctgat tgtgtttact tactgacgtg       1620
tgctttggct ttggatctgt ttcgcagacg acgcaccgcc gccgccgccg ccgtctagcg       1680
agaagccgtc gtccccgccg ccgtcccagg agcacgacgg cgccgccccc cgcgccaagg       1740
ccgcgcccgc ccaggcgacc acctccccgc tcgcgcccgc tgccgccatc gccccgccgc       1800
cccaggcgcc acactccgcg gcgcccacgg cgtcgtccaa ggcggccttc ttcttcgtcg       1860
ccacggccat gctcggcctc tacatcatcc tctga                                  1895
```

<210> SEQ ID NO 12
<211> LENGTH: 2000
<212> TYPE: DNA
<213> ORGANISM: Triticum aestivum

<400> SEQUENCE: 12

```
ccaaacaaca gagtccactg tctccaagag caccgggaag gaagcagcaa gacggtgcca         60
atcttccaac tctacagggg acaacaccct atggaaaccc aaatcccaat tcctaccaga        120
gagctccgtg atggagatcc ctggatctga gcaataagaa aacaagtttg gaaaagagcc        180
cgagagaggc ccctctccaa cccaccaatc caaccgaaag caaacaaaac gaccatctcc        240
caccacgaac ttaactagag acctgaaatc atcatgaaca tgaatcagct ggcgcaagaa        300
ccgggagccc ccagatccag aggcaaacaa tgggttgcca gtggggaaat atttagcttt        360
caggatatcc caccataggg tcctcgcact agttctttac tatactcaag ccaactataa        420
gacttaaacc atttagctac aaatatcgat gcacacctcc cgtggggtgt tgcggaaaag        480
catgtttttt tggtcgacaa gccccttttca caatgtatcc tcttctaatt ctattcagat        540
cattaacatc agctgtgatt gacatcctct tcccaagatc agattcacgc aattgaacat        600
cataaaccac atcttcaatg tcatcctctt cctatatatt tttagatgat tagcttgctt        660
cgttctcaat atcaggttct atgaatggac ttgagttgat gccactaata atttgtagtt        720
gttgcaaaat gtgaactgaa ggggagctat gaatgaactt gagttgattt gatgggaaat        780
tgttctacac atgcacttgc tgctcaactt aaatacgtgc cttggatttc ttcccaactt        840
```

-continued

| | |
|---|---|
| tagtacataa agttctccaa gtaatgttct actacataaa atttgaaatc tgcaaacatt | 900 |
| ttttagtaca cgaacatttt tctatataca gtgaacattt ttcatctact gattttattt | 960 |
| taatatatgg tgaaaattgg tgtaatatat gctgacatgt ttttaagtac atattgaaca | 1020 |
| tatatataaa atacatgatg aacattttg ttatatatga tgctcatttt ttcaatacat | 1080 |
| attgaacatt ttatattata cgatggacag ttttataata atcaatgaac aacttttgga | 1140 |
| gttctgaaca tgcttttgaa aacacaagac attttccaat aaaaaacaaa acaaaagaaa | 1200 |
| tgagaaaccc aaaaacaaaa acaaaacaaa acagagaaac ctacagaaaa aacgaaacag | 1260 |
| agaaggcaaa gaaagaaccg gaactgggcc agccaactcg gcgtgcccca gtggtccgtc | 1320 |
| gtggcgaatg tttgcaacgg ctacatgggc cgctcctcgt gaaaagaag aaggtcagtc | 1380 |
| catgggctgc taccagtaca cgggcctcgc tgtggcaaac tggcaacacg ccatattagt | 1440 |
| tttcgcggga atccaatgcc gaaaaccacc caccgcggga acccgacgtc ggtctggtga | 1500 |
| cttctggcgc cttccagaac cctccacaag ctcccagagc cgtctgatca gatcagcacg | 1560 |
| aagcacgaag cacgaacatt ggcgcgcgaa gatattttct ttccccagcc tccgcctcgc | 1620 |
| ccgacgacg cgcactgcat ttcatttgaa tttcaaaaat cgaaaacgga aaaactttct | 1680 |
| cgcatcccga ggagaggcgg ttacgcgcgc cagaggagca cgagagaggc caccccacgc | 1740 |
| acccagccag ctcacgtgcc gccctcgcac ccccgcggc cgcatccggg ccgtccgatc | 1800 |
| gcacagctgg ccgcgctcca cccgaaccga cgcccaggat cgcgcccgcc acccgcttgc | 1860 |
| cttcgcgtcc acggctcctc cggctatata acccgccccc cacccgctcc ccctccggca | 1920 |
| ttccaccccca acaccgcatc accaccacca ctccaccaaa ccctagcgac cgagcgagag | 1980 |
| agggagagac cgccccgccg | 2000 |

<210> SEQ ID NO 13
<211> LENGTH: 672
<212> TYPE: DNA
<213> ORGANISM: Triticum aestivum

<400> SEQUENCE: 13

| | |
|---|---|
| atggagagat cccgcggcct gctgctggcg gcgggcctgc tggcggcgct gctgccggcg | 60 |
| gcggcggccg cgttcgggca gcagccgggg gcgccgtgcg agcccacgct gctggcgacg | 120 |
| caggtggcgc tcttctgcgc gcccgacatg cccacgccc agtgctgcga gcccgtcgtc | 180 |
| gccgccgtcg acctcggcgg cggggtgccc tgcctctgcc gcgtcgccgc ggagccgcag | 240 |
| ctcgtcatgg cgggcctcaa cgccacccac ctcctcacgc tctacggctc ctgcggcggc | 300 |
| ctccgtcccg gcggcgccca cctcgccgcc gcctgcgaag acccgctcc cccggccgcc | 360 |
| atcgtcagca gcccccgcc cccgccacca ccgtccgccg cacctcgccg caagcagcca | 420 |
| gcgcacgacg caccgccgcc gccgccgccg tctagcgaga agccgtcgtc cccgccgccg | 480 |
| tcccaggagc acgacggcgc cgccccccgc gccaaggccg cgcccgccca ggcgaccacc | 540 |
| tccccgctcg cgcccgctgc cgccatcgcc ccgccgcccc aggcgccaca ctccgcggcg | 600 |
| cccacggcgt cgtccaaggc ggccttcttc ttcgtcgcca cggccatgct cggcctctac | 660 |
| atcatcctct ga | 672 |

<210> SEQ ID NO 14
<211> LENGTH: 223
<212> TYPE: PRT
<213> ORGANISM: Triticum aestivum

```
<400> SEQUENCE: 14

Met Glu Arg Ser Arg Gly Leu Leu Ala Ala Gly Leu Leu Ala Ala
1               5                  10                 15

Leu Leu Pro Ala Ala Ala Ala Phe Gly Gln Gln Pro Gly Ala Pro
            20                  25                 30

Cys Glu Pro Thr Leu Leu Ala Thr Gln Val Ala Leu Phe Cys Ala Pro
            35                  40                 45

Asp Met Pro Thr Ala Gln Cys Cys Glu Pro Val Val Ala Ala Val Asp
        50                  55                 60

Leu Gly Gly Gly Val Pro Cys Leu Cys Arg Val Ala Ala Glu Pro Gln
65                  70                  75                 80

Leu Val Met Ala Gly Leu Asn Ala Thr His Leu Leu Thr Leu Tyr Gly
                85                  90                 95

Ser Cys Gly Gly Leu Arg Pro Gly Gly Ala His Leu Ala Ala Ala Cys
            100                 105                110

Glu Gly Pro Ala Pro Pro Ala Ala Ile Val Ser Ser Pro Pro Pro
            115                 120                125

Pro Pro Pro Ser Ala Ala Pro Arg Arg Lys Gln Pro Ala His Asp Ala
        130                 135                140

Pro Pro Pro Pro Pro Ser Ser Glu Lys Pro Ser Ser Pro Pro Pro
145                 150                 155                160

Ser Gln Glu His Asp Gly Ala Ala Pro Arg Ala Lys Ala Ala Pro Ala
                165                 170                175

Gln Ala Thr Thr Ser Pro Leu Ala Pro Ala Ala Ile Ala Pro Pro
            180                 185                190

Pro Gln Ala Pro His Ser Ala Ala Pro Thr Ala Ser Ser Lys Ala Ala
            195                 200                205

Phe Phe Phe Val Ala Thr Ala Met Leu Gly Leu Tyr Ile Ile Leu
            210                 215                220

<210> SEQ ID NO 15
<211> LENGTH: 1000
<212> TYPE: DNA
<213> ORGANISM: Triticum aestivum

<400> SEQUENCE: 15
gtggccgacc ccgcaagacc atgtccgtcc agttgcagta gagtagagtg ctcgtcgtct    60
tgttccgttt catgcttgtc gccgttcgag gttcgtctct gcatgcagtc cgatcgaaga   120
agacggtgga ttttgagtag tagctgtcgt tggcaggagt atggagttca tgtgtcctcg   180
gtcgcctagt tttggtctca agtagtgtct gtctgtccgc cgtgtttgcg tggtcgcgga   240
gaagtacaat tggtgggtgt ttgcgattcc tctggttaga tgaaccactg ctatgtgatc   300
gatcgatatg atctgaatgg aatggatcaa gttttgcgtt ccgctgatga tgatgtgata   360
tgcttcttca tgtatatata ttcatgctcg atctatttgt gtttctccga tttgaatctg   420
tgttaagcaa cagtttgtct tgcttctgtt ctgcagcttc tgctatggat ggatgcttct   480
tgcatgcatc ttgtctttgc ttaatttgta gtagaacgga tgcagttttg atctctgctg   540
atgatgtgat gattcttcat atgcatatgc tctgtacatg tctcttcaaa tttgtgtagc   600
aacagtctgt agttctcgtt ctgctctgaa tgaatgcctc ttgcatgttg tctttgctag   660
ctttgtggta gaaatgtaga atgcagacat tgcttccgtc ccaaataatc tgttccttgc   720
ttcgtatata tattgacatg ttgtgcatat aatctgtgaa tgaagttgtg aacagtctt    780
ctttcagaaa aaaagttgt gaacaagtgc ctcacctcac ctacaaggct acaaacacaa   840
```

```
caacaacaga agctggcctc ttcacggaga accgcgcggg gactgctgca gctttctgtt        900
gccatattgt ttttcacgcc aggacaaaat agacggtgcg gtttgattcg atcccggtta        960
attctcaatc ccttcgtcac tatgttccac atggaaccgg                             1000
```

<210> SEQ ID NO 16
<211> LENGTH: 1694
<212> TYPE: DNA
<213> ORGANISM: Triticum aestivum

<400> SEQUENCE: 16

```
atggcccca ccgccctcct catcgtcgtc ctcgccgtcg ctgccctcca cgccccgcc          60
gcctccgccg cgttgtccca ggagccacca gcgacgccgt gcgcggcagc catcgtgtcc       120
ttctcgccgt gcctggcgca cgtcgcggtg gtggcgccgc ccgccctgcc ctcgcccgcg       180
cccaccagcg cctgctgcgc ggcgttcctg cgcgccgttt cctccgggga cggcgaaggc       240
ggcggagggg agggatgctt ctgccacctg ctccgcaacc cgctcctcct cggcttcccc       300
gtcgacgccg cgcgcctcgg cactctcctc cccacctgcg cctccgcgaa aacctccgcc       360
gccacggccg ccgaggccga ggccctcttc gccgacaagt gccgaggtga gaaatctgtc       420
ccttcgtgct ccctatttat gctcgtgcaa tatgtatgct tcgatcaatt ctcgtgcgcc       480
atatgcgcgt gctgtcgcgt tcctgttgtt gatcgccgat cgaagcaaat tttactctgc       540
aaagtcctaa ctactgttgt tctcatgatc cttgtacaac tactttcgta atggttggtt       600
gtaatgcgga ttactgacga gctctgaatg ctactaggga tattagcact tgcattactg       660
aactagtgga atgggggaga acaccgcgg gatttttctt ttgttattaa ggagaagata       720
ctgagtggcc cagacttact tctgcgtttt tgctgcgatt tgtcatgatt accgttgatt       780
taagcagttt gttgggttgc ttgtttgata gtagtagtaa tttcacaaaa tattggcgat       840
atttataaat agctaagggc ttcgttactt ggtggttcct ctcaaagagt tcacaaaagt       900
caattattaa attcaattaa gggggcaagt attagtagta ctggctaact ccatttgcca       960
tttgccaatt gaaacagagc tcaagtcact gcctgagatg cattttacac ctccatcgcc      1020
acctcccgca ccaaaacttt ctccaggtaa atgttctgct gcttgtctaa tgattccata      1080
gcttgttaaa aaaatgatt ccataaatct gtgcccagta atgctatttc ggatttcggt       1140
tgaatgaacc aattggcatt tgggcagaca tgtcatatgt cctctcctac caaatgaaac      1200
ttgaacttgt tttatcttgt ggtgctccat ccatttcgtg ttctatgcca caactgtaca      1260
ggttcaaatg tagtagaac aactaatttt gcatcggata ctctctgcag cctctgttct       1320
gttcctacta attgcaggac cgagtctgtc tttgtgatac tatctgcttt gcgtgcactg      1380
ctcttttagg ttgcagctgc accttctatt ttgttcacct gagcattcca ttttggtcga      1440
ctgaacaccg caagtcctga atatcttttct tgaatcgtcg gtcttacttg gtgtgcacta     1500
gttaaactgc tgtgtatgcc cttgcagctg ccgttacaga accagcgtcc ccgactccga      1560
agatggagga gcattcgacc tcgacgacgc ctgtgtcgga tgatcggtcg ggatccgatg      1620
ccttgtgtgc ctgccgggtc ttccttgtgg ccttggtctt gggagcagca gtcttgatca      1680
cgctgcagtt ctga                                                         1694
```

<210> SEQ ID NO 17
<211> LENGTH: 2000
<212> TYPE: DNA
<213> ORGANISM: Triticum aestivum

<400> SEQUENCE: 17

```
tgctatgctt aatgcttgtc actagggctc gagtgtcatg atttcagatc taaacccttt      60
atgttttat caatatatct gagttcctaa tcctatatgg tagttatgtg cacttttat      120
tgttctgaac cgtagacccc aaggtagcaa catgaaaggg gggattaaag ggttgaaaac     180
attgatcatg aaagagtccc cctctgccta ttacatccac tgttttgcac atcaacttca    240
attggttctt acagccgtgg caaaagaaaa tgaaccatgt tcgtggttct ttgatcatgt    300
ttcttaattg cttaatattc ttggagtttc ttgcaagtga catgacatgc tttgagatgt    360
tagagctcaa aaggttttgg aagcacttga aatgggtgag attgaaagtg aagtgggct     420
aaatcaagag atgggactag ctagacccgg cgatactagt tggggttctc attttaagac    480
cattatgcac attgttagca tgtatccaca atccttgaag tacttgatgc tattggaaaa    540
gatccttcac aaaaaggcga gtggacaaga atatgttgag ttactcatgc ttttgttttc    600
aatcttcgtt tgatgctagt tattcgtggc tatacaaatg agttgtccaa atctttgcaa    660
aagagagatc aagatattgt taatgcaatg acacttgtta gttggcaaaa tagtagaatg    720
caacacatga ggtctcatgg ttgggaagaa tttcttgcaa agatgacctt atttggcaac    780
aaaaatgaca ctgaagttca tttgtggtag atacttata agcctcatgg aagatcacgt     840
cggtattatg aagtacaaac aaatgatgat cattatagaa gagaaatgta tcttggtgtc    900
attgattaaa ccattcaaga gcttgacaat cggtttgatg aggtttacat ggagttactt    960
atttgcatgt tggctttgaa tcccctcaat tcatttgctt ctgacgatgc aatcaaggta   1020
atgagacttg tcgaattcta tcccatggac atatcaagta catatttgat aaggctataa   1080
tttcaacttg ctaattttgt tgatgatacg agacaatacg ataggtttag aaatgcaagt   1140
aatattggtg agctctctat tatgcttgtt gcaacaatga aacatgttct ttatgatttg   1200
gtctacttac tcatcaaatt gatattgatt ttaccgatgg tgactgcgag tgttgaaaga   1260
gtattttgga tcatgaatat agcgaaaagt aagttaagga ctagtatgag tgatgaccgc   1320
ttgaatgatt gcttggtgat atttattgag cgggatgtgt tcatgaaagc atgtgaagat   1380
gacatagttg atgctttcat ggcaatgcaa aacgtagagt tacctactgt tatgattttc   1440
tacttgtgct tcttttcatgt aagactattc gtattgttgg agatttgaat tgaactatcc   1500
ttgttattct ttttgccatg ttttgtttga cacacttgga ttaggtacag aaaaaaatag   1560
tgtgcacgcc cttcgtttta ttcctgggtt gtcattaggc cgtaccagga tcgatcgtgt   1620
cctgttgatt attaagacca cagtgatctg gctcagacgg tagtaaactg gatcgtgtta   1680
atttaggtta agttataatg aaacttctta tcccgcaaaa aagttaatgg aacccctttc   1740
cttcgaaaaa aagataacgg acgaatgccc gcagaaaaac cgagtgttga tgacagctag   1800
cgacaggcac tggatcatca cgagccgtcg gatgtgccca actttgcgcc gcctttgtta   1860
acggacgggc atgatcgctt ttgcaaaccc ctcagcatta cacactcaca ccctaaaacc   1920
accaggcatc atcacctcac cacccatccc gccccgatac gagagagaga gtggggacgg   1980
gtgtgctgag agcctgagac                                               2000
```

<210> SEQ ID NO 18
<211> LENGTH: 642
<212> TYPE: DNA
<213> ORGANISM: Triticum aestivum
<220> FEATURE:
<221> NAME/KEY: misc_feature
<222> LOCATION: (101)..(101)
<223> OTHER INFORMATION: R = G or A -continued

<400> SEQUENCE: 18

```
atggccccca ccgccctcct catcgtcgtc ctcgccgtcg ctgccctcca cgccccgcc      60
gcctccgccg cgttgtccca ggagccacca gcgacgccgt rcgcggcagc catcgtgtcc     120
ttctcgccgt gcctggcgca cgtcgcggtg gtggcgccgc cgccctgcc ctcgcccgcg      180
cccaccagcg cctgctgcgc ggcgttcctg cgcgccgttt cctccgggga cggcgaaggc     240
ggcggagggg agggatgctt ctgccacctg ctccgcaacc cgctcctcct cggcttcccc     300
gtcgacgccg cgcgcctcgg cactctcctc cccacctgcg cctccgcgaa aacctccgcc     360
gccacggccg ccgaggccga ggccctcttc gccgacaagt gccgagagct caagtcactg     420
cctgagatgc attttacacc tccatcgcca cctcccgcac caaaactttc tccagctgcc     480
gttacagaac cagcgtcccc gactccgaag atggaggagc attcgacctc gacgacgcct     540
gtgtcggatg atcggtcggg atccgatgcc ttgtgtgcct gccgggtctt ccttgtggcc     600
ttggtcttgg gagcagcagt cttgatcacg ctgcagttct ga                        642
```

<210> SEQ ID NO 19
<211> LENGTH: 213
<212> TYPE: PRT
<213> ORGANISM: Triticum aestivum

<400> SEQUENCE: 19

Met Ala Pro Thr Ala Leu Leu Ile Val Val Leu Ala Val Ala Ala Leu
1               5                   10                  15

His Ala Pro Ala Ala Ser Ala Ala Leu Ser Gln Glu Pro Pro Ala Thr
            20                  25                  30

Pro Cys Ala Ala Ala Ile Val Ser Phe Ser Pro Cys Leu Ala His Val
        35                  40                  45

Ala Val Val Ala Pro Pro Ala Leu Pro Ser Pro Ala Pro Thr Ser Ala
    50                  55                  60

Cys Cys Ala Ala Phe Leu Arg Ala Val Ser Ser Gly Asp Gly Glu Gly
65                  70                  75                  80

Gly Gly Gly Glu Gly Cys Phe Cys His Leu Leu Arg Asn Pro Leu Leu
                85                  90                  95

Leu Gly Phe Pro Val Asp Ala Ala Arg Leu Gly Thr Leu Leu Pro Thr
            100                 105                 110

Cys Ala Ser Ala Lys Thr Ser Ala Ala Thr Ala Ala Glu Ala Glu Ala
        115                 120                 125

Leu Phe Ala Asp Lys Cys Arg Glu Leu Lys Ser Leu Pro Glu Met His
    130                 135                 140

Phe Thr Pro Pro Ser Pro Pro Ala Pro Lys Leu Ser Pro Ala Ala
145                 150                 155                 160

Val Thr Glu Pro Ala Ser Pro Thr Pro Lys Met Glu Glu His Ser Thr
                165                 170                 175

Ser Thr Thr Pro Val Ser Asp Asp Arg Ser Gly Ser Asp Ala Leu Cys
            180                 185                 190

Ala Cys Arg Val Phe Leu Val Ala Leu Val Leu Gly Ala Ala Val Leu
        195                 200                 205

Ile Thr Leu Gln Phe
    210

<210> SEQ ID NO 20
<211> LENGTH: 1000
<212> TYPE: DNA

<213> ORGANISM: Triticum aestivum

<400> SEQUENCE: 20

```
tggatgttcg acctcgctct tgaaaggtct ttgccctcgc tcttgataca atacttgtgc      60
gcgatgctgc gccattcttg attggacctc ttgttgcata cggtgaggtg ccacgtgatg     120
cagggcatga tattggtata cctgggaact cttcctgacc agtgcagttt gttccgtgcg     180
cgttttgatg acctgacaac gcaagtagta actgttatcc ggtgacataa tcgtatcatt     240
tcaaacatgg tacagattta caatgcag tttagtttct cttgcgattt attactttct      300
gtgaatctgc atgccattct cttgcactcg ctgagagaga cggagaactc actggaattt     360
gttttcacta tacaaatatg cgcagttgca gcacacgcac gaacaaatac aaagtcacac     420
atcattcgca ttttctttc agagttacac atttgaaatg aagggaaga aaaacagaag      480
tagcatcgtc agcggaatga agcattacat gccaattggt tgctgatcag gttcagtctg     540
tggactgaat gtattctagg tacattatat gagcaatgac agtagccctg ctgccacgat     600
cgaggaggcg agaactacgg aggatatccc acgacagagc ttccggtggg cgctggacgg     660
gttgaacatg ctgtcacgcg gtacatctg ccccggcgtc cccactatgc caaacaccgg      720
cgccggctgc acgtacgggt acacgtacgg ctcagccggc ggtggaaggt agtacacggg     780
cgttggttcc ggctccgacg cggtgggta gtagtagtac actggcgtcg gcacaggctc     840
cggcggaggc gggcagtgct gtggctttgg cttcggctcg ggctccggct ccggctgtgg     900
ctcaggctca ggctttggct ccggctctgg ttccggctgt ggctcaggct ttggctctgg     960
ctctggctct ggctccgacg gtggcgggta aggcgctggg                          1000
```

<210> SEQ ID NO 21
<211> LENGTH: 1629
<212> TYPE: DNA
<213> ORGANISM: Triticum aestivum

<400> SEQUENCE: 21

```
atgcccccca ccgccctcct cctcgtcgtc ctcgccgtcg ccgccctcca cgcccctgcc      60
gcctccgccg cgttgtccca ggagccacca gcgacgccgt gcgcggcggc catcgtgtcc     120
ttctcgccgt gcctggcgcc gtcgcggtgg tggcgccgcc cgccctgccc tctcccgcgc     180
ccaccagcgc ctgctgcgcg gcgttcctgc gcgccgtttc gccggggac ggcgaaggcg      240
gcggagggga gggatgcttc tgccacctgc tccgcgaccc gctcctcctc ggcttccccg     300
tcgacgccgc gcgcctcggc gctctcctcc ccacctgcgc ctccgcgaaa acctccgccg     360
ccacggccgt cgaggctgag gccctcttcg ccgacaagtg ccgaggtgag aaatctgtcc     420
cttcgtgctc cctatttatg ctcgtgcaat atgcatgctt cgatcaattc tcgtgcgcca     480
tatgcgcgag ctgtcgcgtt cctgttgttg atcgccgatc gaaacaaatc ttactctgca     540
aagccctaac tactgttgtt ctcatgatcc ttgtacaact actttcgtaa tggttggttg     600
taatgcggat tactgacgag ctctggatgc tactagggat attagtactt gcatttctga     660
actagttgaa tgggggagaa acaccgcggg atttttctttt tgtggcccag acttacttct     720
gcatttttgc tgcgatttgt catgattacc gttcagttaa gcagtttgtt gggttgcttg     780
tttgatagta gtaatttcac aaaatattgg cgatatttat aaatagctaa aggcttcgtt     840
acttggtggt ttctctcaaa gagttcacaa aagtcaatca ttaaatcaat taagggggca     900
agtattagta gtactggcta actccatttg ccattgaaac agagctcaag tcactgcctg     960
agatgcattt tacacctcca tcgccacctc ccgcaccaaa actttctcca ggtaaacgtt    1020
```

```
ctccctcttg tctaatgatt tgataaatct gtgcccagtc tattcgggtt tcggttgaat      1080
aaaccaattg gcatttgggc agcatgttat atggtctctc ctcatcccaa ataaaacttg      1140
aacttgtttt atcttgccgt gctccgtcca ttttgtgctc tatgccgcaa ttgcacaggt      1200
tcaatgatag tagaacacct agttttgcat cgcatactct ctgcagcctc tgttctgttc      1260
ctgctaattg cagtatcgtg tctgtctttg tgatactatc tcctttgcat gcactgcact      1320
tttaggttgc agttgcacgt ttgattctag tttgttcacc tgagcattcc attttggtcg      1380
actgaacacc gcaagtcctg aatatctttc ttgaatcgtc ggtcgtactt cgtgtgcact      1440
agttaaactg ctgtctatgc ccttgcagct gccgttccag aaccagcgtc cccgaagatg      1500
gaggagcatt cgacctcagc gacgcctgtg ccggatgatc ggtcgggatc cgatgccttg      1560
tgtgcctgcc gggtcttcct tgtggccttg gtcttgggag cagcagtctt gatcacgctg      1620
cagttctga                                                             1629
```

<210> SEQ ID NO 22
<211> LENGTH: 2000
<212> TYPE: DNA
<213> ORGANISM: Triticum aestivum

<400> SEQUENCE: 22

```
aacatccgta caagttacat gaccagaaac acgtattttt ttacaagttt gtacaccgcg       60
agccgtccta tgcggatttt tgttgaaaaa ggaccatctg ggcgaatgaa ttgacaaaaa      120
agaccacctg ccgataaatt taacaaaaag gaccccctcg gctgtggcgg caggtgcggc      180
aggcgacacg tggcacctgc cgccacacag caaggcggca gcactgtacc aacgggaatc      240
ggcgctggtg acggaacggc agtggcgtgt ggggcccggc cgccaaggga cgtggcagca      300
gtactgtacc tggggcgcag ccgcctggcg ggctggcggc agccctgttc atggcgctgc      360
tgctctactg cacgctacgc tgattgctac cgctgctgca tgcgctttta gccggccact      420
gctgctgatt ggtactgtta ctgcatgcgt ttttagccgg ccactcatgc tgcatgcaag      480
atgttatttt cttgacatgc acgatgttgt taattttgtc attaaccttt gtgttagagc      540
atgaattaga gttaggatgc agaagatgtt ttagttgaag aaaagataga tcaaggtaag      600
atatacccag taattagtaa ttgaatattg tattattcgg tttgactaat aatcaagtgg      660
aaaaacattt taacatccgt atttatgttt gaaataatca tttttattta atatcattcg      720
gttcgactgg aaacataata atatgatgat aacatttaaa tagtatgact taataaataa      780
ccgtatttcc gttagcaata atcggtttgc ttttagtatc atttgcttag aatttaaaca      840
taatagtttg tttacggata ataatacgac aaatattcaa agcagcggta acatcattcg      900
caacagtaca tcaatataaa aaatattcat aatattacac ggcgtcattt atacctcagc      960
ttcgatatgg atgtcgttcc gaataaaatt aaccgtcaaa agggagatcg aggatcgaaa     1020 cgcaattct tcaactacgt catctcctcc ttgtttgtta ctcagatgat accttttta      1080 cctaattaca tacatcatta aggatattag cattttataa tatacaaaac ttagattatt      1140
aacaaaataa actacggttt cgtaactata caacttatta atatattttt ttaccacatg      1200
aaataacaac gcattaaatc atccaatgac caataacaac acaaactttt tcttacttac      1260
catattgata aattcttgca tgtcaaacta aatcgataca ttttaaaggc ctaaagctga     1320
tctacaatac tgttaaatat ttgctttact aattcctgct ctaacacaaa ggttaatgat     1380
agaattaaca acatcgtgca tgtcaagaaa ataacatctt gcatgcagca gcagtggccg     1440
```

| | | |
|---|---|---|
| gctaaaagcg catgcagtag cagtaccaat cagcaacagt ggccggctaa aagcgcatgc | 1500 | |
| agcagtagca atcaacgtag taatagagca gcagggccat gaacagggct gccgccagcc | 1560 | |
| cgcgaggcgg ccgctcccca ggtacagtac tgccgccacg cccccttggcg gctgggcccc | 1620 | |
| acacgccgct gccgttccgt cgccagcgcc cattcccgtt ggtacagtgc tgccgcctcg | 1680 | |
| ctgtgtggcg gcaggtgcca cgtgtcgcct gccgcacctg ccgccacagc cgaggggggtc | 1740 | |
| cttttttgtta aatttatcgg catgtggtcc tttttgtcaa ttcattcgcg catgtggtcc | 1800 | |
| ttttcaccaa aaaatctcct atgcgcccac ctttgcgcca tcttgttaaa cccctcagta | 1860 | |
| ttacactttt tttttgcggg gacagtatta cacactcacg ccctaaaacc accaggcatc | 1920 | |
| atcacctcac cacccatccc gccccaatac gagagaaaga gagagagaga gtggggacgg | 1980 | |
| gtgtgctgag agcctgagac | 2000 | |

<210> SEQ ID NO 23
<211> LENGTH: 635
<212> TYPE: DNA
<213> ORGANISM: Triticum aestivum

<400> SEQUENCE: 23

| | | |
|---|---|---|
| atgcccccca ccgccctcct cctcgtcgtc ctcgccgtcg ccgccctcca cgcccctgcc | 60 | |
| gcctccgccg cgttgtccca ggagccacca gcgacgccgt gcgcggcggc catcgtgtcc | 120 | |
| ttctcgccgt gcctggcgcc gtcgcggtgg tggcgccgcc cgccctgccc tctcccgcgc | 180 | |
| ccaccagcgc ctgctgcgcg gcgttcctgc gcgccgtttc cgccggggac ggcgaaggcg | 240 | |
| gcggagggga gggatgcttc tgccacctgc tccgcgaccc gctcctcctc ggcttccccg | 300 | |
| tcgacgccgc gcgcctcggc gctctcctcc ccacctgcgc ctccgcgaaa acctccgccg | 360 | |
| ccacggccgt cgaggctgag gccctcttcg ccgacaagtg ccgagagctc aagtcactgc | 420 | |
| ctgagatgca ttttacacct ccatcgccac ctcccgcacc aaaactttct ccagctgccg | 480 | |
| ttccagaacc agcgtccccg aagatggagg agcattcgac ctcagcgacg cctgtgccgg | 540 | |
| atgatcggtc gggatccgat gccttgtgtg cctgccgggt cttccttgtg gccttggtct | 600 | |
| tgggagcagc agtcttgatc acgctgcagt tctga | 635 | |

<210> SEQ ID NO 24
<211> LENGTH: 324
<212> TYPE: DNA
<213> ORGANISM: Triticum aestivum

<400> SEQUENCE: 24

| | | |
|---|---|---|
| atggccccca ccgccctcct cctcgtggtc ctcgccgtcg ccgccctcca cgcccctgcc | 60 | |
| gcctccgccg cgttgtccca ggagccacca gcgatgcggg attttttcttt tagctcaagt | 120 | |
| cactgcctga gatgcatttt acacctccat cgccacctcc cgcaccaaaa ctttctccag | 180 | |
| ctgccgttcc agaaccagcg tccccgaaga tggaggagca ttcgacctca gcgacgcctg | 240 | |
| tgccggatga tcgtcggga tccgatgcct tgtgtgcctg ccgggtcttc cttgtggcct | 300 | |
| tggtcttggg agcagcagtc ttga | 324 | |

<210> SEQ ID NO 25
<211> LENGTH: 205
<212> TYPE: PRT
<213> ORGANISM: Triticum aestivum

<400> SEQUENCE: 25

Met Pro Pro Thr Ala Leu Leu Leu Val Val Leu Ala Val Ala Ala Leu

```
                1               5                   10                  15
            His Ala Pro Ala Ala Ser Ala Ala Leu Ser Gln Glu Pro Pro Ala Thr
                                20                  25                  30

Pro Cys Ala Ala Ala Ile Val Ser Phe Ser Pro Cys Leu Ala Pro Ser
                            35                  40                  45

Arg Trp Trp Arg Arg Pro Cys Pro Leu Pro Arg Pro Pro Ala Pro
                50                  55                  60

Ala Ala Arg Arg Ser Cys Ala Pro Phe Pro Gly Thr Ala Lys Ala
             65                  70                  75                  80

Ala Glu Gly Arg Asp Ala Ser Ala Thr Cys Ser Ala Thr Arg Ser Ser
                                85                  90                  95

Ser Ala Ser Pro Ser Thr Pro Arg Ala Ser Ala Leu Ser Ser Pro Pro
                            100                 105                 110

Ala Pro Pro Arg Lys Pro Pro Pro Arg Pro Ser Arg Leu Arg Pro
                            115                 120                 125

Ser Ser Pro Thr Ser Ala Glu Ser Ser Ser His Cys Leu Arg Cys Ile
                        130                 135                 140

Leu His Leu His Arg His Leu Pro His Gln Asn Phe Leu Gln Leu Pro
            145                 150                 155                 160

Phe Gln Asn Gln Arg Pro Arg Arg Trp Arg Ser Ile Arg Pro Gln Arg
                            165                 170                 175

Arg Leu Cys Arg Met Ile Gly Arg Asp Pro Met Pro Cys Val Pro Ala
                        180                 185                 190

Gly Ser Ser Leu Trp Pro Trp Ser Trp Glu Gln Gln Ser
                        195                 200                 205

<210> SEQ ID NO 26
<211> LENGTH: 107
<212> TYPE: PRT
<213> ORGANISM: Triticum aestivum

<400> SEQUENCE: 26

Met Ala Pro Thr Ala Leu Leu Leu Val Val Leu Ala Val Ala Ala Leu
1               5                   10                  15

His Ala Pro Ala Ala Ser Ala Ala Leu Ser Gln Glu Pro Pro Ala Met
                20                  25                  30

Arg Asp Phe Ser Phe Ser Ser Ser His Cys Leu Arg Cys Ile Leu His
            35                  40                  45

Leu His Arg His Leu Pro His Gln Asn Phe Leu Gln Leu Pro Phe Gln
        50                  55                  60

Asn Gln Arg Pro Arg Arg Trp Arg Ser Ile Arg Pro Gln Arg Arg Leu
65                  70                  75                  80

Cys Arg Met Ile Gly Arg Asp Pro Met Pro Cys Val Pro Ala Gly Ser
                85                  90                  95

Ser Leu Trp Pro Trp Ser Trp Glu Gln Gln Ser
            100                 105

<210> SEQ ID NO 27
<211> LENGTH: 1000
<212> TYPE: DNA
<213> ORGANISM: Triticum aestivum

<400> SEQUENCE: 27
tggatgttcg acctcgctct tgatacaata cctgtgcatt gctgcgtcat tcttgattgg      60
atcctcttgt tgcatacggt gaagtgccac gtgatgcagc gcgtgatacc tgagaactct    120
```

| | | | | |
|---|---|---|---|---|
| tcctgactag | tgcagtttgt | tctgtgcgcg | ttttggatga | cctgacaacg caagtaactg | 180 |
| ttatccggtg | acatactcgt | atcgtttcaa | acatggtata | gatttataca atgcagtcta | 240 |
| gtttctcttg | cgattttctt | tctgtgaatc | tgcatgccat | ttccttgcgc tcgctgagag | 300 |
| agacgagaac | tcaggagcac | agcacaggag | caaactctca | tgctttcatg gtgcatgacc | 360 |
| ttgctgcgct | agctgcgccg | gtgaccactc | cggtcccggc | ggccaccagt ccccccccc | 420 |
| ccccccccc | ccccccccc | ccccccccc | cccccgggg | cccggcgtcc ccctccgctt | 480 |
| cccatggcct | cgcaagtctc | tctctcggcg | gattcgtctt | cctcgacctc accttccctg | 540 |
| cctagtgccc | cgctgcgctc | catcgtcgtc | gttcctgatg | tcctgggcac gcgcttcggc | 600 |
| cccatcgccc | agggcgctct | cggcccatcg | cgggccccgg | cggcggcctc ttgagcgtgg | 660 |
| caaaccaaga | tggggcgtcg | ccccgcagc | ccggcttctc | cgcctcgccc ccccccccc | 720 |
| ccccccccc | ccccccccc | ccccccccc | ccccccccc | cgcgtcgcca tggcaacacc | 780 |
| ctgcccacct | ccaggccgcc | gaggaccaac | atccctgcgg | tcctccacgg ttgctgctat | 840 |
| aactgcggcg | atgacgggca | catctctgtg | gactgctgga | aggagaccgt ctgcatgcgc | 900 |
| tatggggtg | cgggccacat | cgccagggat | tgcgcctcgc | cccgcgactc ctctccggtg | 960 |
| gacaggcatt | tgccgcgctg | gtcggcggcc | ccggctcagc | | 1000 |

<210> SEQ ID NO 28
<211> LENGTH: 1665
<212> TYPE: DNA
<213> ORGANISM: Triticum aestivum
<220> FEATURE:
<221> NAME/KEY: misc_feature
<222> LOCATION: (25)..(25)
<223> OTHER INFORMATION: S = C or G

<400> SEQUENCE: 28

| | | | | |
|---|---|---|---|---|
| atggccccca | ccgccctcct | cctcstcgtc | ctcgccgtcg | ccgccctcca cgccccccgcc | 60 |
| gccaacgccg | cgttgtccca | ggagccacca | gcgaccccgt | gcgcggcggc catcgtgtcc | 120 |
| ttctcgccgt | gcctggcgca | cgtcgcggtg | gtggcgccgc | ccgccctgcc ctcgcccgcg | 180 |
| cccaccagcg | cctgctgcgc | ggcgttcctg | cgcgccgttt | ccgccgggga cggcgaaggc | 240 |
| ggcggagggg | agggatgcct | ctgccacctg | ctccgcgacc | cgctcctcct cggcttcccc | 300 |
| gtcgacgccg | cgcgcctcgg | cgctctcctc | cccacctgcg | cctccgcgaa aacctccgcc | 360 |
| gccacggccg | tcgaggccga | ggcctcttc | gccgacaagt | gccgaggtga gaaatctgtc | 420 |
| ccttcgtgct | ccctatttat | gctcgtgcaa | tatgtatgct | ccgatcaatt ctcgtgcgcc | 480 |
| atatgcgcgt | gctgtcgcgt | tcctgttgtt | gatcgccgac | cgaaacaaat tttactctgc | 540 |
| aaagtcctaa | ctactgttgt | tctcattatc | ctcgtacaac | tactttcgta atggttggtt | 600 |
| gtaatgcgga | ttactgacga | gctctggatg | ctactaggga | tattagtact tgcatttctg | 660 |
| aactagtgga | tggggagaa | agcgggattt | ttcttttgtg | gcccagactt acttctgcat | 720 |
| ttttgctgcg | atttgtcatg | attaccgttc | agttaagcag | tttgctgggt tgcctgtttg | 780 |
| atagtagtaa | tttcacaaaa | tattggcgat | atttataaat | agctaagggc ttcgttactt | 840 |
| ggtggtttct | ctcaaagagt | tcacaaaagt | caatcattaa | attcaattaa ggggcaagt | 900 |
| attagtagta | ctggctaact | ccatttgcca | tttgccaatt | gaaacagagc tcaagtcact | 960 |
| gcctgagatg | cattttacac | ctccatcgcc | acctcccgca | ccaaaacttt ctccaggtaa | 1020 |
| atgttctgct | gcttgtctaa | tgattccata | gctcgtcaaa | aaaaaatga ttccataaat | 1080 |
| ctgtgcccag | taatgctatt | tcggatttcg | gttgaatgaa | ccaattggca tttgggcaga | 1140 |

```
catgtcatat ttctttcctc ccaaatgaaa cttgaacttg ttttatcttg tggtgctcca    1200
tccatttcgt gctctatgcc gcaactgtac aggttgaaat gatagtagaa catctaattt    1260
tgcatcggat actctctgca gcctctgttc tgtttctact aattgcagga tcgagtctgt    1320
ctttgtgata ctatctgctt tgcgtgcact gctcttttag gttgcagctg caccttctat    1380
tttgttcacc tgagcattcc attttggtcg actgaacacc gcaagtcctg aatatctttc    1440
ttgaatcgtc ggtcgtactt cgtgtgcact agttaaactg ctgtgtatgc ccttgcagct    1500
gccgttccag aaccagcgtc cccgactccg aagatggagg agcattcgac ctcgacgacg    1560
tccatgtcgg atgatcggtc gggatctgat gccttgtgtg cctgccgggt cttccttgtg    1620
gccttggtct tgggagcagc agtcttgatc acgctgcagt tctga                   1665
```

<210> SEQ ID NO 29
<211> LENGTH: 1666
<212> TYPE: DNA
<213> ORGANISM: Triticum aestivum

<400> SEQUENCE: 29

```
atggcccca  ccgccctcct cctcgtcgtc ctcgccgtcg ccgccctcca cgccccgcc      60 gccaacgccg cgttgtcccc aggagccacc agcgaccccg tgcgcggcgg ccatcgtgtc    120
cttctcgccg tgcctggcgc acgtcgcggt ggtggcgccg cccgccctgc cctgcccgc     180 gcccaccagc gcctgctgcg cggcgttcct gcgcgccgtt ccgccgggg acggcgaagg    240 cggcggaggg gagggatgcc tctgccacct gctccgcgac ccgctcctcc tcggcttccc    300
cgtcgacgcc gcgcgcctcg gcgctctcct ccccacctgc gcctccgcga aaacctccgc    360
cgccacggcc gtcgaggccg aggccctctt cgccgacaag tgccgaggtg agaaatctgt    420
cccttcgtgc tccctattta tgctcgtgca atatgtatgc tccgatcaat tctcgtgcgc    480
catatgcgcg tgctgtcgcg ttcctgttgt tgatcgccga ccgaaacaaa ttttactctg    540
caaagtccta actactgttg ttctcattat cctcgtacaa ctactttcgt aatggttggt    600
tgtaatgcgg attactgacg agctctggat gctactaggg atattagtac ttgcatttct    660
gaactagtgg atgggggaga aagcgggatt tttcttttgt ggcccagact tacttctgca    720
tttttgctgc gatttgtcat gattaccgtt cagttaagca gtttgctggg ttgcctgttt    780
gatagtagta atttcacaaa atattggcga tatttataaa tagctaaggg cttcgttact    840
tggtggtttc tctcaaagag ttcacaaaag tcaatcatta aattcaatta aggggggcaag    900 tattagtagt actggctaac tccatttgcc atttgccaat tgaaacagag ctcaagtcac    960
tgcctgagat gcattttaca cctccatcgc cacctcccgc accaaaactt tctccaggta   1020
aatgttctgc tgcttgtcta atgattccat agctcgtcaa aaaaaaaatg attccataaa   1080
tctgtgccca gtaatgctat ttcggatttc ggttgaatga accaattggc atttgggcag   1140
acatgtcata tttctttcct cccaaatgaa acttgaactt gttttatctt gtggtgctcc   1200
atccatttcg tgctctatgc cgcaactgta caggttgaaa tgatagtaga acatctaatt   1260
ttgcatcgga tactctctgc agcctctgtt ctgtttctac taattgcagg atcgagtctg   1320
tctttgtgat actatctgct ttgcgtgcac tgctctttta ggttgcagct gcaccttcta   1380
ttttgttcac ctgagcattc cattttggtc gactgaacac cgcaagtcct gaatatcttt   1440
cttgaatcgt cggtcgtact tcgtgtgcac tagttaaact gctgtgtatg cccttgcagc   1500
tgccgttcca gaaccagcgt cccgactcc gaagatggag gagcattcga cctcgacgac   1560
```

| | |
|---|---|
| gtccatgtcg gatgatcggt cgggatctga tgccttgtgt gcctgccggg tcttccttgt | 1620 |
| ggccttggtc ttgggagcag cagtcttgat cacgctgcag ttctga | 1666 |

<210> SEQ ID NO 30
<211> LENGTH: 2000
<212> TYPE: DNA
<213> ORGANISM: Triticum aestivum

<400> SEQUENCE: 30

| | |
|---|---|
| caatgtgggc acagatggct tcctcctttg cggtcgcccg cgtcgccgcc atgtcggtgg | 60 |
| cgagacgggt ctcgaaggcc cttatcctct ccttcccacg gcgggcacac tggtcccggt | 120 |
| gggactcata gtccacccga tcgatgatgg ggaaggagag attttccggc taccgggtct | 180 |
| gcgatgatcc agcccaaagg attcaagcgc cattgagtcg atgctacgga gtcgcgccgg | 240 |
| acagatcctg ccgtcggcca ggcgctctcc tcccgggagc ggcggagtgc aatgaggaca | 300 |
| accattgctt cctccaaccc gcacgggatg acaccctagt cgacataatc ggactggtcg | 360 |
| gattcagatc cactgcccgc catgccggcg acggccggag aacgccggag gtgagcttgt | 420 |
| gtggcgcagg agagtgtagt gaagtggcta gggtttgctt cggcgagcgg atggggagga | 480 |
| atatatgtgg ggacgggtgg gccaccgcgg gcctgttctg acatggcgga cgcgctaggg | 540 |
| cgcgcctggg tgcccccata tccgttctat atttgggctg gatatgaggg gtgtcggtca | 600 |
| gcccgagcgt atgaggctcg tttgaggcgc ccgcctgggt cgaaatttcg tgaccggtca | 660 |
| gtgaccaggc gacccgtccg gacgtatgag gcgggtttgg agtgccggac tgcagattct | 720 |
| ctaatttttct acttgtgctt cttttcatgt aagactattc gtattctaat tgagcatgtt | 780 |
| tgggatatat tttgtttact aagttgtgag attctaattg agctattcat gtgattcttt | 840 |
| tgccatattt tgtttgacac ttggattagg tagaaaaaaa ttagagtatg cacttccttc | 900 |
| attttactcc tgggtccgca ctgagtcgta gttaggttcg gtcttcttgt gttgatgtta | 960 |
| agaccacagt ctggttcgga tttggctcag atgggcagta aactggatcg tgtttatcca | 1020 |
| agtcaagttg gtaccattaa aagaaatata ctcatttgtt tggaaccgct actcaagaga | 1080 |
| aaggcgaagt gagtggcgac tcagtttctc tccagtttcc ccgacaccgt tgtgggttcc | 1140 |
| ctttcccatc ttcggccgct tcggcagcgg aagggcaggg gaaccccgga tctggttgtc | 1200 |
| tagtgtgtag atagggtgtg ggtatgtgtg cctggcggca acgtcttcat gggagtggtg | 1260 |
| gcgctatgca tggcaataaa gtatccccga tcctccctcc tctcacggcg atcttggtat | 1320 |
| cggcgttgat ggatcagtgg gagtttggtt tggtgctgca gcggcggcag gagtagcacc | 1380 |
| tctggctgtt tgggctctcg gttctttggc ttcggatccg gcgaccatga cctcgtctcc | 1440 |
| gagatgtttg gcagtgatga cttcccgtcc gcgtgattct tgaaggttcg ccgcaatctg | 1500 |
| gcagcgggt tgccggagcg gctacgacgg cacgccatcg gaccatcttg gaggttggag | 1560 |
| aagtgtgaca tcacagggac ctgattgcag tttctttctt tttcatgggt gtcttgtact | 1620 |
| gctggtttgt gcttaattga tcctagtgtt ttttttaaat ccaggtcaag ttaatgggtc | 1680 |
| cctttacccc gtcaaaaaag ttagttaatg gaacccattt cctccggaaa aaaaagataa | 1740 |
| cggacggaat gcccgcagaa aaatcaagtg ttgatgacgg ctagcgattg gcactagatc | 1800 |
| accacgagcc atccgatgca cccaactttg cgccgccttg ttaacggacg ggcatgatcg | 1860 |
| cttttgcaaa cccctcggta tcacacactc acgccctaaa accaccaggc atcatcacct | 1920 |
| caccacccat cccgccccga tacgagagag ggaggagaga gagagagaga gtggggacgg | 1980 |
| gtgtgctgag agcctgagac | 2000 |

<210> SEQ ID NO 31
<211> LENGTH: 642
<212> TYPE: DNA
<213> ORGANISM: Triticum aestivum
<220> FEATURE:
<221> NAME/KEY: misc_feature
<222> LOCATION: (25)..(25)
<223> OTHER INFORMATION: S = G or C

<400> SEQUENCE: 31

```
atggccccca ccgccctcct cctcstcgtc ctcgccgtcg ccgccctcca cgccccgcc      60
gccaacgccg cgttgtccca ggagccacca gcgaccccgt gcgcggcggc catcgtgtcc    120
ttctcgccgt gcctggcgca cgtcgcggtg gtggcgccgc ccgccctgcc ctcgcccgcg    180
cccaccagcg cctgctgcgc ggcgttcctg cgccgttt ccgccgggga cggcgaaggc      240
ggcggagggg agggatgcct ctgccacctg ctccgcgacc cgctcctcct cggcttcccc    300
gtcgacgccg cgcgcctcgg cgctctcctc cccacctgcg cctccgcgaa aacctccgcc    360
gccacggccg tcgaggccga ggccctcttc gccgacaagt gccgagagct caagtcactg    420
cctgagatgc attttacacc tccatcgcca cctcccgcac caaaactttc tccagctgcc    480
gttccagaac cagcgtcccc gactccgaag atggaggagc attcgacctc gacgacgtcc    540
atgtcggatg atcggtcggg atctgatgcc ttgtgtgcct gccgggtctt ccttgtggcc    600
ttggtcttgg gagcagcagt cttgatcacg ctgcagttct ga                       642
```

<210> SEQ ID NO 32
<211> LENGTH: 643
<212> TYPE: DNA
<213> ORGANISM: Triticum aestivum

<400> SEQUENCE: 32

```
atggccccca ccgccctcct cctcstcgtc ctcgccgtcg ccgccctcca cgccccgcc      60
gccaacgccg cgttgtcccc aggagccacc agcgaccccg tgcgcggcgg ccatcgtgtc    120
cttctcgccg tgcctggcgc acgtcgcggt ggtggcgccg ccgcctgc cctcgcccgc     180
gcccaccagc gcctgctgcg cggcgttcct gcgccgtt ccgccgggg acggcgaagg       240
cggcggaggg gagggatgcc tctgccacct gctccgcgac ccgctcctcc tcggcttccc    300
cgtcgacgcc gcgcgcctcg gcgctctcct ccccacctgc gcctccgcga aaacctccgc    360
cgccacggcc gtcgaggccg aggccctctt cgccgacaag tgccgagagc tcaagtcact    420
gcctgagatg cattttacac ctccatcgcc acctcccgca ccaaaacttt ctccagctgc    480
cgttccagaa ccagcgtccc cgactccgaa gatggaggag cattcgacct cgacgacgtc    540
catgtcggat gatcggtcgg gatctgatgc cttgtgtgcc tgccgggtct tccttgtggc    600
cttggtcttg ggagcagcag tcttgatcac gctgcagttc tga                     643
```

<210> SEQ ID NO 33
<211> LENGTH: 213
<212> TYPE: PRT
<213> ORGANISM: Triticum aestivum

<400> SEQUENCE: 33

```
Met Ala Pro Thr Ala Leu Leu Leu Val Val Leu Ala Val Ala Ala Leu
1               5                   10                  15

His Ala Pro Ala Ala Asn Ala Ala Leu Ser Gln Glu Pro Pro Ala Thr
            20                  25                  30
```

```
Pro Cys Ala Ala Ile Val Ser Phe Ser Pro Cys Leu Ala His Val
         35                  40                  45

Ala Val Val Ala Pro Pro Ala Leu Pro Ser Pro Ala Pro Thr Ser Ala
 50                  55                  60

Cys Cys Ala Ala Phe Leu Arg Ala Val Ser Ala Gly Asp Gly Glu Gly
 65                  70                  75                  80

Gly Gly Gly Glu Gly Cys Leu Cys His Leu Leu Arg Asp Pro Leu Leu
                 85                  90                  95

Leu Gly Phe Pro Val Asp Ala Ala Arg Leu Gly Ala Leu Leu Pro Thr
             100                 105                 110

Cys Ala Ser Ala Lys Thr Ser Ala Ala Thr Ala Val Glu Ala Glu Ala
         115                 120                 125

Leu Phe Ala Asp Lys Cys Arg Glu Leu Lys Ser Leu Pro Glu Met His
 130                 135                 140

Phe Thr Pro Pro Ser Pro Pro Ala Pro Lys Leu Ser Pro Ala Ala
145                 150                 155                 160

Val Pro Glu Pro Ala Ser Pro Thr Pro Lys Met Glu Glu His Ser Thr
                 165                 170                 175

Ser Thr Thr Ser Met Ser Asp Asp Arg Ser Gly Ser Asp Ala Leu Cys
             180                 185                 190

Ala Cys Arg Val Phe Leu Val Ala Leu Val Leu Gly Ala Ala Val Leu
         195                 200                 205

Ile Thr Leu Gln Phe
    210

<210> SEQ ID NO 34
<211> LENGTH: 141
<212> TYPE: PRT
<213> ORGANISM: Triticum aestivum

<400> SEQUENCE: 34

Met Ala Pro Thr Ala Leu Leu Val Val Leu Ala Val Ala Ala Leu
 1               5                  10                  15

His Ala Pro Ala Ala Asn Ala Ala Leu Ser Pro Gly Ala Thr Ser Asp
                 20                  25                  30

Pro Val Arg Gly Gly His Arg Val Leu Leu Ala Val Pro Gly Ala Arg
             35                  40                  45

Arg Gly Gly Gly Ala Ala Arg Pro Ala Leu Ala Arg Ala His Gln Arg
         50                  55                  60

Leu Leu Arg Gly Val Pro Ala Arg Arg Phe Arg Gly Arg Arg
 65                  70                  75                  80

Arg Arg Arg Gly Gly Met Pro Leu Pro Pro Ala Pro Arg Pro Ala Pro
                 85                  90                  95

Pro Arg Leu Pro Arg Arg Arg Ala Pro Arg Ser Pro Pro His
             100                 105                 110

Leu Arg Leu Arg Glu Asn Leu Arg Arg His Gly Arg Arg Gly Arg Gly
         115                 120                 125

Pro Leu Arg Arg Gln Val Pro Arg Ala Gln Val Thr Ala
 130                 135                 140

<210> SEQ ID NO 35
<211> LENGTH: 600
<212> TYPE: DNA
<213> ORGANISM: Triticum aestivum

<400> SEQUENCE: 35
```

```
tggatgttcg acctcgctct tgaaaggtct ttgccctcgc tcttgataca atacttgtgc    60
gatttttttt tagaaaagga ggacgacccc tggcctctct gcatctggac gatgcatacg   120
gccattttat taattatatt ggtatacctg agaactcttc ctgatcagtg cagtttgttc   180
cgtgcgcatt ttgatgacct gacagcgcaa gtaattgtta ccggtgacaa taatcgtata   240
atttcaaaca tggtacagat ttatacaatg cagtttagtt tctcttgcga tttattactt   300
tctgtgaatc tgcatgccat tctcttgcgc tcgctgagag agacggagaa ctcactggaa   360
tttattttca ctatacaaat atgcgcattt gcaccacacg cacgaacaaa ttcaaagttc   420
aacatcagtc gcattttctt ttcagagtta cacatttgaa atgaaggggga aaaaaatgaa   480 caggagtagc atcgtcagcg gaatgaagca ttacatacaa attggttgct gatcaggttc   540
agtctgtgga ctgaatgttt tctgggtaca ttatatgagc aatgtcagta gccctgctgc   600
```

<210> SEQ ID NO 36
<211> LENGTH: 1716
<212> TYPE: DNA
<213> ORGANISM: Hordeum vulgare

<400> SEQUENCE: 36

```
atggcccccc ccgccctcct cctcctcgtc ctcgccgtca ccgccctcca cgcccacgcc    60
gcctccgccg cgttgtccca ggagccacca gcgacgccgt gcgcggcagc catcgtgtcc   120
ttctcgccgt gcctggcgca cgtcgccgtg gtcgcgccgc ccgccctgcc ctcgtccgcg   180
cccaccagcg cctgctgcgc ggcgttcctg cgcgccgttt cctccgggga cggcgaaggc   240
gctggcggag gggagggatg cttctgccac ctgctccgcg accgctcct  cctcggcttc   300 cccgtcgacg ccgcgcgcct cggcgctctc ctccccacct gcgcctccgc gaaaacctcc   360
gccgccacgg ccgtggaggc cgaggccctc ttcgccgaca gtgccgaggg tgataaatct   420
gtcccttcgt gctccctata tttgctcgtg cgacatgtat gcttcgatcg attctcgtgc   480
gtcatatgcg cgtcttgtcg cgttcctgtt gttgatcacc gatcgaaaca aattttactc   540
tgcaaacttc taactaatgt tgttctcatg atccttgcac aaccacttcc gtaatggttg   600
tttgtaatgc ggattacaaa cgagctctgg gtgctactag ggatactacc acttgcattc   660
ctgaactagt ggaaagggg agagacaccg tgcgtctttt tcctttgtaa agcagaaaat   720
acaaaatagt gagaggccca gaattacttt gcatttgcg  ctacgatttg tcatgattac   780
catccagtta agctgtttgt tgggttgctt gttttacagt aatttcacaa aattttggcg   840
acatttataa atagctaagg gcgtcattac ttggtggttt ctatcaacga gttcagaaaa   900
gtcaatatta attcagaggg caaatattag tagtactggc taactccatt tgctatctgc   960
caattgaaac agagctcaag tcactgcctg agatgcattt tacacctcca tcgccacctc  1020
ccgcacccaa actttctcca ggtaagcgtt ctcctgcttg tctaatgatt ccataaatct  1080
gtgtgcagta atgctattcg gatttcggtt gaatgaacca attggaattt gggcagacat  1140
gtcatatgtt gaatgtatca attggcattt gggcagacat gtcatatgtt ggatgaaaca  1200
attggcattt gggcagacat gccatatgtt ctctcctcct cccaaattaa accatccatt  1260
tcgtgctata tgccgcaact gtacaggatc aaatgatagt ggaacatctg attttgcatc  1320
gcatactctc tgcagcctct gttctgttcc tactaatcgc aggattgagt ctgtctttgt  1380
gataccatct cctttgcgtg cactgctctt ttagtttgca gctgcacgtt ctagtttgtt  1440
cacctgagca tgccattttg gtcgtctgaa caccgcaagt cctgaatgtc tttcttgaat  1500
catcggtcgt acttggtgcg cactagttaa actgctgtgt atgcccttgc agctgccgtt  1560
```

```
ccagaaccag cgttcccggc tccgaaaatg gaggagcatt cgagctcgac gcctgcgccg   1620
ggtgatcggt cgggatccga tgccgtgtgt gcatgccggg ttttccttgt ggccttggtc   1680
ttgggagcag cagtcttgat cacgctgaac ttctga                             1716
```

<210> SEQ ID NO 37
<211> LENGTH: 2000
<212> TYPE: DNA
<213> ORGANISM: Hordeum vulgare

<400> SEQUENCE: 37

```
agcaccgtag cagtagcaag ggtgcccgcg ctattgatac ggggaaaacc cgcgctactg     60
ctagactttc cctagtagtg accgggcaca ccgttgtgtc tcttcttgga tggtacttgt    120
gatgtacatc atgagggcta tgtaccaaca agtggactct tgtttagtt ttgtcaagga    180 aagacattgt tcgggtgctt acctcaggta tgtaatgtag gacgagtcgt ggcttgacac    240
aaaagttccc taaatcttgt ggataaagtg tgaaacctct acagaatgta aactatttga    300
atagtcatgt ctgcggtcaa ggacagttgg gtgttgcttc ttaaactaca tccaatgttt    360
tacaaaactt gatgtgcgtg tgggaaagaa atacttgagc taagtcaaat gacttggtga    420
gatgatttaa aaatggagtt gttccaaact tattttatat tgatatatgt aacagttcat    480
atggatactc ataaccacat gatgcatgtt ttataagttg ttagaacatg tcattgcagt    540
aaaaattagc tttctgcaaa attacctact tagtgttata ccatgcattt gttttacctt    600
gttctaaaca tgagttggtt gcaagtacat taaaagtact tattggcttg ccactggtta    660
ttttattggt caagcatgaa agaacgagaa tatgatgaag aattccttgg tgacgatcat    720
gcgaattagg tcgtttccta gtcacatgag atatatgtta ttaataatta ccaactccac    780
caagggattg gatgcacttt tagctgcttg agtcctacca ctccgtccgt gagatccgct    840
tcgactgttg gcagtaccgc tagcgttagg cgacgaggag agttcaacga ggcgacatat    900
gaggtgtggg gcaagagcga cgacgaggag gacatcactc gcttcaccaa ggccgcttcc    960
cgttgccacg accacgaagc tggcacgtcc gcgagcgccg ctggcagtaa ggaagagtgg   1020
tgcatggtaa gtcgctatcg ctcgggtcta ggaaggacac cactcttccc atccacctga   1080
aggcaagctt ggcgggttaa taaacgtcgg ggttagctgc tcaagctgcg atggtggagg   1140
ctacagaggc aaagctggag aaggcgaagg caagtgtcat agcttcaatt tccagggctc   1200
atggtggtct ggtagggaac ggatgctaac gatcattttg attaggaatc atacctcgtg   1260
agttccattt ttagttgaaa tatgtctaaa atgtaatgac ttttatcatg ttcatatgaa   1320
atccgtcgtg tttacataaa tcgcttttta tttatttcaa aatccatcaa ttttgcacaa   1380
attccgtccg ttagctcaat tattatccat taattgttag aatatatatg gacaatattg   1440
aatgacggac ttcgacatca gtaaccgtgg atttattccg cggatatatg tccatgaaat   1500
ttgaccacat tgtagtcgtg tacaggaacg gatttaggag gagggggggg gggctagacc   1560
ccctaacaaa ttgattcttc acctatgatt atggttgtta taacaaaaaa aattcacttc   1620
acatgaattt ttccttttcg atgaacaaac ttgcccttc ctatgcatga atgttggctc   1680
cgtcgtgaac gtgtgtggcc caaattggtt gtaaatgtct gtaaactgga ttgcgttgat   1740
ccaggttagg ttgaacccct ctccttgtaa acgagtgttg atgacggctg gcgacaggca   1800
gtggatcatc acgagccgtc cgacgtaggc gactttgcgc cgcctctgtt aacagacggg   1860
cacgatcgct tttgcaaacc cctcggtttt acacactcac gccctaaaac caccaaggca   1920
```

```
tcatcaccca ccacccacgc ccctatacga gagagagaga gagagagagt gtggggacgg    1980
gcgtgctgag agcctgagac                                                2000
```

<210> SEQ ID NO 38
<211> LENGTH: 642
<212> TYPE: DNA
<213> ORGANISM: Hordeum vulgare

<400> SEQUENCE: 38

```
atggccccc ccgccctcct cctcctcgtc ctcgccgtca ccgccctcca cgccacgcc     60 gcctccgccg cgttgtccca ggagccacca gcgacgccgt gcgcggcagc catcgtgtcc    120
ttctcgccgt gcctggcgca cgtcgccgtg gtcgcgccgc ccgccctgcc ctcgtccgcg    180
cccaccagcg cctgctgcgc ggcgttcctg cgcgccgttt cctccgggga cggcgaaggc    240
gctggcggag gggagggatg cttctgccac ctgctccgcg acccgctcct cctcggcttc    300
cccgtcgacg ccgcgcgcct cggcgctctc ctccccacct cgcctccgc gaaaacctcc     360 gccgccacgg ccgtggaggc cgaggccctc ttcgccgaca gtgccgaga gctcaagtca     420 ctgcctgaga tgcattttac acctccatcg ccacctcccg cacccaaact ttctccagct    480
gccgttccag aaccagcgtt cccggctccg aaaatggagg agcattcgag ctcgacgcct    540
gcgccgggtg atcggtcggg atccgatgcc gtgtgtgcat gccgggtttt ccttgtggcc    600
ttggtcttgg gagcagcagt cttgatcacg ctgaacttct ga                       642
```

<210> SEQ ID NO 39
<211> LENGTH: 213
<212> TYPE: PRT
<213> ORGANISM: Hordeum vulgare

<400> SEQUENCE: 39

```
Met Ala Pro Pro Ala Leu Leu Leu Leu Val Leu Ala Val Thr Ala Leu
1               5                   10                  15

His Ala His Ala Ala Ser Ala Ala Leu Ser Gln Glu Pro Pro Ala Thr
            20                  25                  30

Pro Cys Ala Ala Ala Ile Val Ser Phe Ser Pro Cys Leu Ala His Val
        35                  40                  45

Ala Val Val Ala Pro Pro Ala Leu Pro Ser Ser Ala Pro Thr Ser Ala
    50                  55                  60

Cys Cys Ala Ala Phe Leu Arg Ala Val Ser Ser Gly Asp Gly Glu Gly
65                  70                  75                  80

Ala Gly Gly Gly Glu Gly Cys Phe Cys His Leu Leu Arg Asp Pro Leu
                85                  90                  95

Leu Leu Gly Phe Pro Val Asp Ala Ala Arg Leu Gly Ala Leu Leu Pro
            100                 105                 110

Thr Cys Ala Ser Ala Lys Thr Ser Ala Ala Thr Ala Val Glu Ala Glu
        115                 120                 125

Ala Leu Phe Ala Asp Lys Cys Arg Glu Leu Lys Ser Leu Pro Glu Met
    130                 135                 140

His Phe Thr Pro Pro Ser Pro Pro Ala Pro Lys Leu Ser Pro Ala
145                 150                 155                 160

Ala Val Pro Glu Pro Ala Phe Pro Ala Pro Lys Met Glu Glu His Ser
                165                 170                 175

Ser Ser Thr Pro Ala Pro Gly Asp Arg Ser Gly Ser Asp Ala Val Cys
            180                 185                 190

Ala Cys Arg Val Phe Leu Val Ala Leu Val Leu Gly Ala Ala Val Leu
```

```
        195                 200                 205

Ile Thr Leu Asn Phe
    210

<210> SEQ ID NO 40
<211> LENGTH: 1000
<212> TYPE: DNA
<213> ORGANISM: Hordeum vulgare

<400> SEQUENCE: 40
tggatgttgg acggacctcg ctcttgaaag gtctttgccc tcgctcttga tacaatactt      60
gtgcgttgct gcgtcgttct tgattggatc ctcttgttgc atacggtgag gtaccacgtg     120
atgcagggca tgatattgat acttgaaaac tcttcctgac aagtgcagtt tgttctgtgc     180
gcgttttgat gacctgacaa cgcaagtaac tgttatcctt gtggcatact cgtatcgttc     240
caaacatggt acagatttat acaatgcagt ttagtttctc ttgcaattgt ccttctatga     300
atctgcatgc cgttttcttg ggatcactgg aatttttattt tcaccataca aatatgctta     360
attgcaccac acgcatgaac aaaattcagt gttacacatt tgaaatgaag caaacaaaat     420
gaaaaataaa cagggttagc atcgtcagcg gaatgaagca ttacatgcca attggttgct     480
gatcaggttc agtctgtgga cagaatggtt tgtacgaaag ctacacgagc attgacagta     540
gccctgctgc cacaatcgag gaggcgagga ttgcagaaga tatcccacga cacagcttcc     600
ggtgggcgct ggacgggtag aacatgctgt cgcgcgggta catctgcccc ggcgtgccca     660
ctatgccaaa caccggcgcc ggctgcacgt acgggtacac gtacggctca gccggcggtg     720
gaaggtagta cacgggcgtt ggttccggct ccgacggcgg tgggtagtag tacgccggcg     780
tcggcacagc ctccgcggga ggcgggcagt gctgtgtcgc tggctccggc tgtggctccg     840
gccgtggctc cggttccggc tgtggctccg gccgtggctc cggctctggc tcaggctccg     900
gctctgacgg tggcgggtac ttgtactcgt gctgaggagg cgctgggtgg tgcgacggca     960
ttgccggcgg cagcgggtgc ggatccaggt cgcagacgca                          1000

<210> SEQ ID NO 41
<211> LENGTH: 1568
<212> TYPE: DNA
<213> ORGANISM: <Brachypodium distachyon

<400> SEQUENCE: 41
atgggaccca ccgccctcca cgtcgtcatc gccgtcgcgg ccctcctcct cgccgccgcc      60
gcctccgccg cgtcgtccca ggagcctccg gcgacgccgt gcgcggcggc catcgtggcc     120
ttctcgccgt gcctggcgca cgtcgcggtg gtggcgccgc ccgccgtggc cgcgcccgcg     180
cccaccggcg cctgctgcgc ggcgttcctg cgcgccgtct cggccgggga cggcgaaggc     240
ggcggcgggg agggatgctt ctgccacctc gtccgcgacc cgctcctctt cggcttcccc     300
gtcgacgtcg ggcgcctcgg cgcgctcctc cccacctgcg cctccgccaa cgcctccgca     360
gccaccaccg tcgaggccga ggccctcttc gccgacaagt gccgaggtga caaagtccgt     420
cctcccttcc tgctgatatg ctccccatac atgttcgtgt gatatgtatg cttcgatcga     480
ttctcgttct cgctatatat gcgcgtgttc ttcgctcttg attaccgctc cacttaaaag     540
ttacttcacg atccatctcc atagttcctg tgctcgaaat ccttgtggaa ccacatttgt     600
aattaatagt tggtgggaga tgcggagtat cgacgagctc tagatgttat tgggatgtta     660
ttatttgtgc attgagaagt taatcagtta gtttgctcgt accaattctg ttattaatat     720
```

| | |
|---|---:|
| agttctcgtt tattagacaa gaatttcata aatattgggt gatctttgat aattatttat | 780 |
| ttaaggtgtc atttcttggt ggtctctttt aagaagttca tggaagtaaa atgctagaaa | 840 |
| aatcagtggc acaggtgtta ctattctcta attcgaattg caaattgaag cagagctcaa | 900 |
| gtcactgcct gagatgcatt tgtcacctcc atcaccacct cctgcgccaa aactttctcc | 960 |
| aggtaaacat ttttctgct tgtctaatga ttcgttaatc tgtgtccagt aatcccattc | 1020 |
| agaggcacaa aaaggaattg gtacttcggc tcatgcgccg tatgatttct cgcaaactta | 1080 |
| atttgttaaa ctctgcaatg ttctatccat ttcgtgttgt atgaagataa ctgcagaagt | 1140 |
| acagattcaa acttaactgt atcagtttaa aaaaaaaact taactctatg gtaaaccaaa | 1200 |
| tagtttggct actagttgct gcatcgagtc cctctgttat gttcagttgc actgctctgc | 1260 |
| aacgttgtag ctttccagtt tgtcaacctg agtaatcgct gatcgatcat ccattcaggt | 1320 |
| catttgaacg ctgcaatgtc ttttttggaat cgtcagtcat gtacttcgtg tgcacttgtt | 1380 |
| aatctgctgt gcatgtctct gcagctgccg tcccaggacc agcgtcgtcc ccgaaggtgg | 1440 |
| aggcggcgca atcgacgacg tccacgccac gtgatcggtc aggatcggat ggcttgtgtg | 1500 |
| ccttccgggt ttcgctcatg gcgttggtct tcacagcagc agtcttgatc atgttgcagc | 1560 |
| tctggtag | 1568 |

<210> SEQ ID NO 42
<211> LENGTH: 2000
<212> TYPE: DNA
<213> ORGANISM: <Brachypodium distachyon

<400> SEQUENCE: 42

| | |
|---|---:|
| agatttcatc ccacctttgt ggtgtggtga gttggagaat agagcgagcc ttcatggcgt | 60 |
| ctctaacttt gtggtagagt actcatccaa acggagacgt acaccgatcc caataggtga | 120 |
| aactccgatg aaatcttcgt ctccacgtgt ggtatcattt cctattcacc cccgctctag | 180 |
| tcgatcatac cgatctttca ataagcgacg tggatttgta tagattctta tgcaaatcca | 240 |
| cttcacttat ttcggacgga ggggtatatt cacatagatc aacaacacat acagctcgtc | 300 |
| gtgcaccatg agacacaaac tcaagattaa ctagcagcac gtactccact gctcgtacac | 360 |
| tccagcaagc tagcatgtac tcactccttc tcatgttaag tgactcaaat ttgtctaaat | 420 |
| atgaatgtat ctatgtctaa aaaatgtcta aatacataaa tacatgtaat gaaaagtcag | 480 |
| ttaatatgga acggagagag tacaatgcaa ttgtgatcca gtccagcaaa ctacagtact | 540 |
| caactgctag gtcgtacagt ccagcagtac atgcaagttg gggagaaaca gtggctgctg | 600 |
| tcccttcctt cgtgtgattt agagatccac gtatcgcccc gtgcacttta cgtttaaaca | 660 |
| ctgagcttcg ccgtttgtgc gctgtgagtt gatcgacggc tccagattag tggagcaaga | 720 |
| cgctcgggag cagttgagac tttctctatt ttgaaatatt attctcttga catatcaaaa | 780 |
| ttttgttgtt atatcactga aatttcatta tcacatcact atttcattac tatttcaatc | 840 |
| aataacacta cggttgtatg ttggtaaatt caagctcaga attgagattt ggaattgggg | 900 |
| ttcctgaatt ctgttgtttg gatgtccgtg gaattcatag ttggaatttg agtcttattc | 960 |
| attggtattc aactacaacc gaaagagacc tctctcaata ccgagccaga cgcagtgctc | 1020 |
| ctgctaaacg cagccatggt catgggaggc tccctgccga ccaccaccgc tacccgcagc | 1080 |
| cgcctcgtcg ccggccatct ccgcggcctg cagccaccgc gctgccggac atcttcgtgg | 1140 |
| cccgtggcca ctccgccacc ggacatctcc gcgccctgca gacctcgttg tcggccatca | 1200 |
| ccgacgcccg caacgccggc catctccgcc tcctgcaccc atcccgtcgc tggccaccgc | 1260 |

-continued

```
tccgttgatt tatttccttt cttccccaac tccggcgggt cctctcccac ggtgctacct    1320
gcggccaccc atgggaggtt ccctgctgtc gcccatagct aacgccacca tagcacctct    1380
ttttcctcaa ctctggtgac tcctcctccg gcgagacctc ttccatgcgg cggtgctaca    1440
ccgcggacaa gcgttgttgc gtcgatctat gggacaagg tgagcagttt caatgggtga    1500
attggttgct ctcttgattc cattagcaat acttcgcaca accaaacatc aaaattggta    1560
ttggaaccca attcaatcta gaggctagct gattggtatt tagctcaatt caatttcatg    1620
ccttccaata catacatcca gacgaagctt aagatctcaa tatcaccatt attttcgttc    1680
tttggtacgg agtatatact tcgacaacac cttagtttat tttttttag ctggagcgca    1740 tacgccgtta ccgtgtcagg tgtgacggac gaaatgcccg cacgaatcga cagcatgcac    1800
gggtaagatg acagctagca acagcgggta cacaatcatc acgagccatc cgatgggagc    1860
tttgcgccgc ctttgtgagc ggacggacag gatcgctctc ccaaacccct caaattacgt    1920
acggggtcac gcctcgacaa accgtcgtcc ttcctcccta aaccaccgc accaccccag    1980 agagagaggg gcacgcggac                                               2000
```

<210> SEQ ID NO 43
<211> LENGTH: 639
<212> TYPE: DNA
<213> ORGANISM: <Brachypodium distachyon

<400> SEQUENCE: 43

```
atgggaccca ccgccctcca cgtcgtcatc gccgtcgcgg ccctcctcct cgccgccgcc     60
gcctccgccg cgtcgtccca ggagcctccg gcgacgccgt gcgggcggc catcgtggcc    120 ttctcgccgt gcctggcgca cgtcgcggtg gtggcgccgc ccgccgtggc cgcgcccgcg    180
cccaccggcg cctgctgcgc ggcgttcctg cgcgccgtct cggccgggga cggcgaaggc    240
ggcggcgggg agggatgctt ctgccaccctc gtccgcgacc cgctcctctt cggcttcccc    300
gtcgacgtcg ggcgcctcgg cgcgctcctc cccacctgcg cctccgccaa cgcctccgca    360
gccaccaccg tcgaggccga ggccctcttc gccgacaagt gccgagagct caagtcactg    420
cctgagatgc atttgtcacc tccatcacca cctcctgcgc caaaactttc tccagctgcc    480
gtcccaggac cagcgtcgtc cccgaaggtg gaggcggcgc aatcgacgac gtccacgcca    540
cgtgatcggt caggatcgga tggcttgtgt gccttccggg tttcgctcat ggcgttggtc    600
ttcacagcag cagtcttgat catgttgcag ctctggtag                           639
```

<210> SEQ ID NO 44
<211> LENGTH: 212
<212> TYPE: PRT
<213> ORGANISM: Brachypodium distachyon

<400> SEQUENCE: 44

```
Met Gly Pro Thr Ala Leu His Val Val Ile Ala Val Ala Ala Leu Leu
1               5                   10                  15

Leu Ala Ala Ala Ala Ser Ala Ala Ser Ser Gln Glu Pro Pro Ala Thr
            20                  25                  30

Pro Cys Ala Ala Ala Ile Val Ala Phe Ser Pro Cys Leu Ala His Val
        35                  40                  45

Ala Val Val Ala Pro Pro Ala Val Ala Ala Pro Ala Pro Thr Gly Ala
    50                  55                  60

Cys Cys Ala Ala Phe Leu Arg Ala Val Ser Ala Gly Asp Gly Glu Gly
65                  70                  75                  80
```

Gly Gly Gly Glu Gly Cys Phe Cys His Leu Val Arg Asp Pro Leu Leu
              85                  90                  95

Phe Gly Phe Pro Val Asp Val Gly Arg Leu Gly Ala Leu Leu Pro Thr
            100                 105                 110

Cys Ala Ser Ala Asn Ala Ser Ala Ala Thr Thr Val Glu Ala Glu Ala
            115                 120                 125

Leu Phe Ala Asp Lys Cys Arg Glu Leu Lys Ser Leu Pro Glu Met His
        130                 135                 140

Leu Ser Pro Ser Pro Pro Ala Pro Lys Leu Ser Pro Ala Ala
145                 150                 155                 160

Val Pro Gly Pro Ala Ser Ser Pro Lys Val Glu Ala Ala Gln Ser Thr
                165                 170                 175

Thr Ser Thr Pro Arg Asp Arg Ser Gly Ser Asp Gly Leu Cys Ala Phe
            180                 185                 190

Arg Val Ser Leu Met Ala Leu Val Phe Thr Ala Ala Val Leu Ile Met
        195                 200                 205

Leu Gln Leu Trp
    210

```
<210> SEQ ID NO 45
<211> LENGTH: 1000
<212> TYPE: DNA
<213> ORGANISM: <Brachypodium distachyon

<400> SEQUENCE: 45
acgcttgccc tcgctctcga cacacatact tgtgcctgct ccgtgtttct tgatcggctc      60
ctaatgttgg ctatggtgaa gtgtcatgtg atgccgcgtg gcaggcttat aatctctgaa    120
aactcgtcct tactactggt gcagttttc gtatgcgtag tctgacagta caggtaactg     180
ctgattggtg acattcatgt accgttgcaa acatggtagg aacacgtaca atgcagtttt    240
acaccctatc ctttccgaga cacaaaactg aaatgaccgg gatttatttt cactagagta    300
tatagctgcg ccattgcacg gacgaacaaa ttcagctagt gatcataaga gagttgcaca    360
cttgagatta ctggtgcatc tttacatgcc attcggtgtc tgatcaattt gagtcaactg    420
gacgaacaaa ttgtacgcgc ggcacatgac tacataatca gcgacagact gacagtgccc    480
ctgccacgat cgaggaagcg aggaccaaag tggatacccc ttgacaccga ctccggcgag    540
cgctggacgg gttaacgcg cggtcttgcg ggtacatctg cccggggtg cccgttatgc       600
ccatcaccgg cgccggcggc ccgtacgtgt caccccacgg gtactcgtac ggctcagccg    660
gcggcggtag gtaatactct ggctccgacg gcggcgggta gtagtagccc ggcgtcggct    720
caggctccga cggcggtggg tagcaccctg gcgtcggctc aggctccgac ggcggcggat    780
agtactctgg cgtcggctca ggctcagacg gaggcgggta gtactcgcgt tccggcggcg    840
gcgggtggtc agtcggcaga gctggtggaa gcgggtgcgg atccacgtcg cagaggcaca    900
tgaagcactt gcacttgtgg tctgtttcga cccccaatga ccgggacacg accatgcaca    960
tggacacgag gattgttatc ttgagatgca acattttgct                          1000

<210> SEQ ID NO 46
<211> LENGTH: 1772
<212> TYPE: DNA
<213> ORGANISM: Oryza sativa

<400> SEQUENCE: 46
atgggcccca ccgcgctcca cctcatcgcc gtcgccgtcg ccgccgtcgt ggccgcggcg       60
```

```
gcggcaccgg cttcggcgtc ggcgtcggcg gccggggcgt tctcggaggt gccgccggag        120
acgccgtgcg cggcggccat cgtgtcggtg gcgccgtgcc tggcgcacgt cgcggtggtg        180
gcgccgcccg cgcggcccgc gcccgcgccc acggaggcct gctgcgcggc cttcctccgc        240
ggcgtctccc ccagcggcgg cggcggggag gggtgcttct gccacctgct ccgcgacccg        300
ctcctccttg gcttccccgt caacaccgcg aggctcggcg cgctcctccc cacctgcgcc        360
gccgccaacg ccaacgcctc gcggccgcc gccgtcgagg ccgccacgct cttcgccgac         420
acgtgccgag gtcattaccg tgtgccccc ttcttcctcc ttttacatgt ccttgcttcc         480
atcggttttg cgtattcttg tgttcgtgat caccgatcat gttggagaac tactgaacta        540
gtatgtgcat tcacgacggt tggtgataga tgcaaatagt tggcgagccg caagctctag        600
atactactga gagcaaatag attgaaccag ataaatttat tcgagaaatg aaatgaaatt        660
tatttgtgaa cagataaaat ttagtttggt tagtagttac tgggaattgt attactgtgt        720
gaaactattg aattggaaaa cagtgttttgc ctattttttgt gtctatccat aaacgtcaac      780
cttacttcat aaattctcgt tttatccaaa ctactaaaaa gttgcagaga tacaaatgta        840
ggacaaattg atactacggt catcaaggaa atttgcaaat tgcaatgcat gacacacatt        900
gaaagccttg tttggcatca atttcaccaa atttcttgag ctttacaata tttcattctc        960
agataatacg tcattgcttt tctcttagag agttcttaaa actattcact gaacttgatt        1020
tgttaattga catcatgagt tcttgattct ttatcatctt tgtttgtttc accctctaa         1080 agcagacctc aagtcactgc cagagatgcg tttcctacct gacccacctc ccacgccaac        1140
aatttctcca ggtaaacgtt attcagcttg ttcacttatc ctgtgacctt ttggccactg        1200
actccattcg tgagataatc ctcatccgta tcatcctgta cttcgcctct gctcacatgt        1260
tgttttgtct caattttgtg ttatgtgcag ctataaaact atgatagtag aaatttgaac        1320
ttagtaatac cacgaaaaga atcacatacg taattgtgcg atcatggtat actgttactt        1380
gcagcatctc ttctgttgag ttgtaagact tgtaactgtt actaccattt ccagcatgga        1440
gtgtcctgct gatgctatac tatatgtata atcttctcat ctttcagttg taacagtact        1500
ttttagctcc tgtatgacca tgatcatatc gtctatttca tcgtttaatc acagtcacgg        1560
caacgcctat gtggactcgc taatctgttg tgaatgcctg tgcagctgcc gtcccaggat        1620
caatgccccc gacgacggag gagcgttcga cgcccgtgcc tgtgccgcca caggaccggt        1680
ctggatcgga gacctcaact cccagccgga atttccttgt ggtgttgtta gccctaacag        1740
cagcagcagc ggcagatttg atccagctgt ag                                     1772
```

<210> SEQ ID NO 47
<211> LENGTH: 2000
<212> TYPE: DNA
<213> ORGANISM: Oryza sativa

<400> SEQUENCE: 47

```
ttcttggaac actttgacag gttgttgtca gacaaaagat atgaggaagt caaaaatgac        60
tttaagacaa cacaaagtac accatggccg aaagcagatt tgacaatatt aaggcacaac        120
aagaatttat actccagcaa tatttaaagt gtttcaggaa caagtgttgc aaacattgaa        180
ctgtgaccta tactggtgta caaattaaaa gttcgcggta agcaccatta gcatgttgta        240
aaattttctc caacagaagg taagtcagg tgcagctgca agaagtttga atttctcgga         300
atcctatgtt gccatgcatt gaagatactt gatgttaaca atataaaaga aattcctaag        360
```

-continued

| | |
|---|---|
| caatacatac tacaaaggtg gaccattgat gcaaaatctc tacatataaa gagcaactgc | 420 |
| agtactcatg aagatcctaa aataaagtta tcaacgcgca ggagagactt gtgcagaatg | 480 |
| tttgttaaaa tagcatctcg agctgcagaa tctgatgaaa catacttaat ggctgccaac | 540 |
| aatgcacaaa agttagcaga agatgtggag aaatacttga gtataaggcc tgatccagat | 600 |
| ttggataaat ctggtttgta tcctactctg agttgaatag tacttatgct agtgactact | 660 |
| atgttataat ctaaatcagc tatctcaaaa atattttatc ataggcacag aggaaaatgt | 720 |
| tgacccgagt aaagcaagag gcataaaggt taaagagaaa gccattcgtg ggtcgaggag | 780 |
| accaattggt ggttttgaca aggcaacaca acggagtaaa aagaaaaaga gtgattcaaa | 840 |
| cacatcaaag tgtccagtac aagcagaggt ggtaacacca tcactgccat acaccatgat | 900 |
| gcaggtcagt agattcaaga tatacacaca cttggcaaaa gagactctta ttagtgctac | 960 |
| tgattattat ttgccttata cagattcagg gtcgttcaga gattcccact aactacaatc | 1020 |
| acatgcaaat gccagactac tatcatgttg aaggtgcttc attacttcag tcatctggtt | 1080 |
| atttcagaac ttctgaaaaa agtcaaggga tgcagcatga agagactgca cagacatttg | 1140 |
| atacatatcc ctatagcatg tttgcccatt taaattaaaa tccccacctt ttttcatatt | 1200 |
| aattagcacc tttaccaatt tccaatcaca ttacaactta taaggttgga tcttaatctg | 1260 |
| aattcccata tcgattcaag ctgtcaaatc atactagtac tttctcttgt attagcatca | 1320 |
| aatatatggt tcccaccaaa catgttgttt ggctcatata aaaaaaatcc taataattta | 1380 |
| gaagcatcaa aatacaagag gtgtttgcaa aaatgaactt accaaataaa actaccttaa | 1440 |
| tgcagctgta tggtgaaaaa agtttcgatc ttcaattctt cacttcttca ccatagcaaa | 1500 |
| cagtagttgc cagcagcaag ggagttccac atttggtact gaccattaaa ctacaccaag | 1560 |
| ccgacgagta tgcggagtgc agaccacgcc aagccggcga gcccggccgc cgacaacgca | 1620 |
| agagcaacca tggttgcgtg cggccaagag gaagatgagg agagcagcag atgagcagaa | 1680 |
| cttcagatga actctctgat ttggggacaa gagataagga tgcagtggtt ttccaagttg | 1740 |
| tgcagcgcgg agtgaaaagt actagtaccc ggtttgtttt gacggagtag tgacggcgtc | 1800 |
| atattctgca cggcagatag aagccgaccc caccaccaaa aagaatcgac aaaccgatgc | 1860 |
| cctccacgtg gtacggaaca cggatggaaa cacaacaacg gaacagtgaa gccgcagccc | 1920 |
| ctcctccaaa acccctccgt ccccacagac acacggggcc cacctacaga ggcagagagc | 1980 |
| gcgcgccgcg gcgagagcac | 2000 |

<210> SEQ ID NO 48
<211> LENGTH: 666
<212> TYPE: DNA
<213> ORGANISM: Oryza sativa

<400> SEQUENCE: 48

| | |
|---|---|
| atgggcccca ccgcgctcca cctcatcgcc gtcgccgtcg ccgccgtcgt ggccgcggcg | 60 |
| gcggcaccgg cttcggcgtc ggcgtcggcg ccggggcgt tctcggaggt gccgccggag | 120 |
| acgccgtgcg cggcggccat cgtgtcggtg gcgccgtgcc tggcgcacgt cgcggtggtg | 180 |
| gcgccgcccg cgcggccggc gcccgcgccc acggaggcct gctgcgcggc cttcctccgc | 240 |
| ggcgtctccc ccagcggcgg cggcggggag gggtgcttct gccacctgct ccgcgacccg | 300 |
| ctcctccttg gcttccccgt caacaccgcg aggctcggcg cgctcctccc cacctgcgcc | 360 |
| gccgccaacg ccaacgcctc gcggccgcc gccgtcgagg ccgccacgct cttcgccgac | 420 |
| acgtgccgag cagacctcaa gtcactgcca gagatgcgtt tcctacctga cccacctccc | 480 |

```
acgccaacaa tttctccagc tgccgtccca ggatcaatgc ccccgacgac ggaggagcgt        540
tcgacgcccg tgcctgtgcc gccacaggac cggtctggat cggagacctc aactcccagc        600
cggaatttcc ttgtggtgtt gttagcccta acagcagcag cagcggcaga tttgatccag        660
ctgtag                                                                   666
```

<210> SEQ ID NO 49
<211> LENGTH: 221
<212> TYPE: PRT
<213> ORGANISM: Oryza sativa

<400> SEQUENCE: 49

```
Met Gly Pro Thr Ala Leu His Leu Ile Ala Val Ala Val Ala Val
1               5                   10                  15

Val Ala Ala Ala Ala Pro Ala Ser Ala Ser Ala Ala Gly
            20                  25                  30

Ala Phe Ser Glu Val Pro Pro Glu Thr Pro Cys Ala Ala Ile Val
            35                  40                  45

Ser Val Ala Pro Cys Leu Ala His Val Ala Val Val Ala Pro Pro Ala
        50                  55                  60

Arg Pro Ala Pro Ala Pro Thr Glu Ala Cys Cys Ala Ala Phe Leu Arg
65                  70                  75                  80

Gly Val Ser Pro Ser Gly Gly Gly Glu Gly Cys Phe Cys His Leu
                85                  90                  95

Leu Arg Asp Pro Leu Leu Leu Gly Phe Pro Val Asn Thr Ala Arg Leu
                100                 105                 110

Gly Ala Leu Leu Pro Thr Cys Ala Ala Ala Asn Ala Asn Ala Ser Ala
            115                 120                 125

Ala Ala Ala Val Glu Ala Ala Thr Leu Phe Ala Asp Thr Cys Arg Ala
        130                 135                 140

Asp Leu Lys Ser Leu Pro Glu Met Arg Phe Leu Pro Asp Pro Pro
145                 150                 155                 160

Thr Pro Thr Ile Ser Pro Ala Ala Val Pro Gly Ser Met Pro Pro Thr
                165                 170                 175

Thr Glu Glu Arg Ser Thr Pro Val Pro Val Pro Pro Gln Asp Arg Ser
            180                 185                 190

Gly Ser Glu Thr Ser Thr Pro Ser Arg Asn Phe Leu Val Val Leu Leu
        195                 200                 205

Ala Leu Thr Ala Ala Ala Ala Asp Leu Ile Gln Leu
    210                 215                 220
```

<210> SEQ ID NO 50
<211> LENGTH: 1000
<212> TYPE: DNA
<213> ORGANISM: Oryza sativa

<400> SEQUENCE: 50

```
ttctgatatg tcattgccca tgcccagtac tcacgctcct gacgaactta tgcctgttgc        60
gtctttcctc tgtcggtcgg cttttggactc aaatcaggtg gtgccgtgtg ttgtacagat       120 gcagggagg atgatctctg agaaattttg tccggaatgg tgatgttttc tcttttggtg        180
tgctccgata gtccgatcca tggtatgtca gtacaagtgt gctgcttctg ctatgtcat        240 gcaccattga caacattcat agggtacgga tagaatatgg tttatattct cccatagtct       300
tcatgtcact ggaagccaaa gaagagcatt tctgcagtca cacggtcatg cagcatccgc       360
```

```
actcaatcga tgtagtaata tagagtccag tcgcgcacaa gtcaaacagt taaacaaaac      420
ccgtttggct caccttgtca aaatgttggc catgcctgac gtcttcttct acaacctggc      480
cagctgggcc gtttggttcg gctcctcgca cctgattcac atatccagct taattccttt      540
aggattattt attctatttt ttaaaaaaaa atacatcctg tcaagaaaaa tattctagta      600
tttgcttaga ccacttgtct taaatagttt gttaaattta tttatcacaa catttaattt      660
atccctatta aaaagtagat aatctacaaa aaaacagtcc atccaatatt ttctaaacaa      720
agccttaagt tgaacgatta gcgaatggct ggtgcaacaa aatcaacgta gctgcttccc      780
catttacgtt ccaagatggc cagcctatgt gctaactgct actaccttca tcgccacaag      840
tcaactggaa gtaggcatca gggttacctt ctgcagaggc aacccagtct agtcaagccc      900
agcaacttgc acaacttgac caagaaggca agaacacaca caccctcgct tgcttaaatt      960
ctagctgaat tccattcgat tctagtctca ctctcatgta                           1000

<210> SEQ ID NO 51
<211> LENGTH: 2543
<212> TYPE: DNA
<213> ORGANISM: Zea mays

<400> SEQUENCE: 51
atgcccatcc tcaaaaccca acccaaccaa cttgagcgcg cgactcaagg cgccacaccg       60
gcaccggcat gcaccatggg tcctaccaca gctcgcctcc ttcccctcct gcccttcgtc      120
gccgtgttcc tcctcgcctc ccccgtggac gccgactccg ccctggacgc ggccacgcgg      180
tgcgcggcca cgatcgtgtc catctcgccg tgcctgccgc acgtggcggc cgtggcgcca      240
ccgctggcta gctgcccgcc tgccccaacc gacgcctgct gcgtcgcctt cctccgcgct      300
gtatccccgt tggcagcggg aggcggagag gagggctgcc tgtgccacct gctccgcaac      360
ccgcttctcc ttggctttcc catcgacgcc gcccgcctcg ccgcgctcct ccctgcctgc      420
gctgcgggaa atgccttcgc cgccgccaac gtggaggccg ccaccctctt cgctgacgcc      480
tgccgtggtg agggaatcac gccccctcgt gcctttctcc cctctcgcac catgatcgaa      540
gaatcatgtg cgttgttgcg tcaggttcct gtacgcgttc tcgtcgcaat gctgctgtgt      600
ttgcgcgctt ttgttatgca acaaccgcat atggtggact agctcaagtt gtggatacaa      660
atagcactgc ctgcttgctt gctgcctcct agacgcgcca ttatcgttca atgggtagtc      720
atcaacttaa tcagtcgtat attgttcttt caaattttta gcgactctgt tgttctgac       780 attaattgct gcaatagtag tatttctgct atttagcact ggtgcgtagc atttagaatt      840
ccttgcgtta gtaagattgt atgcgatgta tagtataggg ctaattatta ttggccaggt      900
aagttttagc ccagatctag cctatatttt ttagccccaa ctcgtaacta ggcttagctg      960
attcaagtag acccttagca agactcgctc atttgtcgtg ttgcttatca accgttattt     1020
tgccttgaag tggaaataca tgctattgaa gtgtataagt ggattatcta atttctgtcg     1080
ttctcttatt agtttaatct tttgacttaa attgattagc acgtccactc taacatggta     1140
ttgaagccag aggtctcgag ttcgaatcct gacaaaagcg acagagactt tttttatgtc     1200
tctatctatt tattttcacg tttgtgactt tctctctggc tgtacgtgag tggaggtgtt     1260
gaagtgtata agtcgattgt ctatcttttg ctaatagctt aagcttttgg gtgcaactgg     1320
ttagtgcgtc ccctctaaca catgccaaca tgtttcattt tgtaataga  agggaattgt     1380 acttttgcac acttttcttt cataatttaa cgatacacca ttagtttggc atgtgataaa     1440
caaaatgtta gtttcttagg aaccatgatt ggtcatctac ttggggcgta tctaatgcca     1500
```

```
taggcttccc acactatgca gggtctggga aagagtatct ttaagtgtaa gccttacccg    1560
cataatatgc agaggttgga gcactggcca tctactaatc ttaatcaatt ttccatgttt    1620
tgatttaaga gtcatttttg ttctcaaaca aatttattgt aacagtgtga tagttctgtc    1680
acatgtcata tcctgatggt ttagcaggaa acaaaagtta cctgttgctg gtaaatttgt    1740
ctcccttact ataagttcac atattttgt tatatgttag attagaaggt gccatctttc    1800
ttattgacat gcagatcgcg catgtactgc ttgtggtgtt tatcctaatc atatgacgaa    1860
atgagataag agtataatat tgcacaatcc attaactttc cacttatcat tttgttgttt    1920
catttcctga gcatagatct aaaggtgctg ccgggattgc atttcatgcc gcaatcaaca    1980
accgggccag aaatttcacc aggtaaacat gcatatttct tcagtgtacc actccatttt    2040
ttttaaaaaa agggttcaca ctgctcgtct gtccaagcaa acttagtttg ttgtgcaatt    2100
acagtttgtg tttcgtgaga tcggacatgt tcataatgta tcgtaactac atgacacatc    2160
atgcatgcga tgcacatttc atagttcata acggtttagt actttgtgct attgtttatg    2220
tcaactactc ttactgtgtt gtaatgaaga gtgctttgta attttgttgc catgtatgga    2280
ctattgtgta cttaatttgt ggtaatgagc acttgtactt gtctatgtca tggtttgcct    2340
tcctatgaag gttatataaa ttaatctgtt gatacatatg tcttggcgca gctgctgtcc    2400
ctgaattgat gtccaagcca aaggaggcgg ttccacttcc accagctgga tcaatggttc    2460
gttcaggcac tgaggtcacc agttcccgtg gtattcctac tgcagcattg atcctcgcgg    2520
cagcaggagc tgttatcaca tag                                            2543

<210> SEQ ID NO 52
<211> LENGTH: 2001
<212> TYPE: DNA
<213> ORGANISM: Zea mays

<400> SEQUENCE: 52
caacagaagc attgaagcac gaagtgatat gaagactagc caaaggccat ctaccgaacg      60
tccaatctgt tgcagaccaa ataaatttaa aacctaacaa gatatgggca gatcgcgtgc     120
tcgatctcaa aggcaaaact gtatgctgac ttctaaagca taagttgat gatataatgc      180 tgatctctaa ggcattcgac aaaaggaaag gacaatttct gaaaaacagc gtgagatgaa     240
gaccttcgag tggattattt tcagtaatcc actcaaagct cggggggctac acccaatgaa     300 tcatcaaccc caagagacag aatgctgatt tctaaagcat aagatgaaac taagacaagg     360
ctgacttcta aaagcacaag tggaagataa agtgatttc tgagaagact tgaaatgaag     420
accttcaagt ggattattta caaaaaacca ctcgaagctc gggggctaca cccattgggt     480
gcaccaatga aatttgaatt ctaaagagca aaatgctgac caccaaagca taaactcgag     540
atagagcacc gagttctgag gaataaagcg aaggccgacg aataatggca gaagaagaca     600
atagaagatc gttttaccg ggtcactcag agttcagaag caattgcttg acagacttat     660
tttcaaggca ttccttatca aaataaaaaa ctgcaagctg gacctaggat ctttgggccg     720
gttatttcaa tatcaaccca agatcggggg gcttgtgggg gacggatatc ccccgggtcc     780
accgaaagga taaagacct cacgaaaggc ccgtggggca aataaatcgc aaggttatcc     840
cttcgtgggc ctagagagga acgtctagtg aagtggattg acacaaggcc ggattgacgc     900
aagcccagac ggcctgatga atttaagcaa tgatcgcaac agtgattcga cctgcccgtg     960
cagtgccctc gtacatcgga actgaataag ggataggtcg gcggaattat aggaagatag    1020
```

```
gctcagttgg ttcactatta cttaggcaca cattgttatc atatccacat gtaacgcccc    1080
acggtcgagt atataaggcc taggggggcac cccctcgaaa gcatctcatt acttagccat    1140
ccatccggtt ctctaacatc ttcgacacta gagagccttc ttgtaatcca ccacataaag    1200
tactcacgct aggacgtagg gtgttacaca tctcaaagcg gcccgaacct gtacaaaatt    1260
gtccactgtc tctcgtgcat caagcgcgaa ctatcgagct acagtcggta acaccgtcct    1320
actccaaaaa tcacctcgag gagcaacccc gggtgcgcgg tcggacccaa acaccataa     1380 cacttagaat ttataagacc tattttttggt agttttatag aggagaataa taaaaatgga    1440
tagcattaaa acatgactat caaatagata gatactacct ccgttcttga atatttgtcg    1500
ctcactagtt cacttttgaa ctaaaacgtg acaaataaaa aagaatgaag ggagtacgat    1560
ccagaaacaa agaagaatct atatgaaaac aaggtatcaa cattgcagta atctgattag    1620
tcctatgtaa accgcctttt agatgatgca caaaatctgt ctctagaaaa cctatttctt    1680
tatcgaggcc atccttcatg gagattttgg aatgatgtat acatcaacac gtggtttcgc    1740
taaaatgccc atcaggccat aggacttacc aaaatgttct actaatatga atatattgct    1800
ataatactcg tacctttttca atttcataat atcatatctt atgttttgta atcttcatat    1860
tgaccaaaat acccttcttg caaaagaact tactcttcct gatgtcattt tcttgctaaa    1920
aaattaacac atattttgaa cgaagccaca taatacgttt attccaaata tctcctcgct    1980
gtctcctggc tcaattttcc c                                              2001

<210> SEQ ID NO 53
<211> LENGTH: 705
<212> TYPE: DNA
<213> ORGANISM: Zea mays

<400> SEQUENCE: 53
atgcccatcc tcaaaaccca acccaaccaa cttgagcgcg cgactcaagg cgccacaccg     60
gcaccggcat gcaccatggg tcctaccaca gctcgcctcc ttccccctcct gcccttcgtc    120 gccgtgttcc tcctcgcctc ccccgtggac gccgactccg ccctggacgc ggccacgcgg    180
tgcgcggcca cgatcgtgtc catctcgccg tgcctgccgc acgtggcggc cgtggcgcca    240
ccgctggcta gctgcccgcc tgccccaacc gacgcctgct gcgtcgcctt cctccgcgct    300
gtatccccgt tggcagcggg aggcggagag gagggctgcc tgtgccacct gctccgcaac    360
ccgcttctcc ttggctttcc catcgacgcc gcccgcctcg ccgcgctcct ccctgcctgc    420
gctgcgggaa atgccttcgc cgccgccaac gtggaggccg ccaccctctt cgctgacgcc    480
tgccgtgatc taaaggtgct gccgggattg catttcatgc cgcaatcaac aaccgggcca    540
gaaatttcac cagctgctgt ccctgaattg atgtccaagc caaaggaggc ggttccactt    600
ccaccagctg gatcaatggt tcgttcaggc actgaggtca ccagttcccg tggtattcct    660
actgcagcat tgatcctcgc ggcagcagga gctgttatca catag                     705

<210> SEQ ID NO 54
<211> LENGTH: 234
<212> TYPE: PRT
<213> ORGANISM: Zea mays

<400> SEQUENCE: 54

Met Pro Ile Leu Lys Thr Gln Pro Asn Gln Leu Glu Arg Ala Thr Gln
1               5                   10                  15

Gly Ala Thr Pro Ala Pro Ala Cys Thr Met Gly Pro Thr Thr Ala Arg
            20                  25                  30
```

```
Leu Leu Pro Leu Leu Pro Phe Val Ala Val Phe Leu Leu Ala Ser Pro
        35                  40                  45

Val Asp Ala Asp Ser Ala Leu Asp Ala Ala Thr Arg Cys Ala Ala Thr
 50                  55                  60

Ile Val Ser Ile Ser Pro Cys Leu Pro His Val Ala Ala Val Ala Pro
 65                  70                  75                  80

Pro Leu Ala Ser Cys Pro Pro Ala Pro Thr Asp Ala Cys Cys Val Ala
                 85                  90                  95

Phe Leu Arg Ala Val Ser Pro Leu Ala Ala Gly Gly Gly Glu Glu Gly
                100                 105                 110

Cys Leu Cys His Leu Leu Arg Asn Pro Leu Leu Leu Gly Phe Pro Ile
            115                 120                 125

Asp Ala Ala Arg Leu Ala Ala Leu Leu Pro Ala Cys Ala Ala Gly Asn
        130                 135                 140

Ala Phe Ala Ala Ala Asn Val Glu Ala Ala Thr Leu Phe Ala Asp Ala
145                 150                 155                 160

Cys Arg Asp Leu Lys Val Leu Pro Gly Leu His Phe Met Pro Gln Ser
                165                 170                 175

Thr Thr Gly Pro Glu Ile Ser Pro Ala Ala Val Pro Glu Leu Met Ser
            180                 185                 190

Lys Pro Lys Glu Ala Val Pro Leu Pro Pro Ala Gly Ser Met Val Arg
        195                 200                 205

Ser Gly Thr Glu Val Thr Ser Ser Arg Gly Ile Pro Thr Ala Ala Leu
    210                 215                 220

Ile Leu Ala Ala Ala Gly Ala Val Ile Thr
225                 230
```

<210> SEQ ID NO 55
<211> LENGTH: 1000
<212> TYPE: DNA
<213> ORGANISM: Zea mays

<400> SEQUENCE: 55

| | | | | | |
|---|---|---|---|---|---|
| ttcttgtgat | gtttaagtgc | cacttgatac | tctcgtcggc | ctcgctcgat | cttgatctgc | 60 |
| gtttgtcgtg | cctagctttg | agcctttgac | gattcagatg | atctgcattt | gccatgccta | 120 |
| gcactttgcg | gtctccagtg | ttgtacgtgg | cagagttgtg | tcacttgaca | cttcaatgga | 180 |
| atctagtgat | cagctgatac | cttcagttgt | ttctcattca | gaagcaggtc | aaagatctac | 240 |
| tcagtcttga | tgagatcgaa | gttgaaaccc | gccgatatat | caggagttgt | ggttcagggc | 300 |
| caagagacag | attgtgtgcc | ccggccccg | ggacaagtcg | acaactgcga | acttggtttc | 360 |
| atcagacgag | tcgtcacttt | cctatcagac | atgcatatat | aagatatcga | ttttttatac | 420 |
| ctttccctga | taagcctcat | gatgttgttg | ttcgaaatcc | gatgcccgtg | ccagcaattc | 480 |
| gtcgatggac | tcaaagtttg | tcatggtaac | tctgtcaggg | tcttagaccg | aggggatatc | 540 |
| atgcggtact | ctgggcagca | gatgatgaac | tccaccttca | tgccttcagg | tgcgctgatc | 600 |
| tgcattggct | ccactccact | ggtcgagtat | agagcaactt | ctctccttaa | tgtgacctga | 660 |
| acgtgggccc | tggtacatgg | tagttgtcgg | ccaaaataga | tctggccact | catgcaatga | 720 |
| ttccctccac | taccggaatc | gccggctttg | ccgagtgtcg | cactcggcaa | agagggctcg | 780 |
| gcatacagtt | catcggcaaa | gccgtctttg | ccgagtactt | tttctcgggc | actcggcaaa | 840 |
| gtggtttgcc | gagtgccaga | gagcactcgg | caaagaaaag | cagccgttac | ggcgacgggt | 900 |
| gacggagacg | gagtctttgc | cgagtgtccc | aggcgacact | cggcaaagga | gttacctttg | 960 |

```
ccgagtgtcg gcctgacagc actcggcaaa gaatccgcta                    1000
```

<210> SEQ ID NO 56
<211> LENGTH: 22
<212> TYPE: DNA
<213> ORGANISM: Triticum aestivum

<400> SEQUENCE: 56

```
cgccaccagc agcagcccgc gg                                         22
```

<210> SEQ ID NO 57
<211> LENGTH: 23
<212> TYPE: DNA
<213> ORGANISM: Triticum aestivum

<400> SEQUENCE: 57

```
gggcggggggg ctgctgacga cgg                                       23
```

<210> SEQ ID NO 58
<211> LENGTH: 23
<212> TYPE: DNA
<213> ORGANISM: Triticum aestivum

<400> SEQUENCE: 58

```
gtcgtccccg ccgccgtccc agg                                        23
```

<210> SEQ ID NO 59
<211> LENGTH: 23
<212> TYPE: DNA
<213> ORGANISM: Triticum aestivum

<400> SEQUENCE: 59

```
gacgaagaag aaggccgcct tgg                                        23
```

<210> SEQ ID NO 60
<211> LENGTH: 23
<212> TYPE: DNA
<213> ORGANISM: Triticum aestivum

<400> SEQUENCE: 60

```
gcccacggcg ccgtccaagg cgg                                        23
```

<210> SEQ ID NO 61
<211> LENGTH: 23
<212> TYPE: DNA
<213> ORGANISM: Triticum aestivum

<400> SEQUENCE: 61

```
ggccgtggcg acgaagaaga agg                                        23
```

<210> SEQ ID NO 62
<211> LENGTH: 23
<212> TYPE: DNA
<213> ORGANISM: Triticum aestivum

<400> SEQUENCE: 62

```
gtagaggccg agcatggccg tgg                                        23
```

<210> SEQ ID NO 63
<211> LENGTH: 23
<212> TYPE: DNA
<213> ORGANISM: Triticum aestivum

```
<400> SEQUENCE: 63
ggccttcttc ttcgtcgcca cgg                                              23

<210> SEQ ID NO 64
<211> LENGTH: 23
<212> TYPE: DNA
<213> ORGANISM: Triticum aestivum

<400> SEQUENCE: 64
gatgatgtag aggccgagca tgg                                              23

<210> SEQ ID NO 65
<211> LENGTH: 23
<212> TYPE: DNA
<213> ORGANISM: Triticum aestivum

<400> SEQUENCE: 65
gagatcccgc gggctgctgc tgg                                              23

<210> SEQ ID NO 66
<211> LENGTH: 23
<212> TYPE: DNA
<213> ORGANISM: Triticum aestivum

<400> SEQUENCE: 66
gctgctggcg gcgctgctgc cgg                                              23

<210> SEQ ID NO 67
<211> LENGTH: 23
<212> TYPE: DNA
<213> ORGANISM: Triticum aestivum

<400> SEQUENCE: 67
gcacggcgag aaggacacga tgg                                              23

<210> SEQ ID NO 68
<211> LENGTH: 23
<212> TYPE: DNA
<213> ORGANISM: Triticum aestivum

<400> SEQUENCE: 68
gcagcaggcg ctggtgggcg cgg                                              23

<210> SEQ ID NO 69
<211> LENGTH: 23
<212> TYPE: DNA
<213> ORGANISM: Triticum aestivum

<400> SEQUENCE: 69
gccgcgcagc aggcgctggt ggg                                              23

<210> SEQ ID NO 70
<211> LENGTH: 23
<212> TYPE: DNA
<213> ORGANISM: Triticum aestivum

<400> SEQUENCE: 70
gaacgccgcg cagcaggcgc tgg                                              23

<210> SEQ ID NO 71
<211> LENGTH: 23
<212> TYPE: DNA
<213> ORGANISM: Triticum aestivum
```

```
<400> SEQUENCE: 71
gcgcaggaac gccgcgcagc agg                                              23

<210> SEQ ID NO 72
<211> LENGTH: 23
<212> TYPE: DNA
<213> ORGANISM: Triticum aestivum

<400> SEQUENCE: 72
gcccaccagc gcctgctgcg cgg                                              23

<210> SEQ ID NO 73
<211> LENGTH: 23
<212> TYPE: DNA
<213> ORGANISM: Triticum aestivum

<400> SEQUENCE: 73
gccgccttcg ccgtccccgg agg                                              23

<210> SEQ ID NO 74
<211> LENGTH: 23
<212> TYPE: DNA
<213> ORGANISM: Triticum aestivum

<400> SEQUENCE: 74
ggggacggcg aaggcggcgg agg                                              23

<210> SEQ ID NO 75
<211> LENGTH: 23
<212> TYPE: DNA
<213> ORGANISM: Triticum aestivum

<400> SEQUENCE: 75
gggacggcga aggcggcgga ggg                                              23

<210> SEQ ID NO 76
<211> LENGTH: 23
<212> TYPE: DNA
<213> ORGANISM: Triticum aestivum

<400> SEQUENCE: 76
ggacggcgaa ggcggcggag ggg                                              23

<210> SEQ ID NO 77
<211> LENGTH: 23
<212> TYPE: DNA
<213> ORGANISM: Triticum aestivum

<400> SEQUENCE: 77
ggcgaaggcg gcggagggga ggg                                              23

<210> SEQ ID NO 78
<211> LENGTH: 23
<212> TYPE: DNA
<213> ORGANISM: Triticum aestivum

<400> SEQUENCE: 78
gccgaggcgc gcggcgtcga cgg                                              23

<210> SEQ ID NO 79
<211> LENGTH: 23
<212> TYPE: DNA
```

```
<213> ORGANISM: Triticum aestivum

<400> SEQUENCE: 79
gttttcgcgg aggcgcaggt ggg                                                23

<210> SEQ ID NO 80
<211> LENGTH: 23
<212> TYPE: DNA
<213> ORGANISM: Triticum aestivum

<400> SEQUENCE: 80
ggttttcgcg gaggcgcagg tgg                                                23

<210> SEQ ID NO 81
<211> LENGTH: 23
<212> TYPE: DNA
<213> ORGANISM: Triticum aestivum

<400> SEQUENCE: 81
ggaggttttc gcggaggcgc agg                                                23

<210> SEQ ID NO 82
<211> LENGTH: 19
<212> TYPE: DNA
<213> ORGANISM: artificial
<220> FEATURE:
<223> OTHER INFORMATION: DNA version of guideRNA to target DNA target

<400> SEQUENCE: 82
cgccaccagc agcagcccg                                                     19

<210> SEQ ID NO 83
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 83
gggcgggggg ctgctgacga                                                    20

<210> SEQ ID NO 84
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 84
gtcgtccccg ccgccgtccc                                                    20

<210> SEQ ID NO 85
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 85
gacgaagaag aaggccgcct                                                    20

<210> SEQ ID NO 86
<211> LENGTH: 20
<212> TYPE: DNA
<213> ORGANISM: artificial
```

```
<220> FEATURE:
<223> OTHER INFORMATION: DNA version of guideRNA to target DNA target

<400> SEQUENCE: 86
gcccacggcg ccgtccaagg                                                   20

<210> SEQ ID NO 87
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 87
ggccgtggcg acgaagaaga                                                   20

<210> SEQ ID NO 88
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 88
gtagaggccg agcatggccg                                                   20

<210> SEQ ID NO 89
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 89
ggccttcttc ttcgtcgcca                                                   20

<210> SEQ ID NO 90
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 90
gatgatgtag aggccgagca                                                   20

<210> SEQ ID NO 91
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 91
gagatcccgc gggctgctgc                                                   20

<210> SEQ ID NO 92
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 92
gctgctggcg gcgctgctgc                                                   20
```

<210> SEQ ID NO 93
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 93
gcacggcgag aaggacacga                                          20

<210> SEQ ID NO 94
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 94
gcagcaggcg ctggtgggcg                                          20

<210> SEQ ID NO 95
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 95
gccgcgcagc aggcgctggt                                          20

<210> SEQ ID NO 96
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 96
gaacgccgcg cagcaggcgc                                          20

<210> SEQ ID NO 97
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 97
gcgcaggaac gccgcgcagc                                          20

<210> SEQ ID NO 98
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 98
gcccaccagc gcctgctgcg                                          20

<210> SEQ ID NO 99
<211> LENGTH: 20
<212> TYPE: DNA
<213> ORGANISM: artificial
<220> FEATURE:
<223> OTHER INFORMATION: DNA version of guideRNA to target DNA target

```
<400> SEQUENCE: 99
gccgccttcg ccgtccccgg                                               20

<210> SEQ ID NO 100
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 100
ggggacggcg aaggcggcgg                                               20

<210> SEQ ID NO 101
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 101
gggacggcga aggcggcgga                                               20

<210> SEQ ID NO 102
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 102
ggacggcgaa ggcggcggag                                               20

<210> SEQ ID NO 103
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 103
ggcgaaggcg gcggagggga                                               20

<210> SEQ ID NO 104
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 104
gccgaggcgc gcggcgtcga                                               20

<210> SEQ ID NO 105
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 105
gttttcgcgg aggcgcaggt                                               20

<210> SEQ ID NO 106
```

```
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 106
ggttttcgcg gaggcgcagg                                              20

<210> SEQ ID NO 107
<211> LENGTH: 20
<212> TYPE: DNA
<213> ORGANISM: artificial
<220> FEATURE:
<223> OTHER INFORMATION: DNA version of guideRNA to target DNA target

<400> SEQUENCE: 107
ggaggttttc gcggaggcgc                                              20

<210> SEQ ID NO 108
<211> LENGTH: 20
<212> TYPE: DNA
<213> ORGANISM: Triticum aestivum

<400> SEQUENCE: 108
cgccaccagc agcagcaccg                                              20

<210> SEQ ID NO 109
<211> LENGTH: 20
<212> TYPE: DNA
<213> ORGANISM: Triticum aestivum

<400> SEQUENCE: 109
cgccaccagc agcagctccg                                              20

<210> SEQ ID NO 110
<211> LENGTH: 20
<212> TYPE: DNA
<213> ORGANISM: Triticum aestivum

<400> SEQUENCE: 110
cgccaccagc agcagccccg                                              20

<210> SEQ ID NO 111
<211> LENGTH: 16
<212> TYPE: DNA
<213> ORGANISM: Triticum aestivum

<400> SEQUENCE: 111
cgccaccagc agcccg                                                  16

<210> SEQ ID NO 112
<211> LENGTH: 56
<212> TYPE: DNA
<213> ORGANISM: artificial
<220> FEATURE:
<223> OTHER INFORMATION: amplicon

<400> SEQUENCE: 112
ctcggatcct ccgtgagatc aaattactcy gcctattgag acatcctgat atagtt      56

<210> SEQ ID NO 113
<211> LENGTH: 65
<212> TYPE: DNA
<213> ORGANISM: artificial
```

```
<220> FEATURE:
<223> OTHER INFORMATION: amplicon

<400> SEQUENCE: 113
cagtcatgga aaaggagcct gagaagggac gcggcgatgc gcrgttcctt ggcaatcgcc    60
ttctt                                                                65

<210> SEQ ID NO 114
<211> LENGTH: 65
<212> TYPE: DNA
<213> ORGANISM: artificial
<220> FEATURE:
<223> OTHER INFORMATION: amplicon

<400> SEQUENCE: 114
catccatctt tgacttgttc ttttatttac ycttcttcat ttaacttgct caccgcgaag    60
acttg                                                                65

<210> SEQ ID NO 115
<211> LENGTH: 54
<212> TYPE: DNA
<213> ORGANISM: artificial
<220> FEATURE:
<223> OTHER INFORMATION: amplicon

<400> SEQUENCE: 115
gctgtagtga tttcactcct atcgcyaagc aaattgagtc agacaagtcg acta          54

<210> SEQ ID NO 116
<211> LENGTH: 65
<212> TYPE: DNA
<213> ORGANISM: artificial
<220> FEATURE:
<223> OTHER INFORMATION: amplicon

<400> SEQUENCE: 116
ctgcagccga cctccagcta tttccacgac atcgtgccgg ggaartgtgc ccagccattg    60
ggatg                                                                65

<210> SEQ ID NO 117
<211> LENGTH: 52
<212> TYPE: DNA
<213> ORGANISM: artificial
<220> FEATURE:
<223> OTHER INFORMATION: amplicon

<400> SEQUENCE: 117
ctgatccact caccagtatg aaatkataaa cacagcacag gtaacaagag cc             52

<210> SEQ ID NO 118
<211> LENGTH: 60
<212> TYPE: DNA
<213> ORGANISM: artificial
<220> FEATURE:
<223> OTHER INFORMATION: amplicon

<400> SEQUENCE: 118
agtttgaatt gcttaccaca tgtcacrtgg ttgatctcat ctcttacatc cttttttgtag    60

<210> SEQ ID NO 119
<211> LENGTH: 51
<212> TYPE: DNA
<213> ORGANISM: artificial
<220> FEATURE:
```

<223> OTHER INFORMATION: amplicon

<400> SEQUENCE: 119
cttcttgtat agaggtgatc gcgttyatac agtcacacgc cacacatact c    51

<210> SEQ ID NO 120
<211> LENGTH: 61
<212> TYPE: DNA
<213> ORGANISM: artificial
<220> FEATURE:
<223> OTHER INFORMATION: amplicon

<400> SEQUENCE: 120
ctcccggctt ctggcactcr aggtggcatt cttctggcct aggatccoct tgtggtccag    60 c    61

<210> SEQ ID NO 121
<211> LENGTH: 51
<212> TYPE: DNA
<213> ORGANISM: artificial
<220> FEATURE:
<223> OTHER INFORMATION: amplicon

<400> SEQUENCE: 121
caagccacat agccaagggt gattamaatt tcacacgtgt tgctcaacca t    51

<210> SEQ ID NO 122
<211> LENGTH: 54
<212> TYPE: DNA
<213> ORGANISM: artificial
<220> FEATURE:
<223> OTHER INFORMATION: amplicon

<400> SEQUENCE: 122
caggactccc tcatagggc ttcrcgaaaa tttaaaattg tagacttcta tggc    54

<210> SEQ ID NO 123
<211> LENGTH: 54
<212> TYPE: DNA
<213> ORGANISM: artificial
<220> FEATURE:
<223> OTHER INFORMATION: amplicon

<400> SEQUENCE: 123
catgctcctc tggatgcgga agagcatrgg ctaccctctg gtggtcttca tgcg    54

<210> SEQ ID NO 124
<211> LENGTH: 54
<212> TYPE: DNA
<213> ORGANISM: artificial
<220> FEATURE:
<223> OTHER INFORMATION: amplicon

<400> SEQUENCE: 124
agcaccaagg caaacaccaa ccaatcragg aaactactga ttgcggatta aaag    54

<210> SEQ ID NO 125
<211> LENGTH: 61
<212> TYPE: DNA
<213> ORGANISM: artificial
<220> FEATURE:
<223> OTHER INFORMATION: amplicon

<400> SEQUENCE: 125
gtggaaataa ggcaagtgat tcatcacata tgttgtygat ccatggacag agtagtttgt    60

-continued

```
g                                                             61

<210> SEQ ID NO 126
<211> LENGTH: 57
<212> TYPE: DNA
<213> ORGANISM: artificial
<220> FEATURE:
<223> OTHER INFORMATION: amplicon

<400> SEQUENCE: 126
cctcatgagt ataaatgaca cctcaayttg ctaatttgac aagaacaatg cctataa    57

<210> SEQ ID NO 127
<211> LENGTH: 86
<212> TYPE: DNA
<213> ORGANISM: artificial
<220> FEATURE:
<223> OTHER INFORMATION: amplicon

<400> SEQUENCE: 127
tatgacctca aatttgttcc agtagatatt rtatccacag acagaaaggg gaagtaaatt    60
tgaaatgtaa ttgcggtgcc aaactg                                        86

<210> SEQ ID NO 128
<211> LENGTH: 54
<212> TYPE: DNA
<213> ORGANISM: artificial
<220> FEATURE:
<223> OTHER INFORMATION: amplicon

<400> SEQUENCE: 128
ggaattaggt caaatggagc tgtgtrggac ccatgagctt aggagggcgt gtcg    54

<210> SEQ ID NO 129
<211> LENGTH: 58
<212> TYPE: DNA
<213> ORGANISM: artificial
<220> FEATURE:
<223> OTHER INFORMATION: amplicon

<400> SEQUENCE: 129
atgacgattc tcatttgtgc agataaatrt taaggttaag gttgtttctg gatctcct    58

<210> SEQ ID NO 130
<211> LENGTH: 66
<212> TYPE: DNA
<213> ORGANISM: artificial
<220> FEATURE:
<223> OTHER INFORMATION: amplicon

<400> SEQUENCE: 130
gctgcgagta gcaagttaag atcatatgra caagtaaaaa taaggcagaa agatggggat    60
aacatg                                                              66

<210> SEQ ID NO 131
<211> LENGTH: 69
<212> TYPE: DNA
<213> ORGANISM: artificial
<220> FEATURE:
<223> OTHER INFORMATION: amplicon

<400> SEQUENCE: 131
ccccgttcca tttttataatg cgtatgattt tttctctcak attccgaaat gtagtgcgta    60
```

-continued

| | |
|---|---|
| tatgcagca | 69 |

<210> SEQ ID NO 132
<211> LENGTH: 19
<212> TYPE: DNA
<213> ORGANISM: artificial
<220> FEATURE:
<223> OTHER INFORMATION: primer

<400> SEQUENCE: 132

| | |
|---|---|
| acgacgcctg tgtcggatg | 19 |

<210> SEQ ID NO 133
<211> LENGTH: 22
<212> TYPE: DNA
<213> ORGANISM: artificial
<220> FEATURE:
<223> OTHER INFORMATION: primer

<400> SEQUENCE: 133

| | |
|---|---|
| caccgtatgc aacaagaggt cc | 22 |

<210> SEQ ID NO 134
<211> LENGTH: 19
<212> TYPE: DNA
<213> ORGANISM: artificial
<220> FEATURE:
<223> OTHER INFORMATION: primer

<400> SEQUENCE: 134

| | |
|---|---|
| cagaaccagc gtccccgaa | 19 |

<210> SEQ ID NO 135
<211> LENGTH: 23
<212> TYPE: DNA
<213> ORGANISM: artificial
<220> FEATURE:
<223> OTHER INFORMATION: primer

<400> SEQUENCE: 135

| | |
|---|---|
| ttcaccgtat gcaacaagag gat | 23 |

<210> SEQ ID NO 136
<211> LENGTH: 22
<212> TYPE: DNA
<213> ORGANISM: artificial
<220> FEATURE:
<223> OTHER INFORMATION: primer

<400> SEQUENCE: 136

| | |
|---|---|
| gtcggatgat cggtcgggat ct | 22 |

<210> SEQ ID NO 137
<211> LENGTH: 21
<212> TYPE: DNA
<213> ORGANISM: artificial
<220> FEATURE:
<223> OTHER INFORMATION: primer

<400> SEQUENCE: 137

| | |
|---|---|
| catcgtccag atgcagagag g | 21 |

<210> SEQ ID NO 138
<211> LENGTH: 48
<212> TYPE: DNA
<213> ORGANISM: artificial

```
<220> FEATURE:
<223> OTHER INFORMATION: primer

<400> SEQUENCE: 138
gaaggtgacc aagttcatgc taactatatc aggatgtctc aataggca          48

<210> SEQ ID NO 139
<211> LENGTH: 46
<212> TYPE: DNA
<213> ORGANISM: artificial
<220> FEATURE:
<223> OTHER INFORMATION: primer

<400> SEQUENCE: 139
gaaggtcgga gtcaacggat tctatatcag gatgtctcaa taggcg            46

<210> SEQ ID NO 140
<211> LENGTH: 25
<212> TYPE: DNA
<213> ORGANISM: artificial
<220> FEATURE:
<223> OTHER INFORMATION: primer

<400> SEQUENCE: 140
ctcggatcct ccgtgagatc aaatt                                   25

<210> SEQ ID NO 141
<211> LENGTH: 44
<212> TYPE: DNA
<213> ORGANISM: artificial
<220> FEATURE:
<223> OTHER INFORMATION: primer

<400> SEQUENCE: 141
gaaggtgacc aagttcatgc taagaaggcg attgccaagg aact              44

<210> SEQ ID NO 142
<211> LENGTH: 43
<212> TYPE: DNA
<213> ORGANISM: artificial
<220> FEATURE:
<223> OTHER INFORMATION: primer

<400> SEQUENCE: 142
gaaggtcgga gtcaacggat tagaaggcga ttgccaagga acc               43

<210> SEQ ID NO 143
<211> LENGTH: 25
<212> TYPE: DNA
<213> ORGANISM: artificial
<220> FEATURE:
<223> OTHER INFORMATION: primer

<400> SEQUENCE: 143
cagtcatgga aaggagcct gagaa                                    25

<210> SEQ ID NO 144
<211> LENGTH: 52
<212> TYPE: DNA
<213> ORGANISM: artificial
<220> FEATURE:
<223> OTHER INFORMATION: primer

<400> SEQUENCE: 144
gaaggtgacc aagttcatgc tcatccatct ttgacttgtt cttttattta ct     52
```

```
<210> SEQ ID NO 145
<211> LENGTH: 51
<212> TYPE: DNA
<213> ORGANISM: artificial
<220> FEATURE:
<223> OTHER INFORMATION: primer

<400> SEQUENCE: 145
gaaggtcgga gtcaacggat tatccatctt tgacttgttc ttttatttac c        51

<210> SEQ ID NO 146
<211> LENGTH: 25
<212> TYPE: DNA
<213> ORGANISM: artificial
<220> FEATURE:
<223> OTHER INFORMATION: primer

<400> SEQUENCE: 146
caagtcttcg cggtgagcaa gttaa                                       25

<210> SEQ ID NO 147
<211> LENGTH: 44
<212> TYPE: DNA
<213> ORGANISM: artificial
<220> FEATURE:
<223> OTHER INFORMATION: primer

<400> SEQUENCE: 147
gaaggtgacc aagttcatgc tgtagtgatt tcactcctat cgct                  44

<210> SEQ ID NO 148
<211> LENGTH: 44
<212> TYPE: DNA
<213> ORGANISM: artificial
<220> FEATURE:
<223> OTHER INFORMATION: primer

<400> SEQUENCE: 148
gaaggtcgga gtcaacggat tgtagtgatt tcactcctat cgcc                  44

<210> SEQ ID NO 149
<211> LENGTH: 28
<212> TYPE: DNA
<213> ORGANISM: artificial
<220> FEATURE:
<223> OTHER INFORMATION: primer

<400> SEQUENCE: 149
tagtcgactt gtctgactca atttgctt                                    28

<210> SEQ ID NO 150
<211> LENGTH: 42
<212> TYPE: DNA
<213> ORGANISM: artificial
<220> FEATURE:
<223> OTHER INFORMATION: primer

<400> SEQUENCE: 150
gaaggtgacc aagttcatgc tcatcccaat ggctgggcac at                    42

<210> SEQ ID NO 151
<211> LENGTH: 42
<212> TYPE: DNA
<213> ORGANISM: artificial
<220> FEATURE:
<223> OTHER INFORMATION: primer
```

```
<400> SEQUENCE: 151
gaaggtcgga gtcaacggat tcatcccaat ggctgggcac ac                         42

<210> SEQ ID NO 152
<211> LENGTH: 22
<212> TYPE: DNA
<213> ORGANISM: artificial
<220> FEATURE:
<223> OTHER INFORMATION: primer

<400> SEQUENCE: 152
ctgcagccga cctccagcta tt                                              22

<210> SEQ ID NO 153
<211> LENGTH: 44
<212> TYPE: DNA
<213> ORGANISM: artificial
<220> FEATURE:
<223> OTHER INFORMATION: primer

<400> SEQUENCE: 153
gaaggtgacc aagttcatgc tgatccactc accagtatga aatg                       44

<210> SEQ ID NO 154
<211> LENGTH: 48
<212> TYPE: DNA
<213> ORGANISM: artificial
<220> FEATURE:
<223> OTHER INFORMATION: primer

<400> SEQUENCE: 154
gaaggtcgga gtcaacggat taactgatcc actcaccagt atgaaatt                   48

<210> SEQ ID NO 155
<211> LENGTH: 25
<212> TYPE: DNA
<213> ORGANISM: artificial
<220> FEATURE:
<223> OTHER INFORMATION: primer

<400> SEQUENCE: 155
ggctcttgtt acctgtgctg tgttt                                           25

<210> SEQ ID NO 156
<211> LENGTH: 48
<212> TYPE: DNA
<213> ORGANISM: artificial
<220> FEATURE:
<223> OTHER INFORMATION: primer

<400> SEQUENCE: 156
gaaggtgacc aagttcatgc tagtttgaat tgcttaccac atgtcaca                   48

<210> SEQ ID NO 157
<211> LENGTH: 47
<212> TYPE: DNA
<213> ORGANISM: artificial
<220> FEATURE:
<223> OTHER INFORMATION: primer

<400> SEQUENCE: 157
gaaggtcgga gtcaacggat tgtttgaatt gcttaccaca tgtcacg                    47

<210> SEQ ID NO 158
```

```
<211> LENGTH: 30
<212> TYPE: DNA
<213> ORGANISM: artificial
<220> FEATURE:
<223> OTHER INFORMATION: primer

<400> SEQUENCE: 158
ctacaaaaag gatgtaagag atgagatcaa                                        30

<210> SEQ ID NO 159
<211> LENGTH: 45
<212> TYPE: DNA
<213> ORGANISM: artificial
<220> FEATURE:
<223> OTHER INFORMATION: primer

<400> SEQUENCE: 159
gaaggtgacc aagttcatgc ttcttgtata gaggtgatcg cgttt                       45

<210> SEQ ID NO 160
<211> LENGTH: 44
<212> TYPE: DNA
<213> ORGANISM: artificial
<220> FEATURE:
<223> OTHER INFORMATION: primer

<400> SEQUENCE: 160
gaaggtcgga gtcaacggat tcttgtatag aggtgatcgc gttc                        44

<210> SEQ ID NO 161
<211> LENGTH: 25
<212> TYPE: DNA
<213> ORGANISM: artificial
<220> FEATURE:
<223> OTHER INFORMATION: primer

<400> SEQUENCE: 161
gagtatgtgt ggcgtgtgac tgtat                                             25

<210> SEQ ID NO 162
<211> LENGTH: 39
<212> TYPE: DNA
<213> ORGANISM: artificial
<220> FEATURE:
<223> OTHER INFORMATION: primer

<400> SEQUENCE: 162
gaaggtgacc aagttcatgc tcccggcttc tggcactca                              39

<210> SEQ ID NO 163
<211> LENGTH: 39
<212> TYPE: DNA
<213> ORGANISM: artificial
<220> FEATURE:
<223> OTHER INFORMATION: primer

<400> SEQUENCE: 163
gaaggtcgga gtcaacggat tcccggcttc tggcactcg                              39

<210> SEQ ID NO 164
<211> LENGTH: 22
<212> TYPE: DNA
<213> ORGANISM: artificial
<220> FEATURE:
<223> OTHER INFORMATION: primer

<400> SEQUENCE: 164
```

-continued gctggaccac aagggatcc ta                                                22

<210> SEQ ID NO 165
<211> LENGTH: 45
<212> TYPE: DNA
<213> ORGANISM: artificial
<220> FEATURE:
<223> OTHER INFORMATION: primer

<400> SEQUENCE: 165
gaaggtgacc aagttcatgc tggttgagca acacgtgtga aattg                      45

<210> SEQ ID NO 166
<211> LENGTH: 47
<212> TYPE: DNA
<213> ORGANISM: artificial
<220> FEATURE:
<223> OTHER INFORMATION: primer

<400> SEQUENCE: 166
gaaggtcgga gtcaacggat tatggttgag caacacgtgt gaaattt                    47

<210> SEQ ID NO 167
<211> LENGTH: 25
<212> TYPE: DNA
<213> ORGANISM: artificial
<220> FEATURE:
<223> OTHER INFORMATION: primer

<400> SEQUENCE: 167
caagccacat agccaagggt gatta                                            25

<210> SEQ ID NO 168
<211> LENGTH: 52
<212> TYPE: DNA
<213> ORGANISM: artificial
<220> FEATURE:
<223> OTHER INFORMATION: primer

<400> SEQUENCE: 168
gaaggtgacc aagttcatgc tgccatagaa gtctacaatt ttaaattttc gt              52

<210> SEQ ID NO 169
<211> LENGTH: 51
<212> TYPE: DNA
<213> ORGANISM: artificial
<220> FEATURE:
<223> OTHER INFORMATION: primer

<400> SEQUENCE: 169
gaaggtcgga gtcaacggat tccatagaag tctacaattt taaattttcg c               51

<210> SEQ ID NO 170
<211> LENGTH: 22
<212> TYPE: DNA
<213> ORGANISM: artificial
<220> FEATURE:
<223> OTHER INFORMATION: primer

<400> SEQUENCE: 170
caggactccc tcatagggc tt                                                22

<210> SEQ ID NO 171
<211> LENGTH: 43
<212> TYPE: DNA

```
<213> ORGANISM: artificial
<220> FEATURE:
<223> OTHER INFORMATION: primer

<400> SEQUENCE: 171
gaaggtgacc aagttcatgc tcctctggat gcggaagagc ata            43

<210> SEQ ID NO 172
<211> LENGTH: 42
<212> TYPE: DNA
<213> ORGANISM: artificial
<220> FEATURE:
<223> OTHER INFORMATION: primer

<400> SEQUENCE: 172
gaaggtcgga gtcaacggat tctctggatg cggaagagca tg             42

<210> SEQ ID NO 173
<211> LENGTH: 23
<212> TYPE: DNA
<213> ORGANISM: artificial
<220> FEATURE:
<223> OTHER INFORMATION: primer

<400> SEQUENCE: 173
cgcatgaaga ccaccagagg gta                                  23

<210> SEQ ID NO 174
<211> LENGTH: 47
<212> TYPE: DNA
<213> ORGANISM: artificial
<220> FEATURE:
<223> OTHER INFORMATION: primer

<400> SEQUENCE: 174
gaaggtgacc aagttcatgc ttttaatccg caatcagtag tttcctt        47

<210> SEQ ID NO 175
<211> LENGTH: 46
<212> TYPE: DNA
<213> ORGANISM: artificial
<220> FEATURE:
<223> OTHER INFORMATION: primer

<400> SEQUENCE: 175
gaaggtcgga gtcaacggat tttaatccgc aatcagtagt ttcctc         46

<210> SEQ ID NO 176
<211> LENGTH: 25
<212> TYPE: DNA
<213> ORGANISM: artificial
<220> FEATURE:
<223> OTHER INFORMATION: primer

<400> SEQUENCE: 176
agcaccaagg caaacaccaa ccaat                                25

<210> SEQ ID NO 177
<211> LENGTH: 45
<212> TYPE: DNA
<213> ORGANISM: artificial
<220> FEATURE:
<223> OTHER INFORMATION: primer

<400> SEQUENCE: 177
aaggtgacca agttcatgct cacaaactac tctgtccatg gatca          45
```

<210> SEQ ID NO 178
<211> LENGTH: 45
<212> TYPE: DNA
<213> ORGANISM: artificial
<220> FEATURE:
<223> OTHER INFORMATION: primer

<400> SEQUENCE: 178
gaaggtcgga gtcaacggat tacaaactac tctgtccatg gatcg    45

<210> SEQ ID NO 179
<211> LENGTH: 29
<212> TYPE: DNA
<213> ORGANISM: artificial
<220> FEATURE:
<223> OTHER INFORMATION: primer

<400> SEQUENCE: 179
gtggaaataa ggcaagtgat tcatcacat    29

<210> SEQ ID NO 180
<211> LENGTH: 48
<212> TYPE: DNA
<213> ORGANISM: artificial
<220> FEATURE:
<223> OTHER INFORMATION: primer

<400> SEQUENCE: 180
gaaggtgacc aagttcatgc tcctcatgag tataaatgac acctcaat    48

<210> SEQ ID NO 181
<211> LENGTH: 47
<212> TYPE: DNA
<213> ORGANISM: artificial
<220> FEATURE:
<223> OTHER INFORMATION: primer

<400> SEQUENCE: 181
gaaggtcgga gtcaacggat tctcatgagt ataaatgaca cctcaac    47

<210> SEQ ID NO 182
<211> LENGTH: 30
<212> TYPE: DNA
<213> ORGANISM: artificial
<220> FEATURE:
<223> OTHER INFORMATION: primer

<400> SEQUENCE: 182
ttataggcat tgttcttgtc aaattagcaa    30

<210> SEQ ID NO 183
<211> LENGTH: 51
<212> TYPE: DNA
<213> ORGANISM: artificial
<220> FEATURE:
<223> OTHER INFORMATION: primer

<400> SEQUENCE: 183
gaaggtgacc aagttcatgc tatgacctca aatttgttcc agtagatatt a    51

<210> SEQ ID NO 184
<211> LENGTH: 49
<212> TYPE: DNA
<213> ORGANISM: artificial
<220> FEATURE:

<223> OTHER INFORMATION: primer

<400> SEQUENCE: 184
gaaggtcgga gtcaacggat tgacctcaaa tttgttccag tagatattg         49

<210> SEQ ID NO 185
<211> LENGTH: 29
<212> TYPE: DNA
<213> ORGANISM: artificial
<220> FEATURE:
<223> OTHER INFORMATION: primer

<400> SEQUENCE: 185
cagtttggca ccgcaattac atttcaaat         29

<210> SEQ ID NO 186
<211> LENGTH: 47
<212> TYPE: DNA
<213> ORGANISM: artificial
<220> FEATURE:
<223> OTHER INFORMATION: primer

<400> SEQUENCE: 186
gaaggtgacc aagttcatgc tggaattagg tcaaatggag ctgtgta         47

<210> SEQ ID NO 187
<211> LENGTH: 46
<212> TYPE: DNA
<213> ORGANISM: artificial
<220> FEATURE:
<223> OTHER INFORMATION: primer

<400> SEQUENCE: 187
gaaggtcgga gtcaacggat tgaattaggt caaatggagc tgtgtg         46

<210> SEQ ID NO 188
<211> LENGTH: 22
<212> TYPE: DNA
<213> ORGANISM: artificial
<220> FEATURE:
<223> OTHER INFORMATION: primer

<400> SEQUENCE: 188
cgacacgccc tcctaagctc at         22

<210> SEQ ID NO 189
<211> LENGTH: 50
<212> TYPE: DNA
<213> ORGANISM: artificial
<220> FEATURE:
<223> OTHER INFORMATION: primer

<400> SEQUENCE: 189
gaaggtgacc aagttcatgc tatgacgatt ctcatttgtg cagataaata         50

<210> SEQ ID NO 190
<211> LENGTH: 48
<212> TYPE: DNA
<213> ORGANISM: artificial
<220> FEATURE:
<223> OTHER INFORMATION: primer

<400> SEQUENCE: 190
gaaggtcgga gtcaacggat tgacgattct catttgtgca gataaatg         48

```
<210> SEQ ID NO 191
<211> LENGTH: 29
<212> TYPE: DNA
<213> ORGANISM: artificial
<220> FEATURE:
<223> OTHER INFORMATION: primer

<400> SEQUENCE: 191
aggagatcca gaaacaacct taaccttaa                                   29

<210> SEQ ID NO 192
<211> LENGTH: 47
<212> TYPE: DNA
<213> ORGANISM: artificial
<220> FEATURE:
<223> OTHER INFORMATION: primer

<400> SEQUENCE: 192
gaaggtgacc aagttcatgc tgcgagtagc aagttaagat catatgg               47

<210> SEQ ID NO 193
<211> LENGTH: 47
<212> TYPE: DNA
<213> ORGANISM: artificial
<220> FEATURE:
<223> OTHER INFORMATION: primer

<400> SEQUENCE: 193
gaaggtcgga gtcaacggat tgcgagtagc aagttaagat catatga               47

<210> SEQ ID NO 194
<211> LENGTH: 29
<212> TYPE: DNA
<213> ORGANISM: artificial
<220> FEATURE:
<223> OTHER INFORMATION: primer

<400> SEQUENCE: 194
catgttatcc ccatctttct gccttattt                                   29

<210> SEQ ID NO 195
<211> LENGTH: 47
<212> TYPE: DNA
<213> ORGANISM: artificial
<220> FEATURE:
<223> OTHER INFORMATION: primer

<400> SEQUENCE: 195
gaaggtgacc aagttcatgc tgcatatacg cactacattt cggaata              47

<210> SEQ ID NO 196
<211> LENGTH: 47
<212> TYPE: DNA
<213> ORGANISM: artificial
<220> FEATURE:
<223> OTHER INFORMATION: primer

<400> SEQUENCE: 196
gaaggtcgga gtcaacggat tgcatatacg cactacattt cggaatc              47

<210> SEQ ID NO 197
<211> LENGTH: 29
<212> TYPE: DNA
<213> ORGANISM: artificial
<220> FEATURE:
<223> OTHER INFORMATION: primer
```

<400> SEQUENCE: 197
ccccgttcca tttataatg cgtatgatt                                          29

<210> SEQ ID NO 198
<211> LENGTH: 4472
<212> TYPE: DNA
<213> ORGANISM: artificial
<220> FEATURE:
<223> OTHER INFORMATION: synthesized

<400> SEQUENCE: 198

| | | | | | |
|---|---|---|---|---|---|
| ctcgagtgtc | atgatttcag | atctaaaccc | tttatgtttt | tatcaatata | tctgagttcc | 60 |
| taatcctata | tggtagttat | gtgcactttt | tattgttctg | aaccgtagac | cccaaggtag | 120 |
| caacatgaaa | gggggatta | aagggttgaa | acattgatc | atgaaagagt | cccctctgc | 180 |
| ctattacatc | cactgttttg | cacatcaact | tcaattggtt | cttacagccg | tggcaaaaga | 240 |
| aaatgaacca | tgttcgtggt | tctttgatca | tgtttcttaa | ttgcttaata | ttcttggagt | 300 |
| ttcttgcaag | tgacatgaca | tgctttgaga | tgttagagct | caaaaggttt | tggaagcact | 360 |
| tgaaatgggt | gagattgaaa | gtggaagtgg | gctaaatcaa | gagatgggac | tagctagacc | 420 |
| cggcgatact | agttggggtt | ctcattttaa | gaccattatg | cacattgtta | gcatgtatcc | 480 |
| acaatccttg | aagtacttga | tgctattgga | aagatcctt | cacaaaaagg | cgagtggaca | 540 |
| agaatatgtt | gagttactca | tgcttttgtt | ttcaatcttc | gtttgatgct | agttattcgt | 600 |
| ggctatacaa | atgagttgtc | caaatctttg | caaagagag | atcaagatat | tgttaatgca | 660 |
| atgcacttg | ttagtttggc | aaatagtaga | atgcaacaca | tgaggtctca | tggttgggaa | 720 |
| gaatttcttg | caaagatgac | cttatttggc | aacaaaaatg | acactgaagt | tcatttgtgg | 780 |
| taggatactt | ataagcctca | tggaagatca | cgtcggtatt | atgaagtaca | aacaaatgat | 840 |
| gatcattata | gaagagaaat | gtatcttggt | gtcattgatt | aaaccattca | agagcttgac | 900 |
| aatcggtttg | atgaggttta | catggagtta | cttatttgca | tgttggcttt | gaatcccctc | 960 |
| aattcatttg | cttctgacga | tgcaatcaag | gtaatgagac | ttgtcgcatt | ctatcccatg | 1020 |
| gacatatcaa | gtacatattt | gataaggcta | taatttcaac | ttgctaattt | tgttgatgat | 1080 |
| acgagacaat | acgataggtt | tagaaatgca | agtaatattg | gtgagctctc | tattatgctt | 1140 |
| gttgcaacaa | tgaaacatgt | tctttatgat | ttggtctact | tactcatcaa | attgatattg | 1200 |
| attttaccga | tggtgactgc | gagtgttgaa | agagtatttt | ggatcatgaa | tatagcgaaa | 1260 |
| agtaagttaa | ggactagtat | gagtgatgac | cgcttgaatg | attgcttggt | gatatttatt | 1320 |
| gagcgggatg | tgttcatgaa | agcatgtgaa | gatgacatag | ttgatgcttt | catggcaatg | 1380 |
| caaaacgtag | agttacctac | tgttatgatt | ttctacttgt | gcttctttca | tgtaagacta | 1440 |
| ttcgtattgt | tggagatttg | aattgaacta | tccttgttat | tcttttgcc | atgttttgtt | 1500 |
| tgacacactt | ggattaggta | cagaaaaaaa | tagtgtgcac | gcccttcgtt | ttattcctgg | 1560 |
| gttgtcatta | ggccgtacca | ggagcgatcg | tgtcctgttg | attattaaga | ccacagtgat | 1620 |
| ctggctcaga | cggtagtaaa | ctggatcgtg | ttaatttagg | ttaagttata | atgaaacttc | 1680 |
| ttatcccgca | aaaagttaa | tggaacccct | ttccttcgaa | aaaagataa | cggacgaatg | 1740 |
| cccgcagaaa | aaccgagtgt | tgatgacagc | tagcgacagg | cactggatca | tcacgagccg | 1800 |
| tcggatgtgc | ccaactttgc | gccgcctttg | ttaacggacg | ggcatgatcg | cttttgcaaa | 1860 |
| ccctcagca | ttacacactc | acaccctaaa | accaccaggc | atcatcacct | caccacccat | 1920 |
| cccgccccga | tacgagagag | agagtgggga | cgggtgtgct | gagagcctga | gacatggccc | 1980 |

```
ccaccgccct cctcatcgtc gtcctcgccg tcgctgccct ccacgccccc gccgcctccg    2040
ccgcgttgtc ccaggagcca ccagcgacgc cgtgcgcggc agccatcgtg tccttctcgc    2100
cgtgcctggc gcacgtcgcg gtggtggcgc cgcccgccct gccctcgccc gcgcccacca    2160
gcgcctgctg cgcggcgttc ctgcgcgccg tttcctccgg ggacgggatg cttctgccac    2220
ctgctccgca acccgctcct cctcggcttc cccgtcgacg ccgcgcgcct cggcactctc    2280
ctccccacct gcgcctccgc gaaaacctcc gccgccacgg ccgccgaggc cgaggccctc    2340
ttcgccgaca agtgccgagg tgagaaatct gtcccttcgt gctccctatt tatgctcgtg    2400
caatatgtat gcttcgatca attctcgtgc gccatatgcg cgtgctgtcg cgttcctgtt    2460
gttgatcgcc gatcgaagca aattttactc tgcaaagtcc taactactgt tgttctcatg    2520
atccttgtac aactactttc gtaatggttg gttgtaatgc ggattactga cgagctctga    2580
atgctactag ggatattagc acttgcatta ctgaactagt ggaatggggg agaaacaccg    2640
cgggattttt cttttgttat taaggagaag atactgagtg gcccagactt acttctgcgt    2700
ttttgctgcg atttgtcatg attaccgttg atttaagcag tttgttgggt tgcttgtttg    2760
atagtagtag taatttcaca aaatattggc gatatttata aatagctaag gcttcgtta    2820 cttggtggtt tctctcaaag agttcacaaa agtcaattat taaattcaat taagggggca    2880
agtattagta gtactggcta actccatttg ccatttgcca attgaaacag agctcaagtc    2940
actgcctgag atgcatttta cacctccatc gccacctccc gcaccaaaac tttctccagg    3000
taaatgttct gctgcttgtc taatgattcc atagcttgtt aaaaaaaatg attccataaa    3060
tctgtgccca gtaatgctat ttcggatttc ggttgaatga accaattggc atttgggcag    3120
acatgtcata tgtcctctcc taccaaatga aacttgaact tgttttatct tgtggtgctc    3180
catccatttc gtgttctatg ccacaactgt acaggttcaa atgatagtag aacaactaat    3240
tttgcatcgg atactctctg cagcctctgt tctgttccta ctaattgcag gaccgagtct    3300
gtctttgtga tactatctgc tttgcgtgca ctgctctttt aggttgcagc tgcaccttct    3360
attttgttca cctgagcatt ccattttggt cgactgaaca ccgcaagtcc tgaatatctt    3420
tcttgaatcg tcggtcttac ttggtgtgca ctagttaaac tgctgtgtat gcccttgcag    3480
ctgccgttac agaaccagcg tccccgactc cgaagatgga ggagcattcg acctcgacga    3540
cgcctgtgtc ggatgatcgg tcgggatccg atgccttgtg tgcctgccgg tcttccttg    3600 tggccttggt cttgggagca gcagtcttga tcacgctgca gttctgatgg atgttcgacc    3660
tcgctcttga aaggtctttg ccctcgctct tgatacaata cttgtgcgcg atgctgcgcc    3720
attcttgatt ggacctcttg ttgcatacgg tgaggtgcca cgtgatgcag gcatgatat    3780 tggtataccct gggaactctt cctgaccagt gcagtttgtt ccgtgcgcgt tttgatgacc    3840
tgacaacgca agtagtaact gttatccggt gacataatcg tatcatttca aacatggtac    3900
agatttatac aatgcagttt agtttctctt gcgatttatt actttctgtg aatctgcatg    3960
ccattctctt gcactcgctg agagagacgg agaactcact ggaatttgtt ttcactatac    4020
aaatatgcgc agttgcagca cacgcacgaa caaatacaaa gtcacacatc attcgcattt    4080
ttctttcaga gttacacatt tgaaatgaag gggaagaaaa acagaagtag catcgtcagc    4140
ggaatgaagc attacatgcc aattggttgc tgatcaggtt cagtctgtgg actgaatgta    4200
ttctaggtac attatatgag caatgacagt agccctgctg ccacgatcga ggaggcgaga    4260
actacggagg atatcccacg acagagcttc cggtgggcgc tggacgggtt gaacatgctg    4320
```

```
tcacgcgggt acatctgccc cggcgtcccc actatgccaa acaccggcgc cggctgcacg   4380
tacgggtaca cgtacggctc agccggcggt ggaaggtagt acacgggcgt tggttccggc   4440
tccgacggcg gtgggtagta gtagtacact gg                                 4472

<210> SEQ ID NO 199
<211> LENGTH: 1047
<212> TYPE: DNA
<213> ORGANISM: Triticum aestivum

<400> SEQUENCE: 199
atggccccca ccgccctcct cctcgtggtc ctcgccgtcg ccgccctcca cgccctgcc     60 gcctccgccg cgttgtccca ggagccacca gcgatgcggg attttctttt tgtgcccag   120 acttacttct gcatttttgc tgcgatttgt catgattacc gttcagttaa gcagtttgtt   180
gggttgcttg tttgatagta gtaatttcac aaaatattgg cgatatttat aaatagctaa   240
gggcttcgtt acttggtggt ttctctcaaa gagttcacaa aagtcaatca ttaaatcaat   300 taaggggggca agtattagta gtactggcta actccatttg ccatttgcca attgaaacag   360
agctcaagtc actgcctgag atgcatttta cacctccatc gccacctccc gcaccaaaac   420
tttctccagg taaacgttct ccctcttgtc taatgatttg ataaatctgt gcccagtcta   480
ttcgggtttc ggttgaataa accaattggc atttgggcag catgttatat ggtctctcct   540
catcccaaat aaaacttgaa cttgttttat cttgccgtgc tccgtccatt ttgtgctcta   600
tgccgcaatt gcacaggttc aatgatagta gaacacctag ttttgcatcg catactctct   660
gcagcctctg ttctgttcct gctaattgca gtatcgggtc tgtcttgtg atactatctc   720 cttttgcatgc actgcactt taggttgcag ttgcacgttt gattctagtt tgttcacctg   780
agcattccat ttggtcgac tgaacaccgc aagtcctgaa tatctttctt gaatcgtcgg   840
tcgtacttcg tgtgcactag ttaaactgct gtctatgccc ttgcagctgc cgttccagaa   900
ccagcgtccc cgaagatgga ggagcattcg acctcagcga cgcctgtgcc ggatgatcgg   960
tcgggatccg atgccttgtg tgcctgccgg gtcttccttg tggccttggt cttgggagca  1020
gcagtcttga tcacgctgca gttctga                                      1047

<210> SEQ ID NO 200
<211> LENGTH: 735
<212> TYPE: DNA
<213> ORGANISM: Triticum aestivum

<400> SEQUENCE: 200
ttataaattc ttgcatgtca aactaaatcg atacatttta aaggcctaaa gctgatctac     60
aatattgtta aatatttgct ttactaattc ctgctctaac acaaaggtta atgacagaat    120
taacaacatc gtgcatgtca agaaaataac atcttgcatg cagcagcagt ggccggctaa    180
aagcgcatgc agtagcagta ccaatcagca acagtggccg gctaaaagcg catgcagcag    240
tagcaatcaa cgtagtagta gagcagcagg gccatgaaca gggctgccgc cagcccgcga    300
ggcggccgtt ccccaggtac agtactgccg ccacgcccct ggcggctgg gccccacacg    360 ccgctgccgt tccgtcgcca gcgccgattc ccgttggtac agtgctgtcg cctcgctgtg    420
tggcggcagg tgccacgtgt cgcctgccgc acctgccgcc acagctgagg ggtcctttt    480 tgttaaattt atcggcaggt ggtccttttt gtcaattcat tcgcgcatgt ggtccttttc    540
aataaaaaat ctcctatgcg cccaccttg cgcggtcttg ttaaacccct cagtattaca    600
cttttttttt gcggggacag tattacacac tcacgcccta aaaccaccag gcatcatcac    660
```

```
ctcaccaccc atcccgcccc aatacgagag aaagagagag agagagtggg gacgggtgtg    720
ctgagagcct gagac                                                     735

<210> SEQ ID NO 201
<211> LENGTH: 420
<212> TYPE: DNA
<213> ORGANISM: Triticum aestivum

<400> SEQUENCE: 201
tggatgttcg acctcgctct tgatacaata cctgtgcatt gctgcgtcat tcttgattgg    60
atcctcttgt tgcatacggt gaagtgccac gtgatgcagg gcgtgatacc tgagaactct    120
tcctgactag tgcagtttgt tctgtgcgcg ttttggatga cctgacaacg caagtaactg    180
ttatccggtg acatactcgt atcgtttcaa acatggtata gatttataca atgcagtcta    240
gtttctcttg cgattttctt tctgtgaatc tgcatgccat ttccttgcgc tcgctgagag    300
agacgagaac tcaggagcac agcacaggag caaactctca tgctttcatg gtgcatgacc    360
ttgctgcgct agctgcgccg gtgaccactc cggtcccggc ggccaccagt cccccccccc    420

<210> SEQ ID NO 202
<211> LENGTH: 1356
<212> TYPE: DNA
<213> ORGANISM: Triticum aestivum

<400> SEQUENCE: 202
gaccaagccc gttattctga cagttctggt gctcaacaca tttatattta tcaaggagca    60
cattgttact cactgctagg agggaatcga actaggaata ttgatcagag gaactacgag    120
agagctgaag ataactgccc tctagctctc actgatctgg gtcgcatagt gagatgcagc    180
ccacgtgagt tcagcaacgg tctagcgctg ggcttttagg cccgcatgat cgggcttttg    240
tcgggtggtc gacgtgttca cgattgggga gagcaacgca gcagttcctc ttagtttagt    300
cccacctcgc ctgtccagca gagttctgac cggtttataa actcgcttgc tgcatcagac    360
ttagccgaac cccaaaaaga gaaaaagtga tccctggtgg tccggatttg gcattgccga    420
ctgcccaaac atgcctcgcc atttcattc tccccttgca tatatgttcg atttgaggtt     480
cgcatatagt ctagtcatat gcggactatt tctgaggttt ggttggacga cgtttctcct    540
ctctcctatt catgatgcct tatgggcaag atatttgttt cactgatatt ttagtttttcc   600 ccgtttctta aaacatgctt attctcttta gcatggccaa caaatttgta agagacccac    660
cgagaggtga ccgaccaaaa tagcaactaa agcatgaaaa aatctcaccg gcagaaggaa    720
ccgcgcggcg caagcgcggg tatccctcta gtacactact acttgcccat agagccagtg    780
gtgtacgagt acgaccgacg atgccttaga cttagacttc ccagtccgtg caccggaagc    840
acagaaccgt ccacgactcc acggacagaa ttcgctccat caacacccac caccacacca    900
gcagtagctt tcttcacgtg aaaaacaacc acatatacat gcctgccgta gacgacaccc    960
atgtactcta ccatatatgt acggtcgaga cgatacatcg gcacatcgcg cctacgtgcc   1020
cccaaagcat gaaatcaatc gacatgacac atgaacctca cgtgagcaca cctcttttg   1080 attttatctt ttttgcaaat cctctttttt gatttccggc tcggctcctc tagttgggcc   1140
cgaagcaggg catatggcaa atgctccagc tcgattcctt aagtgggccg gctgaggagg   1200
atcaagtata cacgaggata cagcccactt ggccgtttgg tggcatcccg cggtcctggt   1260
gcttgctgaa cgcagcgaac gaccctggtt tagtcccacc tcgctcaccg gaagaagcat   1320
```

```
cgatcggttt ataagccccg cgcttgcacc ctcgct                              1356
```

<210> SEQ ID NO 203
<211> LENGTH: 978
<212> TYPE: DNA
<213> ORGANISM: artificial
<220> FEATURE:
<223> OTHER INFORMATION: synthesized

<400> SEQUENCE: 203

```
atgagcccag aacgacgccc ggccgacatc cgccgtgcca ccgaggcgga catgccggcg    60
gtctgcacca tcgtcaacca ctacatcgag acaagcacgg tcaacttccg taccgagccg   120
caggaaccgc aggagtggac ggacgacctc gtccgtctgc gggagcgcta tccctggctc   180
gtcgccgagg taaacaacat cgtctctgtc tttctactca ttttctagct gacggacgga   240
agtcaataac atcaactgtg tagaactaaa ttctagcctg ttaatgtatc aaaaatgtca   300
atcttatttg caggtggacg cgaggtcgc cggcatcgcc tacgcgggcc cctggaaggc    360
acgcaacgcc tacgactgga cggccgagtc gaccgtgtac gtctcccccc gccaccagcg   420
gacgggactg ggctccacgc tctacaccca cctgctgaag tccctggagg cacagggctt   480
caagagcgtg gtcgctgtca tcgggctgcc caacgacccg agcgtgcgca tgcacgaggc   540
gctcggatat gccccccgcg gcatgctgcg ggcggccggc ttcaagcacg gaactggca    600
tgacgtgggt ttctggcagc tggacttcag cctgccggtc cgccccgtc cggtcctgcc    660
cgtcaccgag atttgatctg tacattgctt tgggtttcct tctccattat ctttcttgtt   720
tgttcctaag aatatgtgta tgtccatgtt catgtaccaa catgctcgag aaagcatgct   780
cgtatgtgaa tgcaatcggt ggctatgtat atgcacatgc acataatata ttatacaatc   840
tgtcgactat gtattcgggt aattaataat gagaaacatc tttggcaccg cacgcacatc   900
ttttattccg ccgctagaca tagtttatgt tggaatgatg agcaatcaag aataacacgg   960
taaggcattg tctgatac                                                 978
```

<210> SEQ ID NO 204
<211> LENGTH: 107
<212> TYPE: DNA
<213> ORGANISM: artificial
<220> FEATURE:
<223> OTHER INFORMATION: synthesized

<400> SEQUENCE: 204

```
gctgtcttca acacaagaag acacgtttta gagctagaaa tagcaagtta aaataaggct    60
agtccgttat caacttgaaa agtggcacc gagtcggtgc ttttttt                  107
```

<210> SEQ ID NO 205
<211> LENGTH: 1991
<212> TYPE: DNA
<213> ORGANISM: zea mays

<400> SEQUENCE: 205

```
gtgcagcgtg acccggtcgt gcccctctct agagataatg agcattgcat gtctaagtta    60
taaaaaatta ccacatattt tttttgtcac acttgtttga agtgcagttt atctatcttt   120
atacatatat ttaaactta ctctacgaat aatataatct atagtactac aataatatca    180
gtgttttaga gaatcatata aatgaacagt tagacatggt ctaaaggaca attgagtatt   240
ttgacaacag gactctacag ttttatcttt ttagtgtgca tgtgttctcc ttttttttg   300
caaatagctt cacctatata atacttcatc cattttatta gtacatccat ttagggttta   360
```

```
gggttaatgg ttttatagga ctaatttttt tagtacatct attttattct attttagcct      420
ctaaattaag aaaactaaaa ctctatttta gtttttttat ttaataattt agatataaaa      480
tagaataaaa taaagtgact aaaaattaaa caaataccct ttaagaaatt aaaaaaacta      540
aggaaacatt tttcttgttt cgagtagata atgccagcct gttaaacgcc gtcgacgagt      600
ctaacggaca ccaaccagcg aaccagcagc gtcgcgtcgg gccaagcgaa gcagacggca      660
cggcatctct gtcgctgcct ctggacccct ctcgagagtt ccgctccacc gttggacttg      720
ctccgctgtc ggcatccaga aattgcgtgg cggagcggca gacgtgagcc ggcacggcag      780
gcggcctcct cctcctctca cggcaccggc agctacgggg gattcctttc ccaccgctcc      840
ttcgctttcc cttcctcgcc cgccgtaata aatagacacc ccctccacac cctctttccc      900
caacctcgtg ttgttcggag cgcacacaca cacaaccaga tctcccccaa atccaccgt      960
cggcacctcc gcttcaaggt acgccgctcg tcctcccccc cccccctctc taccttctct     1020
agatcggcgt tccggtccat gcatggttag ggcccggtag ttctacttct gttcatgttt     1080
gtgttagatc cgtgtttgtg ttagatccgt gctgctagcg ttcgtacacg gatgcgacct     1140
gtacgtcaga cacgttctga ttgctaactt gccagtgttt ctctttgggg aatcctggga     1200
tggctctagc cgttccgcag acgggatcga tttcatgatt ttttttgttt cgttgcatag     1260
ggtttggttt gccctttcc tttatttcaa tatatgccgt gcacttgttt gtcgggtcat     1320
cttttcatgc ttttttttgt cttggttgtg atgatgtggt ctggttgggc ggtcgttcta     1380
gatcggagta gaattctgtt tcaaactacc tggtggattt attaattttg gatctgtatg     1440
tgtgtgccat acatattcat agttacgaat tgaagatgat ggatggaaat atcgatctag     1500
gataggtata catgttgatg cgggttttac tgatgcatat acagagatgc ttttgttcg      1560
cttggttgtg atgatgtggt gtggtgggc ggtcgttcat tcgttctaga tcggagtaga     1620
atactgtttc aaactacctg gtgtatttat taatttgga actgtatgtg tgtgtcatac     1680
atcttcatag ttacgagttt aagatggatg gaaatatcga tctaggatag gtatacatgt     1740
tgatgtgggt tttactgatg catatacatg atggcatatg cagcatctat tcatatgctc     1800
taaccttgag tacctatcta ttataataaa caagtatgtt ttataattat tttgatcttg     1860
atatacttgg atgatggcat atgcagcagc tatatgtgga tttttttagc cctgccttca     1920
tacgctattt atttgcttgg tactgttct tttgtcgatg ctcaccctgt tgtttggtgt     1980
tacttctgca g                                                          1991
```

<210> SEQ ID NO 206
<211> LENGTH: 4750
<212> TYPE: DNA
<213> ORGANISM: artificial
<220> FEATURE:
<223> OTHER INFORMATION: synthesized

<400> SEQUENCE: 206

```
atggctccta agaagaagcg gaaggttggt attcacgggg tgcctgcggc tatggataag       60
aagtacagca ttggtctgga catcgggacg aattccgttg ctgggccgt gatcaccgat      120
gagtacaagg tcccttccaa gaagtttaag gttctgggaa acaccgatcg gcacagcatc      180
aagaagaatc tcattggagc cctcctgttc gactcaggcg agaccgccga agcaacaagg      240
ctcaagagaa ccgcaaggag acggtataca agaaggaaga ataggatctg ctacctgcag      300
gagattttca gcaacgaaat ggcgaaggtg gacgattcgt tctttcatag attggaagaa      360
```

```
agtttcctcg tcgaggaaga taagaagcac gagaggcatc ctatctttgg caacattgtc    420
gacgaggttg cctatcacga aaagtacccc acaatctatc atctgcggaa gaagcttgtg    480
gactcgactg ataaggcgga ccttagattg atctacctcg ctctggcaca catgattaag    540
ttcaggggcc attttctgat cgaggggat cttaacccgg acaatagcga tgtggacaag     600
ttgttcatcc agctcgtcca aacctacaat cagctctttg aggaaaaccc aattaatgct    660
tcaggcgtcg acgccaaggc gatcctgtct gcacgccttt caaagtctcg ccggcttgag    720
aacttgatcg ctcaactccc gggcgaaaag aagaacggct tgttcgggaa tctcattgca    780
ctttcgttgg ggctcacacc aaacttcaag agtaattttg atctcgctga ggacgcaaag    840
ctgcagcttt ccaaggacac ttatgacgat gacctggata acctttggc ccaaatcggc     900
gatcagtacg cggacttgtt cctcgccgcg aagaatttgt cggacgcgat cctcctgagt    960
gatattctcc gcgtgaacac cgagattaca aaggccccgc tctcggcgag tatgatcaag   1020
cgctatgacg agcaccatca ggatctgacc cttttgaagg ctttggtccg gcagcaactc   1080
ccagagaagt acaaggaaat cttctttgat caatccaaga acggctacgc tggttatatt   1140
gacggcgggg catcgcagga ggaattctac aagtttatca agccaattct ggagaagatg   1200
gatggcacag aggaactcct ggtgaagctc aataggagg accttttgcg gaagcaaaga    1260
actttcgata acggcagcat ccctcaccag attcatctcg gggagctgca cgccatcctg   1320
agaaggcagg aagacttcta ccccttctct taaggataacc gggagaagat cgaaaagatt   1380
ctgacgttca gaattccgta ctatgtcgga ccactcgccc ggggtaattc cagatttgcg   1440
tggatgacca gaaagagcga ggaaaccatc acaccttgga acttcgagga agtggtcgat   1500
aagggcgctt ccgcacagag cttcattgag cgcatgacaa attttgacaa gaacctgcct   1560
aatgagaagg tccttcccaa gcattccctc ctgtacgagt atttcactgt ttataacgaa   1620
ctcacgaagg tgaagtatgt gaccgaggga atgcgcaagc ccgccttcct gagcggcgag   1680
caaaagaagg cgatcgtgga ccttttgttt aagaccaatc ggaaggtcac agttaagcag   1740
ctcaaggagg actacttcaa gaagattgaa tgcttcgatt ccgttgagat cagcggcgtg   1800
gaagacaggt ttaacgcctc actggggact taccacgatc tcctgaagat cattaaggat   1860
aaggacttct tggacaacga ggaaaatgag gatatcctcg aagacattgt cctgactctt   1920
acgttgtttg aggataggga aatgatcgag gaacgcttga agacgtatgc ccatctcttc   1980
gatgacaagg ttatgaagca gctcaagaga agaagataca ccggatgggg aaggctgtcc   2040
cgcaagctta tcaatggcat tagagacaag caatcaggga agacaatcct tgacttttg    2100
aagtctgatg gcttcgcgaa caggaatttt atgcagctga ttcacgatga ctcacttact   2160
ttcaaggagg atatccagaa ggctcaagtg tcgggacaag gtgacagtct gcacgagcat   2220
atcgccaacc ttgcgggatc tcctgcaatc aagaagggta ttctgcagac agtcaaggtt   2280
gtggatgagc ttgtgaaggt catgggacgg cataagcccg agaacatcgt tattgagatg   2340
gccagagaaa atcagaccac acaaaagggt cagaagaact cgagggagcg catgaagcgc   2400
atcgaggaag gcattaagga gctggggagt cagatcctta aggagcaccc ggtggaaaac   2460
acgcagttgc aaaatgagaa gctctatctg tactatctgc aaaatggcag ggatatgtat   2520
gtggaccagg agttggatat taaccgcctc tcggattacg acgtcgatca tatcgttcct   2580
cagtccttcc ttaaggatga cagcattgac aataaggttc tcaccaggtc cgacaagaac   2640
cgcgggaagt ccgataatgt gcccagcgag gaagtcgtta agaagatgaa gaactactgg   2700
aggcaacttt tgaatgccaa gttgatcaca cagaggaagt ttgataacct cactaaggcc   2760
```

```
gagcgcggag gtctcagcga actggacaag gcgggcttca ttaagcggca actggttgag    2820
actagacaga tcacgaagca cgtggcgcag attctcgatt cacgcatgaa cacgaagtac    2880
gatgagaatg acaagctgat ccgggaagtg aaggtcatca ccttgaagtc aaagctcgtt    2940
tctgacttca ggaaggattt ccaatttat aaggtgcgcg agatcaacaa ttatcaccat     3000
gctcatgacg catacctcaa cgctgtggtc ggaacagcat tgattaagaa gtacccgaag    3060
ctcgagtccg aattcgtgta cggtgactat aaggtttacg atgtgcgcaa gatgatcgcc    3120
aagtcagagc aggaaattgg caaggccact gcgaagtatt tcttttactc taacattatg    3180
aatttcttta agactgagat cacgctggct aatggcgaaa tccggaagag accacttat    3240 gagaccaacg gcgagacagg ggaaatcgtg tgggacaagg ggagggattt cgccacagtc    3300
cgcaaggttc tctctatgcc tcaagtgaat attgtcaaga agactgaagt ccagacgggc    3360
gggttctcaa aggaatctat tctgcccaag cggaactcgg ataagcttat cgccagaaag    3420
aaggactggg atccgaagaa gtatggaggt ttcgactcac caacggtggc ttactctgtc    3480
ctggttgtgg caaggtgga aagggaaag tcaagaagc tcaagtctgt caaggagctc       3540
ctgggtatca ccattatgga gaggtccagc ttcgaaaaga atccgatcga ttttctcgag    3600
gcgaagggat ataaggaagt gaagaaggac ctgatcatta gcttccaaa gtacagtctt    3660 ttcgagttgg aaaacggcag gaagcgcatg ttggcttccg caggagagct ccagaagggt    3720
aacgagcttg ctttgccgtc caagtatgtg aacttcctct atctggcatc ccactacgag    3780
aagctcaagg gcagcccaga ggataacgaa cagaagcaac tgtttgtgga gcaacacaag    3840
cattatcttg acgagatcat tgaacagatt tcggagttca gtaagcgcgt catcctcgcc    3900
gacgcgaatt tggataaggt tctctcagcc tacaacaagc accggacaa gcctatcaga    3960 gagcaggcgg aaaatatcat tcatctcttc accctgacaa accttggggc tcccgctgca    4020
ttcaagtatt ttgacactac gattgatcgg aagagataca cttctacgaa ggaggtgctg    4080
gatgcaaccc ttatccacca atcgattact ggcctctacg acacgcggat cgacttgagt    4140
cagctcggtg gcgataagag acccgcagca accaagaagg cagggcaagc aaagaagaag    4200
aagtgactaa ctaactaggc gcgcccgggt accgttttc tcagacagtt ttctaaaaa     4260 agggcgttc tggggaagtt cgagatggtt cgtaaggtgt tactggctcc tgtgaaccaa    4320
tacatgatac tgccatgata agggttataa ttagtcaagc agagtaagaa gaaacaacag    4380
tagcagtgac tccgattcct gaagatgagt catatttgtc ttgtgctcct gctgtatgaa    4440
atggatcgca tgtgtatatt cgtcgccgcg ccgcactggt gtaacctgtt gcctcagagt    4500
ttgcttttag ctggtctgt tttaaaata agtactgttt tttggttggc tgcaagccat     4560
tctgaacttc agtttaccaa ttgttttat gttgtggttg aatatttaa ttttttattt     4620 aatgtttggt tctttttta tatatatttg caaaaatgat acaagtggtc aagttttcat    4680
atagtatggg ctctatttcc tagagctcta cctctaggaa cgaatttgt ggaggttttc    4740 ttttggctag                                                           4750
```

<210> SEQ ID NO 207
<211> LENGTH: 517
<212> TYPE: DNA
<213> ORGANISM: artificial
<220> FEATURE:
<223> OTHER INFORMATION: synthesized

<400> SEQUENCE: 207

```
gtttttctca gacagttttc taaaaaaagg gcgtttctgg ggaagttcga gatggttcgt      60
aaggtgttac tggctcctgt gaaccaatac atgatactgc catgataagg gttataatta    120
gtcaagcaga gtaagaagaa acaacagtag cagtgactcc gattcctgaa gatgagtcat    180
atttgtcttg tgctcctgct gtatgaaatg gatcgcatgt gtatattcgt cgccgcgccg    240
cactggtgta acctgttgcc tcagagtttg cttttagctg gttctgtttt aaaaataagt    300 actgttttt ggttggctgc aagccattct gaacttcagt ttaccaattg ttttttatgtt    360 gtggttgaat attttaattt tttatttaat gtttggttct tttttatat atatttgcaa     420 aaatgataca agtggtcaag ttttcatata gtatgggctc tatttcctag agctctacct    480
ctaggaacga attttgtgga ggttttcttt tggctag                             517

<210> SEQ ID NO 208
<211> LENGTH: 486
<212> TYPE: DNA
<213> ORGANISM: artificial
<220> FEATURE:
<223> OTHER INFORMATION: synthesized

<400> SEQUENCE: 208
ggaattccca tggagtcaaa gattcaaata gaggacctaa cagaactcgc cgtaaagact      60
ggcgaacagt tcatacagag tctcttacga ctcaatgaca agaagaaaat cttcgtcaac    120
atggtggagc acgacacgct tgtctactcc aaaaatatca agatacagt ctcagaagac     180 caaagggcaa ttgagacttt tcaacaaagg gtaatatccg gaaacctcct cggattccat    240
tgcccagcta tctgtcactt tattgtgaag atagtggaaa aggaaggtgg ctcctacaaa    300
tgccatcatt gcgataaagg aaaggccatc gttgaagatg cctctgccga cagtggtccc    360
aaagatggac ccccacccac gaggagcatc gtggaaaaag aagacgttcc aaccacgtct    420
tcaaagcaag tggattgatg tgatatctcc actgacgtaa gggatgacgc acaatcccac    480
taagct                                                                486

<210> SEQ ID NO 209
<211> LENGTH: 856
<212> TYPE: DNA
<213> ORGANISM: artificial
<220> FEATURE:
<223> OTHER INFORMATION: synthesized

<400> SEQUENCE: 209
ctctagaact agtggatctc gatgtgtagt ctacgagaag ggttaaccgt ctcttcgtga      60
gaataaccgt ggcctaaaaa taagccgatg aggataaata aaatgtggtg gtacagtact    120
tcaagaggtt tactcatcaa gaggatgctt ttccgatgag ctctagtagt acatcggacc    180
tcacatacct ccattgtggt gaaatatttt gtgctcattt agtgatgggt aaattttgtt    240
tatgtcactc taggttttga catttcagtt ttgccactct taggttttga caaataattt    300
ccattccgcg gcaaaagcaa aacaatttta ttttactttt accactctta gctttcacaa    360
tgtatcacaa atgccactct agaaattctg tttatgccac agaatgtgaa aaaaaacact    420
cacttatttg aagccaaggt gttcatggca tggaaatgtg acataaagta acgttcgtgt    480
ataagaaaaa attgtactcc tcgtaacaag agacggaaac atcatgagac aatcgcgttt    540
ggaaggcttt gcatcacctt tggatgatgc gcatgaatgg agtcgtctgc ttgctagcct    600
tcgcctaccg cccactgagt ccgggcggca actaccatcg gcgaacgacc cagctgacct    660
ctaccgaccg gacttgaatg cgctaccttc gtcagcgacg atggccgcgt acgctggcga    720
``` cgtgccccg catgcatggc ggcacatggc gagctcagac cgtgcgtggc tggctacaaa    780
tacgtacccc gtgagtgccc tagctagaaa cttacacctg caactgcgag agcgagcgtg    840
tgagtgtagc cgagta                                                    856

<210> SEQ ID NO 210
<211> LENGTH: 678
<212> TYPE: DNA
<213> ORGANISM: artificial
<220> FEATURE:
<223> OTHER INFORMATION: synthesized

<400> SEQUENCE: 210
atggcctcct ccgagaacgt catcaccgag ttcatgcgct tcaaggtgcg catggagggc     60
accgtgaacg gccacgagtt cgagatcgag ggcgagggcg agggccgccc ctacgagggc    120
cacaacaccg tgaagctgaa ggtgacgaag ggcggccccc tgcccttcgc ctgggacatc    180 ctgtccccc agttccagta cggctccaag gtgtacgtga agcacccgc cgacatcccc     240 gactacaaga agctgtcctt ccccgagggc ttcaagtggg agcgcgtgat gaacttcgag    300
gacggcggcg tggcgaccgt gacccaggac tcctccctgc aggacggctg cttcatctac    360
aaggtgaagt tcatcggcgt gaacttcccc tccgacggcc ccgtgatgca gaagaagacc    420
atgggctggg aggcctccac cgagcgcctg taccccgcg acggcgtgct gaagggcgag    480
acccacaagg ccctgaagct gaaggacggc ggccactacc tggtggagtt caagtccatc    540
tacatggcca agaagcccgt gcagctgccc ggctactact acgtggacgc caagctggac    600
atcacctccc acaacgagga ctacaccatc gtggagcagt acgagcgcac cgagggccgc    660
caccacctgt tcctgtag                                                  678

<210> SEQ ID NO 211
<211> LENGTH: 311
<212> TYPE: DNA
<213> ORGANISM: artificial
<220> FEATURE:
<223> OTHER INFORMATION: synthesized

<400> SEQUENCE: 211
cctagacttg tccatcttct ggattggcca acttaattaa tgtatgaaat aaaaggatgc     60
acacatagtg acatgctaat cactataatg tgggcatcaa agttgtgtgt tatgtgtaat    120
tactagttat ctgaataaaa gagaaagaga tcatccatat ttcttatcct aaatgaatgt    180
cacgtgtctt tataattctt tgatgaacca gatgcatttc attaaccaaa tccatataca    240
tataaatatt aatcatatat aattaatatc aattgggtta gcaaaacaaa tctagtctag    300
gtgtgttttg c                                                         311

<210> SEQ ID NO 212
<211> LENGTH: 1502
<212> TYPE: DNA
<213> ORGANISM: artificial
<220> FEATURE:
<223> OTHER INFORMATION: synthesized

<400> SEQUENCE: 212
gtgcagcgtg acccggtcgt gcccctctct agagataatg agcattgcat gtctaagtta     60
taaaaaatta ccacatattt ttttgtcac acttgtttga agtgcagttt atctatctt    120 atacatatat ttaaactta ctctacgaat aatataatct atagtactac aatataatca    180

-continued

```
gtgttttaga gaatcatata aatgaacagt tagacatggt ctaaaggaca attgagtatt    240
ttgacaacag gactctacag ttttatcttt ttagtgtgca tgtgttctcc tttttttttg    300
caaatagctt cacctatata atacttcatc cattttatta gtacatccat ttagggttta    360
gggttaatgg tttttataga ctaattttt tagtacatct attttattct attttagcct    420
ctaaattaag aaaactaaaa ctctatttta gttttttat ttaataattt agatataaaa    480
tagaataaaa taaagtgact aaaaattaaa caaatacct ttaagaaatt aaaaaacta    540 aggaaacatt tttcttgttt cgagtagata atgccagcct gttaaacgcc gtcgatcgac    600
gagtctaacg gacaccaacc agcgaaccag cagcgtcgcg tcgggccaag cgaagcagac    660
ggcacggcat ctctgtcgct gcctctggac ccctctcgag agttccgctc caccgttgga    720
cttgctccgc tgtcggcatc cagaaattgc gtggcggagc ggcagacgtg agccggcacg    780
gcaggcggcc tcctcctcct ctcacggcac cggcagctac gggggattcc tttcccaccg    840
ctccttcgct ttcccttcct cgcccgccgt aataaataga caccccctcc acacctctt    900 tccccaacct cgtgttgttc ggagcgcaca cacacacaac cagatctccc ccaaatccac    960
ccgtcggcac ctccgcttca aggtacgccg ctcgtcctcc cccccccccc ctctctacct   1020
tctctagatc ggcgttccgg tccatggtta gggcccggta gttctacttc tgttcatgtt   1080
tgtgttagat ccgtgtttgt gttagatccg tgctgctagc gttcgtacac ggatgcgacc   1140
tgtacgtcag acacgttctg attgctaact tgccagtgtt tctctttggg gaatcctggg   1200
atggctctag ccgttccgca gacgggatcg atctaggata ggtatacatg ttgatgtggg   1260
ttttactgat gcatatacat gatggcatat gcagcatcta ttcatatgct ctaaccttga   1320
gtacctatct attataataa acaagtatgt tttataatta ttttgatctt gatatacttg   1380
gatgatggca tatgcagcag ctatatgtgg atttttttag ccctgccttc atacgctatt   1440
tatttgcttg gtactgtttc ttttgtcgat gctcaccctg ttgtttggtg ttacttctgc   1500
ag                                                                   1502
```